US 8,785,120 B2
Jul. 22, 2014

(54) METHOD FOR THE TREATMENT OF A SAMPLE CONTAINING BIOMOLECULES

(75) Inventors: Christian Korfhage, Langenfeld (DE); Friederike Wilmer, Konigswinter-Sand (DE); Dirk Loffert, Dusseldorf (DE); Ralf Himmelreich, Langenfeld (DE); Claudia Fritz, Cologne (DE); Kathleen Rieske, Burscheid (DE)

(73) Assignee: Qiagen GmbH, Hilden (DE)

( * ) Notice: Subject to any disclaimer, the term of this patent is extended or adjusted under 35 U.S.C. 154(b) by 439 days.

This patent is subject to a terminal disclaimer.

(21) Appl. No.: 12/862,156

(22) Filed: Aug. 24, 2010

(65) Prior Publication Data

US 2010/0323363 A1     Dec. 23, 2010

Related U.S. Application Data

(62) Division of application No. 11/910,247, filed as application No. PCT/EP2006/002961 on Apr. 1, 2006, now Pat. No. 7,838,233.

(30) Foreign Application Priority Data

Apr. 1, 2005   (DE) .......................... 10 2005 015 005

(51) Int. Cl.
  *C12Q 1/68*  (2006.01)
  *G01N 33/53*  (2006.01)
  *C07H 21/04*  (2006.01)

(52) U.S. Cl.
  USPC .............................. 435/6.1; 435/7.1; 536/25.4

(58) Field of Classification Search
  USPC ........... 435/6.1, 7.1; 536/22.1, 25.4; 436/174, 436/177, 178
  See application file for complete search history.

(56) References Cited

U.S. PATENT DOCUMENTS

| | | | |
|---|---|---|---|
| 3,887,431 A * | 6/1975 | Robbins et al. ................ 426/656 |
| 5,010,183 A | 4/1991 | MacFarlane |
| 5,234,809 A * | 8/1993 | Boom et al. .................. 435/91.2 |
| 5,258,302 A * | 11/1993 | Vedvick et al. .......... 435/254.23 |
| 5,300,635 A | 4/1994 | MacFarlane |
| 5,346,994 A | 9/1994 | Chomczynski |
| 5,434,079 A * | 7/1995 | Mozayeni ................... 435/286.5 |
| 5,488,042 A * | 1/1996 | Grdina ........................... 514/114 |
| 5,496,562 A | 3/1996 | Burgoyne |
| 5,552,302 A | 9/1996 | Lewis et al. |
| 5,712,095 A | 1/1998 | Britschgi et al. |
| 5,728,822 A | 3/1998 | MacFarlane |
| 5,985,572 A | 11/1999 | MacFarlane |
| 5,989,810 A | 11/1999 | Flanagan et al. |
| 5,990,301 A | 11/1999 | Colpan et al. |
| 5,994,056 A * | 11/1999 | Higuchi ........................ 435/6.18 |
| 6,001,564 A * | 12/1999 | Bergeron et al. ............. 435/6.15 |
| 6,020,186 A | 2/2000 | Henco et al. |
| 6,156,504 A * | 12/2000 | Gocke et al. .................. 435/6.11 |
| 6,180,778 B1 | 1/2001 | Bastian et al. |
| 6,218,105 B1 | 4/2001 | Hall et al. |
| 6,258,930 B1 | 7/2001 | Gauch et al. |
| 6,413,747 B1 * | 7/2002 | Kato et al. .................... 435/91.2 |
| 6,528,641 B2 | 3/2003 | Lader |
| 6,602,718 B1 | 8/2003 | Augello et al. |
| 6,617,108 B1 * | 9/2003 | Willson et al. ...................... 435/5 |
| 6,617,170 B2 | 9/2003 | Augello et al. |
| 6,776,959 B1 * | 8/2004 | Helftenbein .................... 422/50 |
| 6,777,210 B1 | 8/2004 | Pasloske et al. |
| 6,780,632 B1 * | 8/2004 | Hanak et al. .................. 435/270 |

(Continued)

FOREIGN PATENT DOCUMENTS

| | | |
|---|---|---|
| EP | 1044984 | 10/2000 |
| WO | 9012881 | 11/1990 |

(Continued)

OTHER PUBLICATIONS

Antony et al., Selectivity of Polyamines on the Stability of RNA-DNA Hybrids Containing Phosphodiester and Phosphorothioate Oligodeoxyribonucleotides. Biochemistry 38 :10775 (1999).*
Capan et al., Stability of poly(L-lysine)-complexed plasmid DNA during mechanical stress and DNase I treatment. Pharmaceutical Development and Technology 4(4) : 491 (1999).*
Joos et al., Covalent attachment of hybridizable oligonucleotides to glass supports. Analytical Biochemistry 247 : 96-101 (1997).*
Matteucci et al., Synthesis of deoxyoligonucleotides on a polymer support. J. Am. Chem. Soc. 103: 3185-3191 (1981).*
Davis et al. [Basic Methods in Molecular Biology pp. 93-98 (1986)].*

(Continued)

*Primary Examiner* — Ethan Whisenant
(74) *Attorney, Agent, or Firm* — Miles & Stockbridge, PC

(57) ABSTRACT

The invention generally provides a method for the sample preparation for a subsequent preparation, processing or analysis method of a sample containing an at least one species of nucleic acid and/or one species of protein, whereby the method comprises the following steps: A) providing a sample which contains at least one species of a nucleic acid and/or of a protein, B) contacting the sample with a fluid or solid composition to produce a fluid sample preparation, whereby the composition contains at least a nitrogenous compound, which is selected from the group consisting of a) polyamines, b) amino acids, and oligo- and polypeptides, c) nitrogenous heterocyclic compounds, including homo-oder heteropolymeres, which comprise these nitrogenous compounds, d) amines of the type $R^1R^2NR^3$, whereby $R^1$, $R^2$ and $R^3$ are chosen independently from one another from the group consisting of H, $C_1$-$C_5$-alkyl groups and aryl groups, whereby $R^1$, $R^2$ and $R^3$ are not H simultaneously, e) carbonxylic acid amides, f) inorganic ammonium salts, g) ammonium groups containing inner salt compounds, h) antibiotica binding nucleic acid, i) compounds which bind in the small cavity of the DNA, and mixtures of two or more of these compounds. The invention provides in particular a method for the lysis of a biological sample, and methods for the stabilization of biomolecules, a method for the decrease of inhibiting effects in a sample containing biomolecules and a differential masking method.

20 Claims, 13 Drawing Sheets

(56) References Cited

U.S. PATENT DOCUMENTS

| | | | |
|---|---|---|---|
| 6,821,752 B2 | 11/2004 | Sheppard | |
| 6,825,340 B2 | 11/2004 | Pasloske et al. | |
| 6,921,817 B1 | 7/2005 | Banerjee | |
| 7,105,563 B2* | 9/2006 | Arnaiz et al. | 514/414 |
| 7,183,118 B2* | 2/2007 | Aebersold et al. | 436/173 |
| 7,838,233 B2* | 11/2010 | Korfhage et al. | 435/6.1 |
| 7,910,293 B2* | 3/2011 | Sinha et al. | 435/4 |
| 2001/0006949 A1* | 7/2001 | Thorens et al. | 514/44 |
| 2002/0039796 A1* | 4/2002 | Dores et al. | 436/177 |
| 2002/0115851 A1 | 8/2002 | Korfhage et al. | |
| 2002/0146677 A1 | 10/2002 | Augello et al. | |
| 2002/0197637 A1 | 12/2002 | Willson, III et al. | |
| 2003/0059802 A1 | 3/2003 | Bilodeau-Goeseels et al. | |
| 2003/0091992 A1* | 5/2003 | Lorincz et al. | 435/6 |
| 2003/0152687 A1 | 8/2003 | Beaudoin et al. | |
| 2004/0014703 A1 | 1/2004 | Hollander et al. | |
| 2004/0029133 A1* | 2/2004 | Herrnstadt | 435/6 |
| 2004/0048384 A1 | 3/2004 | Augello et al. | |
| 2004/0072742 A1 | 4/2004 | Tojo et al. | |
| 2004/0101947 A1* | 5/2004 | Engel et al. | 435/270 |
| 2004/0115689 A1 | 6/2004 | Augello et al. | |
| 2004/0147547 A1 | 7/2004 | Hu et al. | |
| 2004/0185545 A1 | 9/2004 | Simpson et al. | |
| 2005/0026284 A1* | 2/2005 | Kudlicki et al. | 435/455 |
| 2005/0131057 A1 | 6/2005 | Ueno et al. | |
| 2005/0155921 A1 | 7/2005 | Siddiqi | |
| 2005/0222404 A1* | 10/2005 | Galaev et al. | 536/25.4 |
| 2005/0239068 A1 | 10/2005 | Bosnes | |
| 2006/0105416 A1* | 5/2006 | Pappin et al. | 435/23 |
| 2006/0216771 A1* | 9/2006 | Doeberitz et al. | 435/7.92 |
| 2006/0266468 A1 | 11/2006 | Germano | |
| 2007/0111231 A1* | 5/2007 | Magness et al. | 435/6 |

FOREIGN PATENT DOCUMENTS

| | | |
|---|---|---|
| WO | 9418156 | 8/1994 |
| WO | 94/26867 | 11/1994 |
| WO | 01/49880 | 12/2000 |
| WO | 0149880 | 7/2001 |
| WO | 0200600 | 1/2002 |
| WO | 0206000 | 1/2002 |
| WO | 02/48164 | 6/2002 |
| WO | 02005478 | 7/2002 |
| WO | 02056030 | 7/2002 |
| WO | 02057478 | 7/2002 |
| WO | 02059360 | 8/2002 |
| WO | 03102184 | 12/2003 |
| WO | 2005019235 | 3/2005 |
| WO | 2006094974 | 9/2006 |

OTHER PUBLICATIONS

Balesteri et al., Mechanism of polyamine inhibition of a leaf protease. Arch Biochem Biophys. 255 (2) :460 (1987)—Abstract Only.*
Blackburn et al., Ribonucleasser inhibitor from human placenta. Journal of Biological Chemistry 252(16) :5904 (1977).*
Cho et al.Biochemistry 37 :4985 (1998).*
HALT Protease Inhibitor Cocktail. Product Instructions ThermoFisher Scientific (Downloaded on Sep. 24, 2012).*
Hamasaki et al., Biochemistry 36 : 12323 (1997).*
Terui et al., Stabilization of nucleic acids by unusual polyamines produced by an extreme thermophile, *Thermus thermophilus*. Biochem J. Jun. 1, 2005; 388 (Pt 2): 427-433.*
Brandt et al., Immunogenic Integral Membrane Proteins of *Borrelia burgdorferi* Are Lipoproteins. Infection and Immunity 58(4):983 (1990).*
Miyakawa et al.,New method for detection of *Candida albicansin* human blood by polymerase chain reaction. Journal of Clinical Microbiology 31 (12):3344(1993).*
Schwartz et al. Circulating Tumor Markers in the Monitoring of Gynecologic Malignancies. Cancer 60 (3) :353 (1987).*
European Search Report in EP 10 172588 dated Oct. 5, 2010 (5 pages).
Chomczynski, Piotr et al., "Single-Step Method of RNA Isolation by Acid Guanidinium Thiocyanate-Phenol-Chloroform Extraction," Analytical Biochemistry, No. 162, 1987, pp. 156-159.
Tsurumi, Tatsuya et al., "Functional Expression and Characterization of the Epstein-Barr Virus DNA Polymerase Catalytic Subunit," Journal of Virology, Aug. 1993, pp. 4651-4658.
Coombs et al., "Simultaneious Isolation of DNA, RNA, and Antigenic Protein Exhibiting Kinase Activity form Small Tumor Samples using Guanidine Isothiocyanate", Analytical Biochemistry vol. 188: pp. 338-343 (1990).
Pepinsky, R.B. "Selective Precipitation of Proteins from Guanidine Hydrochloride—Containing Solutions with Ethanol". Analytical Biochemistry vol. 195: pp. 177-181 (1991).
Balewit, J. "RNasin Ribonuclease Inhibitor", Celebrating 15 years of Rnase Inhibition, Promega Notes Magazine No. 56, pp. 31-32 (1996).
Posati et al., "Effects of Instantizing on Amino Acid Content of Nonfat Dry Milk", Journal of Dairy Science 57 (2): pp. 258-260 (1974).
Tiemeyer et al., "Metabolites of Nucleic Acids in Bovine Mille", Journal of dairy Science 67(4) : pp. 723-728 (1984) (1974).
Gorski et al., "Tissue-Specific in Vitro Transcription from the Mouse Albumin Promoter", Cell 47 : pp. 767-776 (1986).
Marton & Feuerstein, Polyamine—DNA Interactions: Possible Site of New Cancer Chemotherapeutic Intervention, Pharmaceutical Research, vol. 3, Issue 6, 311-317, at 311 (Dec. 1986).

* cited by examiner

Legend a    Lysis without additive
b    Imidazole
c    10mM Proline
d    Glutamic acid
e    Histidine
f    Arginine
g    Tryptophane
h    Glycine
i    Pyrimidine
j    Guanine
k    Cytosine
l    Betaine
m    Ectoine
n    2,3-Dimethlypyrazine
o    Amino thiazole
p    Indazole
q    Benzimidazole
r    Urea
s    Ammonium sulfate

| a | Lysis without additive | f | +0.2mM Spermine/min |
| b | +3mM Lysine | g | +0.07mM Spermine |
| c | +1mM Lysine | h | +30mM Imidazole |
| d | +0.33 Lysine | i | +10mM Imidazole |
| e | +0.6 mM spermine | j | +3.3mM Imidazole |
| | | l | | a     Lysis without additive
b     1 mM Arginine
c     30mM 2,3-Dimethylpyrazine
d     15 mM Tryptophane
e     15mM Histidine
f     10mM Indazole
g     15mM Imidazole

| | | | |
|---|---|---|---|
| a | Lysate without additive | g | 15mM Imidazole |
| b | 1 mM Arginine | h | 15 mM Tryptophane |
| c | 30mM Dimethylpyrazine | i | 15mM Histidine |
| d | 15 mM Amino thiazole | j | 5 mM Proline |
| e | 30mM Indazole | k | 30mM Amoniumsulfate |
| f | 15 mM Benzimidazole | | |

FIG. 10a.1

FIG. 10.a.2
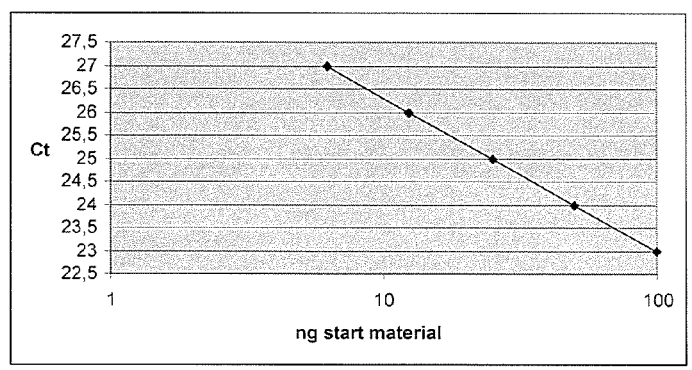
FIG. 11
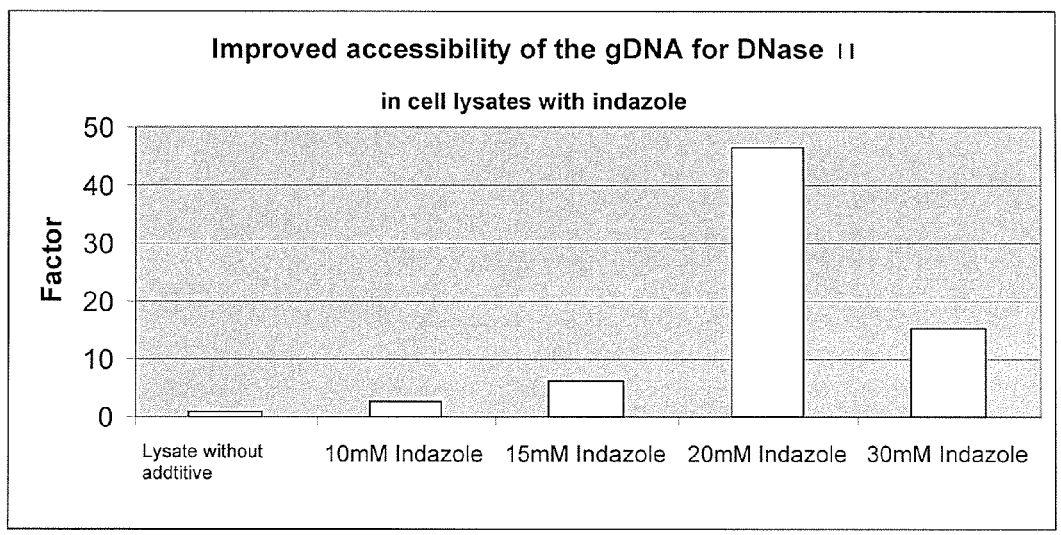

- a  without additive
- b  400mM Spermidine
- c  10 mM Glutamic acid
- d  10 mM Proline
- e  10mM Hisidine
- f  10 mM Glycine
- g  10mM Imidazole
- h  15mM Imidazole
- i  5 mM Arginine
- j  5 mM Urea
- k  15mM Anthranilamide
- l  15mM Pyrimidine a    no
b    30 mM Ammonium sulfate
c    30 mM Glycine
d    30mM Ammonium hydrogen phosphate
e    5 mM Urea a   15 mM Glutamic acid
b   5 mM Arginine
c   15mM 2,3-Dimethyl pryazine
d   15 mM Benzimidazole
e   15mM Imidazole
f   30mM Histidine a   1 mM Arginine
b   3 mM Arginine
c   5 mM Arginine
d   6 mM Arginine a 20 mM Proline
b 20mM Indazole
c 30 mM Ammonium sulfate

METHOD FOR THE TREATMENT OF A SAMPLE CONTAINING BIOMOLECULES

CROSS REFERENCE TO RELATED APPLICATIONS

This application is a divisional of U.S. application Ser. No. 11/910,247, filed Dec. 31, 2007, which was filed under 35 U.S.C. §371 National Stage of PCT/EP06/02961, filed Apr. 1, 2006, which claims priority to German Application 10 2005 015 005.5, filed Apr. 1, 2005, the entire content of which are all incorporated herein by reference in there entireties.

BACKGROUND OF THE INVENTION

1. Field of the Invention

The present invention relates to a method for the treatment of a sample containing biomolecules. The invention further relates to a method for the lysis of a biological sample, a method for the stabilisation of nucleic acids and/or proteins, a method for the reduction of inhibiting effects in a sample containing nucleic acids and/or proteins, a method for the differential masking of nucleic acids and analysis methods which build on the previous methods or incorporate them.

2. Description of Related Art

It has been known for a long time that the genetic origin and the functional activity of a cell can be determined and examined by studies of biomolecules as e.g. its nucleic acids or proteins. The analyses of these molecules enable the direct access to the origin of the activities of cells. They are thereby potentially superior to indirect conventional methods as e.g. the detection of metabolites. This has led to a wide distribution of nucleic acid and protein analyses in previous years. The biomolecular analyses are thus already used in many areas, e.g. in medical and clinical diagnostics, in pharmaceutics in the development and evaluation of drugs, in food analysis and during the supervision of food production, in agriculture during the breeding of agricultural crop and farm animals and in the environment analysis and in many research areas.

The activities of genes can for example be determined directly by the analysis of the RNA, in particular the mRNA in cells. The quantitative analysis of transcript samples (mRNA samples) in cells by modern molecular-biological methods as e.g. real-time reverse transcriptase PCR ("Real-Time RT-PCR") or gene expression chip analyses enables e.g. the recognition of wrongly expressed genes whereby e.g. metabolic disorders, infections or the formation of cancer can be recognised. The analysis of the DNA, e.g. from cells, by molecular biological methods as e.g. PCR, RFLP, AFLP or sequencing enables e.g. the proof of genetic defects or the determination of the HLA-type and other genetic markers.

The analysis of genomic DNA and RNA is also used for the direct detection of infectious agents, such as viruses, bacteria etc.

It is the condition for all analysis methods of biomolecules from biological samples that these biomolecules as e.g. DNA, RNA or proteins are made accessible for the corresponding analysis method. Contents of cells or organisms can usually only be analysed when the contents are present in the analysis medium, that is, are e.g. transferred from the cell or the organism into the analysis medium. The cells/organisms are disintegrated for this purpose, so that the contents are not present within but outside of the organism or the cells and the contents of the organism or the cell are freely accessible for the analysis. The disintegration of organisms or parts of organisms (e.g. cells) is also called lysis, the disintegrated organisms are also called lysates.

The disintegration of samples, e.g. organisms, should take place as completely as possible on two counts: (1) All areas of the sample, e.g. of the organism should be disintegrated, so that the contents of possibly all parts of an organism are released in the sample. (2) The disintegration of the sample, e.g. of the organisms, is only completed when the contents were made accessible for the analysis. While the organisms were disintegrated, but the contents still covered, e.g. by cell compartments, an analysis of the contents cannot be carried out in a quantitative manner.

Presently, several lysis methods are known. A cleaning of the contents to be analysed is followed in the most lysis methods, so as to free the contents from all materials which counteract an analysis. Some examples are to be described in the following:

(A) Lysis with detergents: Detergents are amphipatic molecules which dissolve the hydrophobic membrane of cells so that the contents of the cells outpour into the environment. E.g., non-ionic and ionic detergents belong to these. The detergents triton-X100, Nonidet-P40, sodiumdodecyl sulfate (sodiumdodecyl sulfate, SDS), or also cationic detergents as e.g. N-cetyl-N,N,N-trimethyl-ammonium bromide (CTAB) amongst others have further use for the disintegration of organisms. Many methods with cationic detergents were described and patented for the lysis of organisms and for the isolation of nucleic acids (NA). Nucleic acids can e.g. be complexed by cationic detergents for their protection and cleaning. The methods described in the following US patents and US patent applications are part of these methods: U.S. Pat. No. 6,602,718, U.S. Pat. No. 6,617,170, U.S. Pat. No. 5,010,183, U.S. Pat. No. 5,985,572, U.S. Pat. No. 5,300,635, U.S. Pat. No. 5,728,822, and US 2002/0146677 A1, US 2004/0048384 A1, US 2004/0115689 A1, US 2004/0014703 A1.

The lysis method with ammonium salts as e.g. N-cetyl-N, N,N-trimethyl-ammonium bromide (CTAB) use amphipatic ammonium salts which contain a longer hydrocarbon chain of at least 6 C atoms.

B) Lysis with water: During the lysis with water, the properties of semipermeable membranes of cells are used which envelope these. These membranes are water-permeable, but not for salts or larger molecules. If a cell with its contents of salt and other larger molecules is transferred into a fluid, which contains a lower salt concentration than the cell interior, the cell will absorb water until the salt concentration within and outside the cell is balanced. If the concentration difference between the cell interior and the outer fluid is sufficiently large, the cell will absorb water until it bursts.

C) Lysis with organic solvents: the hydrophobic membranes of cells can be destroyed by organic solvent. The lipids of the membranes and the lipophilic protein components of the membranes are hereby absorbed in the organic phase. The cell contents remain mostly in the hydrophilic phase or at the boundary layer between the lipophilic and the hydrophilic phase. Phenol is often used with this type of lysis.

D) Lysis with chaotropic salts: chaotropic salts destroy the structure of water based on the formation of hydrogen bridge bonds, so that the double layer structure of membranes cannot be maintained anymore. These membranes are thereby dissolved and the lysis takes place, whereby the cell contents pour into the chaotropic environment. This method is used with a number of methods for isolating nucleic acids and proteins, e.g. in the commercially available RNeasy®-, QIAamp®—methods or the denaturating disintegration of cells for protein cleaning.

It is desirable for the following cleaning steps or detection reactions which are carried out with the obtained lysate that the relevant contents of the cell are transferred as completely as possible into the lysate, as the amount which is necessary for the detection or for the isolation of a given amount of a biomolecule such as DNA or RNA, can be reduced further.

With the quantitative and the qualitative analysis of biomolecules as e.g. nucleic acids and proteins, the preservation of their integrity is of great importance. In particular nucleic acid such as DNA and, to a higher extent, RNA are subject to different influences after the removal of the biological samples from their natural environment, which can lead to a change or degradation of the DNA or RNA. For example, the enzymatic degradation of these nucleic acids or the degradation of DNA under the influence of shear forces occurring in the sample during the lysis are mentioned.

It is known that the preservation of the integrity of nucleic acids and proteins can be achieved by (A) cleaning of the NA or proteins, (B) dehydration, (C) protection against degrading enzymes or (D) complexing. This is described shortly in the following:

(A) Cleaning of the nucleic acids or proteins: during the cleaning, nucleic acids or proteins are freed from all substances or molecules which are contained in the biological sample and which can damage the integrity of the nucleic acids or the proteins permanently. These cleaning methods are e.g. affinity chromatography, protein salting out methods, cleaning of nucleic acids or proteins at solid phases. The solid phase can e.g. be an ion exchanger as is described in U.S. Pat. No. 5,990,301, and U.S. Pat. No. 6,020,186 for example. Alternatively, the use of porous matrices is described, e.g. in U.S. Pat. No. 6,180,778 or U.S. Pat. No. 5,496,562.

(B) Dehydration: a dehydration of the nucleic acid or proteins causes that damaging processes, which can take place when the sample with the nucleic acids or proteins are dissolved in water, are blocked or prevented. These damaging processes are e.g. the enzymatic degradation by proteases or nucleases. Thus, the isolated nucleic acid can be dehydrated e.g. by precipitation (precipitation) by means of salt and alcohol (Current protocols in molecular biology, e.g. p. 1.6.1. Alkaline Lysis Miniprep). Nucleic acids can also be protected from degradation in biological samples as e.g. in tissue parts or microscopic sections by dehydration. This is described in the U.S. Pat. No. 6,528,641 for example. The reagents are infiltrated into the intact sample in the method described there, whereby not only a dehydration, but also a precipitation of proteins as e.g. nucleases is effected, which are then present in the dehydrated sample in an inactive manner. The use of ammonium sulfate as dehydrating agent is particularly described there. A precipitation of DNA is also effected in the cleaning of DNA described in the patent application US 2002/0197637, whereby polyamines are used for cleaning and the polyamines lead to a condensation of the DNA, whereby a damage of the DNA by shearing shall be avoided with mechanical disintegration.

(C) Protection from degrading enzymes: it has been known for a long time that proteases and nucleases (enzymes disintegrating nucleic acid) can be specifically inhibited. Thus, the DNase I can be inhibited by e.g. $Mg^{2+}$- or $Ca^{2+}$-complexing agents. RNases can be inhibited e.g. by specific RNase inhibitors or by reducing agents. These inhibitors are described in the U.S. Pat. No. 5,552,302 and U.S. Pat. No. 6,777,210.

(D) Complexing: Another variant of the cleaning provides a complexation with quaternay ammonium salts forming micelles for the protection of the nucleic acids. The complexing of the nucleic acids thus leads to the protection from nucleases. Quaternary ammonium salts are used thereby, which function as cationic detergents and form micelles. For this it is necessary that the quaternary ammonium salt has at least one long-chain carbon chain as substituent. The U.S. Pat. No. 6,602,718, U.S. Pat. No. 6,617,170, U.S. Pat. No. 5,010,183, U.S. Pat. No. 5,985,572, U.S. Pat. No. 5,300,635, U.S. Pat. No. 5,728,822 and the US patent applications US 2002/0146677A1, US 2004/0048384A1, US 2004/0115689, and US 2004/0014703A1 are counted amongst these or similar methods.

U.S. Pat. No. 6,821,752 describes a cleaning and extraction of proteins in the presence of amphipatic amines, that is, of compounds acting as detergents in a similar manner.

The compounds provided for the separation or complexation of the nucleic acids or proteins is restricted in that they should behave as inert as possible with regard to the isolation method or analysis method carried out subsequently, that is, should not influence the subsequent isolation or analysis in a disadvantageous manner. Otherwise, they have to be decomplexed in a further reconditioning step.

The above state of the art shows that sufficient stabilisation of nucleic acids and proteins from biological samples usually requires additional reconditioning steps by which the sample is split. Methods for the stabilisation which make these additional reconditioning steps unnecessary and which use stabilising reagents which can be used as versatile as possible, are therefore advantageous.

A further problem which can occur with the analysis of biomolecules such as nucleic acids or samples containing proteins, is the fact that biomolecules of a first type can be impaired by biomolecules of a second type in such a sample. Sometimes, biomolecules of the second types shall also be analysed, whereby biomolecules of the first or another type will then act in a disrupting manner during the analysis. An example amongst many is mentioned here to clarify this: A sample contains cells of a certain organism. A detection of a nucleic acid of these cells by an oligonucleotide in the presence of proteins binding nucleic acid can for example be influenced in a disadvantageous manner. Assuming that a certain species of DNA is to be detected in the present example, the proteins binding the DNA represent an inhibiting substance. In another example, e.g. the analysis of proteins binding DNA, a DNA which can bind to the proteins binding DNA can have a disadvantageous influence on the result of the analysis, as the nucleic acid acts as inhibiting substance in this case and leads to a falsification of the results of the analysis.

Usual methods for excluding these disadvantageous interactions between different biomolecules provide to separate the biomolecules which are influencing each other to avoid disturbances. These methods thus often provide a cleaning step, in which certain species of biomolecules are removed from a sample. The concentration of the biomolecules amongst themselves is thereby changed by the separation method, so that the desired biomolecules are enriched, but the other ones are reduced in their concentrations.

Known methods for the separation of biomolecules include the following methods:

(A) Separation of biomolecules by salting out methods: Salting out methods are used to separate parts of the biological sample which can be precipitated by a certain amount of salts from the sample. These methods can be used on the one hand to precipitate the part to be cleaned with salt. The ammonium sulfate precipitation of proteins represents such a known method. On the other hand, this method can also be used in the reverse direction, so that the material to be cleaned is freed from a plurality of contaminating molecules, but is not precipitated itself. An example for this is the protein precipitation by potassium acetate during the isolation of DNA.

(B) Separation of biomolecules by chromatography: Biomolecules can, due to their properties, be cleaned and separated by several chromatography methods. These properties can concern their size, their charge, their hydrophobity or their affinity to certain surfaces or haptenes, to mention only a few possibilities. Chromatography is to be explained here with the example of the ion exchange chromatography: There are two possibilities for a series of chemical biomolecules to be cleaned by ion exchange chromatography. The biomolecule to be isolated can on the one hand be bound to the ion exchange chromatography material, whereas the contaminating substances are not bound and can be separated from the biomolecule to be isolated in this manner (e.g. anion exchange chromatography for the cleaning of negatively charged nucleic acids). On the other hand, contaminating substances can also be bound to the chromatography material, and the biomolecule to be isolated can then be caught in the break-through or in the washing buffer (e.g. cation exchange chromatography for the cleaning of the negatively charged nucleic acids). Examples of such a method are described in U.S. Pat. No. 5,990,301 and WO0248164.

(C) Separation of biomolecules at solid surfaces: A number of surfaces have the property to be able to bind certain biomolecules in a defined binding environment. Theses binding properties can be used for the cleaning of biomolecules. This will be explained here with the example of the cleaning of nucleic acid at silica surfaces. Silica surfaces, be it microparticles or membranes, can bind nucleic acids in the presence of chaotropic salts having a high concentration. But other molecules as e.g. proteins do not bind to these surfaces and are thus separated. The nucleic acid can be obtained in a pure form after the washing of the silica surface. Examples for this are described in the U.S. Pat. No. 5,990,301, U.S. Pat. No. 6,020,186 and U.S. Pat. No. 6,180,778.

(D) Separation of biomolecules by selective complexing: Some separation methods complex biomolecules selectively, so that these can be separated from the other contents of the sample by a centrifugation step or by a filtration step. Examples for this are described in U.S. Pat. No. 5,728,822 and U.S. Pat. No. 5,985,572.

The use of ammonium sulfate for the neutralisation of inhibiting effects at samples containing RNA is described in the US patent application US 2002/0115851. These samples contain purified amounts of RNA. However, it is described in the literature that inorganic ammonium salts as e.g. ammonium sulfate have the disadvantage that certain partial activities of polymerases (e.g. 3'-5' exonuclease activity) can be changed and the presence of ammonium sulfate can thereby have a disadvantageous effect on the polymerase reactions carried out for the subsequent analysis (Tsurumi et al., "Functional Expression and Characterization of the Epstein-Barr Virus DNA Polymerase Catalytic Subunit", Journal of Virology, Vol 67, No. 8, 1993, p. 4651-4658)

The described methods require a preceding separation of the biomolecules affecting the detection reaction in a disadvantageous manner from the sample or presume these. Consequently, a need exists for a simplified method with which the inhibiting effect of certain biomolecules in samples can be removed in such a measure that a reliable detection reaction can be carried out with the sample.

A further problem which often occurs during the separation of nucleic acids, is founded in the fact that ribonucleic acid (RNA) and deoxyribonucleic acid (DNA) represent biomolecules which are very similar in their chemical properties. Thus, there is often the difficulty to separate these from each other. For a plurality of applications, it is nevertheless of utmost importance to produce DNA-free RNA or RNA-free DNA: contaminating genomic DNA in RNA preparations can for example lead to quantitatively wrong results in RT-PCR experiments.

At present, a number of methods exist which make it possible to enrich RNA or DNA differentially. Different methods can be distinguished in principal:

On the one hand, enzymes can be used which specifically degrade DNA or RNA. These enzymes are called nucleases. The RNA-degrading enzymes belong to these nucleases, the RNases, and the DNA-degrading enzymes, the DNases. If e.g. DNA is to be cleaned, a RNase can be used during the cleaning method, which decomposes the RNA molecules into small fractions. These methods are generally used for e.g. plasmid isolation or cleaning of genomic DNA. DNA contaminations in RNA preparations are alternatively hydrolysed with DNase I. This method is also generally known.

On the other hand, chemical methods can be used which utilise the differences in the chemical properties of RNA or DNA. A number of solid phase cleaning methods are counted amongst these. The solid phase can e.g. be an ion exchanger, as for example described in U.S. Pat. No. 5,990,301 and U.S. Pat. No. 6,020,186, or it can be a porous matrix, as is described in e.g. U.S. Pat. No. 6,180,778 and U.S. Pat. No. 5,496,562.

Other cleaning methods concern the different solubility behaviours of RNA or DNA. The cleaning of RNA in the presence of aqueous solution of a chaotropic salt and acidic phenol is counted amongst these, whereby genomic DNA enriches in the inter phase and RNA remains in aqueous solution (Chomczynski P. & Sacchi N., 1987, Anal Biochem. 1987 April; 162(1):156-9, "Single-step method of RNA isolation by acid guanidinium thiocyanate-phenol-chloroform extraction").

Other methods are based on the selective precipitation of RNA or DNA. Examples for this have already been described above in connection with the decomplexing of inhibiting biomolecules or the stabilisation of biomolecules.

These methods also include a separate method step, with which the relative composition of the different biomolecules, in particular different nucleic acids or proteins is changed considerably to achieve the desired effect. The practicability of the method can depend if the reagant used for the separation has a negative effect on the desired detection reaction, whereby the number of reagents available for a certain sample preparation as e.g. for an analysis method is restricted. Every method step for the separation of a sample also has a contamination risk in addition to the additional costs, which makes an extremely clean and controlled operation necessary.

With regard to different aspects, there is thus a need for a further improvement of the sample preparation of samples containing biomolecules and improved processing, preparation, and analysis methods of biomolecules.

SUMMARY OF THE INVENTION

The present invention solves this object with a method for the sample preparation for a successive preparation, processing or analysis method, a method for the lysis of a biological sample, an analysis method, a method for stabilisation of nucleic acids and/or proteins, a method for the reduction of inhibiting effects in a sample, the analysis method, a method for the selective masking, and a differential analysis method as described in the following Specification.

Further advantageous aspects, details and characteristics of the present invention result from the description, the examples, and the figures.

Before the individual aspects of the present invention are described, the following terms are explained in the following, as they are understood in the present invention.

Organisms: Organisms are defined as any form of casings containing nucleic acids and/or proteins. These include e.g. viruses, phages, cells, cell formations or entire organisms. These organisms can be used live, dead or in their resting state. These organisms can be in solution, pelleted, or can also be associated with solid phases or bound. When "organisms" is mentioned within the scope of the present invention, it could be several organisms of the same type, several organisms of a different type, or also a single organism. The organisms can be founded on archaebacteria, procaryonts or eucaryonts. They can have animal, vegetable or endosymbiontic (e.g. also mitochondria or plasides) origin. Amongst the organisms in the sense of the present invention are e.g. individual cells, cell assemblies, tissue or whole animals or whole plants, cultivated cells, excretion products or secretions, e.g. stabilised and non-stabilised blood, serum, plasma, tissue fluids, sperm, swabs, sputum, saliva, tear fluid, urine, excrements, hair or hair roots, hair dandruff, buccal swabs, buffy coat, etc.

Cellular substance: Cellular substance within the scope of the present invention is a heterogenous material mixture which occurs within organisms or which can be delivered into the environment, as e.g. tissue fluids, plasma, saliva, sputum, secretions etc. The cellular substance contains cell contents as e.g. nucleic acids, proteins and other polymers and metabolites. The substances to be assigned to the casing of the organism also belong to these, as e.g. casings, in particular membranes, capsides, cell walls, extra-cellular matrices etc.

Biomolecules: Biomolecules are molecules which originate from organisms or their conversion products obtained in line with a detection method as e.g. by an amplification. Biomolecules are e.g. nucleic acid or proteins or other molecules from organisms. The biomolecules can be obtained by e.g. the lysis of organisms.

Nucleic acid: Nucleic acid (NA) is conceived to be deoxyribonucleic acid (DNA), ribonucleic acid (RNA) or peptide nucleic acid (PNA) within the scope of the present invention. Deoxyribonucleic acid (DNA) and ribonucleic acid (RNA) occur naturally in organisms, but they can also occur outside of organisms or could have been added to these. The length of the nucleic acid can be different. The nucleic acid can be modified by changes. E.g., one or more of the nucleobases of the nucleic acid can be modified. Even the sugar units in the nucleic acid can be modified (e.g. by methoxy groups) or even replaced, as for example in PNA. The nucleic acid can contain base analogons as e.g. non-purine or non-pyrimidine analogons or nucleotide analogons as e.g. PNA. The DNA and/or RNA can contain addenda as e.g. proteins or amino acids. The term DNA, as understood in the present inventions, can be further sudivided into types occurring naturally and types not occurring naturally, whereby types not occurring naturally can also enter organisms (for example by transfection or transformation). Genomic DNA (gDNA) contains the sequence information which contains the design of the organism. Partial regions, also very small partial regions from this sequence are called genomic DNA, which do not correspond to the entire sequence in line with the present invention. Genomic DNA are also their modified forms as understood in line with the present invention. The term "DNA" also includes plasmid DNA. Plasmid DNA is an extra-chromosomal DNA with an own "origin of replication". Plasmid DNA are also their modified forms as understood in line with the present invention. The term "DNA", as understood here, also includes mtDNA or ptDNA. mtDNA or ptDNA is the genomic DNA from mitochondria or plastides. mtDNA or ptDNA are also their modified forms as understood here.

The term "RNA", as understood here, includes the naturally occurring and not naturally occurring types, whereby not naturally occurring types can enter organisms (e.g. by transfection). mRNA, hnRNA and rRNA are large RNA molecules (50 nt to many kb), which can be produced as a copy from a coded region. mRNA or rRNA are also their modified forms as understood in line with the present invention.

tRNA, miRNA, siRNA etc. are small RNA molecules, which are effective during the translation. Every amino acid (AS) which is connected to further amino acids via a peptide connection in a linear or also a branched arrangement is called protein. The protein can occur as monomer, dimer or multimer, whereby homomers or heteromers can be formed. Proteins can be naturally occurring proteins or can be synthetic proteins. The proteins can be present in a modified form. These proteins can be e.g. enzymes, structural proteins, receptors, ion channels and other transporters, extracellular matrix proteins, transcription regulators, proteins binding nucleic acid, casing and protection proteins, storage proteins etc.

Lysis: The term "lysis" is a process in line with the present invention which results in that nucleic acids and/or proteins are passed from organisms into the environment. The structure of the organisms can thereby be destroyed, e.g. the casing of the organism can be dissolved. With the term "lysis" is also understood, in line with the present invention, that cellular substances can exit from the organisms through small openings, e.g. pores etc. in the casing of the organism without destructing the structure of the organisms. Pores can for example be produced by lysis reagents. Furthermore, the term "lysis" in line with the present invention means that nucleic acids and/or proteins of organisms, which already appear to be structurally destroyed or which have small openings, can be flushed out by the use of an additive. A lysate is produced by the lysis. The process of the lysis can take place by means of enzymatic, chemical or physical lysis methods.

Enzymatic, chemical or physical lysis methods: The term "enzymatic lysis method" in line with the invention is a process which supports the lysis of organisms or the release of biomolecules by means of enzymes. That is, the enzymes for enzymatic lysis methods are characterised in that it supports a lysis of organisms or a release of biomolecules. Such enzymes are e.g. proteases, lysozymes, glucanases, peptidases, lipases, hyaluronidases, collagenases, nucleases, amylases, hydrolases, pectinases, etc. The specialised expert knows of more enzymes, which support a lysis of organisms or a release of biomolecules in the sense of the present invention. These enzymes can be obtained in a classic manner from organisms or by biotechnological methods. These enzymes are also genetically or chemically changed enzymes, and heat-unstable or heat-stable enzymes.

The term "chemical lysis method" in line with the invention is a process which supports the lysis of organisms or the release of biomolecules by means of chemicals. These are e.g. detergents, acid, base, organic solvents, chaotropic substances etc.

The term "physical lysis method" in line with the invention is a process which supports the lysis of organisms or the release of biomolecules by means of physical methods. These are mechanical, thermal, but also those methods which are based on the effect of waves and pressure differences.

Mechanical lysis methods are e.g. methods which cause a shearing or a comminution as e.g. mills, knives, small canulas, sieves, mortars, or impingement with particles or methods which can lead to a homogenisation of the sample. With the thermal lysis method, a temperature change leads to the degradation of organisms or the release of biomolecules. These can e.g. be based on heating or cooling, e.g. under the freezing point. Methods based on the effect of waves are e.g. treatments with sound or electromagnetic waves. Pressure changes can also support the lysis, as e.g. in the form of squeezing or sudden pressure changes (e.g. French press).

The specialised expert is aware of further enzymatic, chemical or physical lysis methods and it is also known that these methods can be used in different combinations.

Lysis buffer: The term "lysis buffer" is generally a fluid used for the lysis in line with the present invention. This fluid can be a solution of different lysis reagents. The lysis buffer can, but does not have to comprise a buffer system for adjusting the pH. The fluid compositions used in the method according to the invention represent e.g. "lysis buffers".

Reaction system: A reaction system in line with the present invention is to be understood every form of the system, with which a component which is contained in a sample can be modified, identified or changed in a biological, chemical or physical reaction. The reaction system contains at least a detectable amount of the component to be analysed, e.g. DNA and/or RNA.

Differential analysis: The differential analysis is a reaction system, in which a sample is used, in which at least two different components, e.g. the nucleic acids DNA and RNA are contained, and in which at least one of the components, e.g. one of the above-mentioned nucleic acids is not to be analysed.

Nucleic acid preparations or protein preparations: nucleic acid preparations are nucleic acids which were obtained by the preparation of a sample containing nucleic acid or a mixture of materials containing nucleic acid, whereby the preparation represents a method with which the relative concentration of different nucleic acid or protein species contained in the sample or in the mixture of materials is influenced, so that one or more determined species of nucleic acid were enriched in the nucleic acid preparation. Amongst the preparation methods thereby are e.g. purification methods as e.g. the cleaning of nucleic acids from a sample via a silica membrane (e.g. Rneasy or QIAamp®, obtained from the company QIAGEN GmbH, Hilden, Germany), whereby the concentration of proteins with regard to the nucleic acid compared to the sample of the mixture of materials considerably declines before the preparation method. An analogon applies to the protein preparation.

In the following, different nucleic acid hybridisation or sequencing and synthesis methods are described, as they can be used in line with the analysis method according to the invention. These methods are standard methods, as for example described in the applications WO 01/498802 or US 2002/0115851.

Binding reactions: A binding reaction is a reaction in which at least two binding partners (e.g. two nucleic acid molecules in a hybridisation or two proteins in an antibody antigen interaction or protein and nucleic acid in a binding reaction) interact with one another. Binding reactions are carried out to execute the detection reactions or quantification or to prepare this.

A sample is contacted with a probe, so that the sample can be bound by the probe. The probe can be modified in such a manner that a simple detection of the probe is possible. These modifications can e.g. be couplings of fluorophores, radioactive substances or enzymes.

The nucleic acid first strand is the nucleic acid strand which is formed during the primer-dependent nucleic acid synthesis by an enzyme, as e.g. DNA or RNA polymerase, ligase etc., and which is complementary to a target nucleic acid. The nucleic acid secondary strand is the nucleic acid strand which is formed during the primer-dependent nucleic acid synthesis by an enzyme and is complementary to the sequence of the first strand.

A nucleic acid which reacts in a reaction system, e.g. specifically binds a defined primer or oligonucleotide, that is, can hybridise with this, is seen as a target nucleic acid. The target nucleic acid serves in this example as matrice of the nucleic acid strand to be synthesised after the primer binding with the primer-dependent nucleic synthesis by an enzyme, e.g. DNA- or RNA-dependent DNA polymerises, whereby the sequence of the nucleic acid strand to be synthesised is complementary to the sequence of the target nucleic acid. Specific binding does thereby not mean that 100% of complementing has to be present between the target nucleic acid and the hybridising part of the primer or oligonucleotide. Up to a maximum of 50% of the bases in the hybridising region between primer and target nucleic acid are not allowed to be complementary, so as to achieve useful results. Good up to very good results can be achieved when no more than 30% of the bases of the hybridising part of the primer and the target nucleic acid are not complementary. The higher the degree of complementing between the hybridising part of the primer and the target nucleic acid, the more specific and effective is the primer.

On one hand, the target sequence is the sequence containing the primer binding location, and on the other hand the sequence which is in the 3' direction (downstream) of the primer binding location. A nucleic acid sequence is formed at the primer-dependent nucleic acid synthesis, which is complementary to the target sequence.

Primers are starters for the nucleic acid synthesis. These are mostly short-chained, single strand oligoribo- or oligodeoxyribonucleotides which are complementary to a region of one single strand nucleic acid molecule (see above) and can react with this to a double strand. The free 3' hydroxy end in this double strand serves as a substrate for nucleic acid polymerases, as for example DNA polymerases, and as starting point for the polymerisation of the entire single strand to a double strand. Primers are generally defined as an oligomeric starter molecule, which can bind sequentially to the target nucleic acid. The sequence of the target nucleic acid which binds the primer, is called primer binding location. A primer can thereby also bind different target nucleic acids, when these all contain the same or a similar sequence as primer binding location. A first or primary primer P1 is defined as "anti-sense primer" and a second or secondary primer P2 as "sense primer".

A "sense primer" which is either a secondary primer P2 added to the reaction from outside or a primer formed by the backfolding of the nucleic acid first strand (so-called "hairpin loop") is understood to be a secondary strand synthesis primer.

A primer binding location is the sequence of the target nucleic acid which can bind the primer by hybridisation. The sequence of the primer binding location is at least up to 30%, preferably at least 50%, particularly preferably 100% complementary to the sequence of the primer.

The hybridising part of the primer is the sequence part of the primer which hybridises to the primary target molecule and which is complementary to the sequence of the primer binding location of the primer target molecule in at least 50% of the bases. The primary target molecule is the nucleic acid molecule that is introduced into the enzymatic reaction. It is not a product of this reaction.

The primer-dependent nucleic acid synthesis catalysed by enzymes, as particularly DNA and RNA dependent DNA polymerases is a key reaction with the cDNA synthesis, DNA sequencing and with application methods as e.g. the polymerase chain reaction (PCR)/RT-PCR or the isothermal amplification methods NASBA (nucleic acid sequence based amplification), 3SR (self-sustained sequence replication; contains the use of RNase H), 2SR (self-sustained sequence replication; similar to 3SR, but without the use of RNase H), TMA (transcription mediated amplification), SDA (strand displacement amplification), LCR (ligase chain reaction) and related methods. The efficiency of the primer-dependent nucleic acid synthesis is influenced by the activity of the enzyme for the nucleic acid polymerisation (e.g a DNA polymerase), by the target nucleic acid and by the efficiency and specificity of the primer hybridisation. In the following, some application examples for primer-dependent nucleic acid synthesis processes are described in more detail.

Primer-dependent nucleic acid synthesis reactions can be found e.g. in the first and secondary strand cDNA syntheses, the DNA sequencing, mutagene processes based on primer binding and other methods. Sequence-specifically started nucleic acid synthesis reactions are thereby carried out using enzymes, as e.g. RNA- or DNA-dependent polymerases, whereby the sequence-specifically started DNA synthesis reactions contain the following steps:
1. Sequence-specific hybridisation of a first primer P1 to one sequence of the target nucleic acid (RNA or DNA) complementary to this; and 2. extension of the primer P1 by the catalytic insert of deoxyribonnucleotides to the free 3'-OH end of the primer P1 to be extended by means of an enzyme as e.g. a RNA-dependent or DNA-dependent DNA polymerase, whereby the target nucleic acid serves as a matrice, and the primer P1 altogether, or at least in the 3'-region, contains a sequence which is complementary to a certain sequence of the target nucleic acid and can hybridise at this target-sequence in a sequence-specific manner, and whereby the primer P1 can contain a sequence in the 5'-region which is not complementary to the target nucleic acid and which cannot hybridise at the target nucleic acid and can contain additional functions. The synthesis runs to the end of the target nucleic acid (matrice) or can be interrupted before the end, whereby the first strand nucleic acid synthesis is ended.
3. The nucleic acid secondary strand synthesis starts through the sequence-specific hybridisation of a secondary strand synthesis primer (ZP). The secondary strand synthesis primer can be a separate primer P2 introduced into the reaction, a degradation product of the target nucleic acid, or a primer (hairpin loop) formed by the backfolding of the nucleic acid first strand.
4. Extension of the ZP by the catalysed integration of nucleotides to the free 3'-OH end of the ZP to be extended by means of an enzyme, whereby the nucleic acid first strand of the target nucleic acid serves as matrice; the ZP contains, altogether, or at least in the 3'-region, a sequence which is complementary to a certain sequence of the target nucleic acid and which can hybridise at this in a sequence-specific manner, and the ZP can contain a sequence in the 5'-region which is not complementary to the target nucleic acid, and cannot hybridise at the target nucleic acid as a consequence thereof or can comprise a sequence different to the primer P1.

The primer-dependent synthesis reaction is a key reaction, even with the sequencing. The method of the nucleic acid sequencing essentially follows the method described previously under primer-dependent nucleic acid synthesis reaction and is limited to the steps (1) and (2), whereby, in the case of a DNA synthesis, a mixture of deoxyribonucleotides and dideoxyribonucleotides is used for the catalytic integration by enzymes, as e.g. RNA- or DNA-dependent polymerases.

The sequence-specifically started nucleic acid synthesis reactions are thereby carried out for the sequencing by enzymes, as for example RNA- or DNA-dependent DNA-polymerases, whereby the sequence-specifically started DNA sequence reactions contain the following steps:
1. sequence-specific hybridisation of a primer P1 to a sequence of the target nucleic acid (RNA or DNA) complementary to this.
2. extension of the primer P1 by the catalysed integration of deoxyribonucleotides and dideoxyribonucleotides to the free 3'-OH end of the primer P1 to be extended by an enzyme, e.g. a RNA-dependent or DNA-dependent DNA polymerase, whereby the target nucleic acid serves as a matrice, and the primer P1 contains, altogether, or at least in the 3'-region, a sequence which is complementary to a certain sequence of the target nucleic acid and can hybridise to this target sequence in a sequence-specific manner, and whereby the primer P1 can contain a sequence in the 5'-region which is not complementary to the target nucleic acid and which cannot hybridise at the target nucleic acid and can contain additional functions.

Primer-dependent nucleic acid synthesis reactions are also found at first and secondary strand DNA syntheses of the polymerase chain reaction (PCR). The sequence-specifically started DNA synthesis reactions are thereby carried out by heat-stable RNA- and/or DNA-dependent DNA-polymerases, whereby the sequence-specifically started DNA sequence reactions contain the following steps:
1. initial thermal denaturing of the target nucleic acid;
2. sequence-specific hybridisation of two primers P1 and P2 to a sequence of the target nucleic acid complementary to this;
3. extension of the primers P1 and P2 by the catalysed integration of deoxyribonucleotides to the free 3'-OH end of the primers P1 and P2 to be extended by a heat-stable RNA-dependent or DNA-dependent DNA polymerase, whereby the target nucleic acid serves as matrice;
4. the primer extension products on their part serve again as matrice for the primer hybridisation of the primers P1 and P2 after entry into step (1); and 5. the steps (1) to (4) can be repeated arbitrarily, and the nucleic acid with the desired properties can thus be synthesised, whereby the primers P1 and P2 contain, altogether, or at least in the 3'-region, a sequence which is complementary to a certain sequence of the target nucleic acid and can hybridise to this target sequence in a sequence-specific manner, and whereby the primers P1 and P2 can contain a sequence in the 5'-region which is not complementary to the target nucleic acid and which cannot hybridise at the target nucleic acid and can contain additional functions.

Sequence-specifically started nucleic acid synthesis reactions are further components of isothermal, exponential nucleic acid amplification methods based on in-vitro transcription as e.g. NASBA (nucleic acid sequence based amplification), 3SR (self-sustained sequence replication), 2SR (self-sustained sequence replication similar to 3SR, but without use of RNase H), TMA (transcription-mediated amplification), and similar methods. With these methods, primers are used, RNA- and DNA-dependent DNA polymerases and suitable reaction conditions, whereby the exponential nucleic acid amplification methods comprise the following steps:
1. production of a single reaction medium, which contains a target nucleic acid, a first primer P1, a second ZP, an RNA-dependent DNA polymerase, a DNA-dependent DNA polymerase, a DNA-dependent RNA polymerase, ribonucleotides and deoxyribonucleotides;
2. setting reaction conditions, so that amplification cycles can be maintained, whereby
3. the first strand synthesis is carried out complementary to the target nucleic acid by the hybridisation of a primer P1 to a complementary target sequence, followed by an extension of the primer P1 by deoxyribonucleotides using a RNA- or DNA-dependent DNA polymerase, whereby the target nucleic acid can be either a DNA or a RNA, and
4. the synthesis of the secondary strand DNA is carried out complementary to the first strand DNA by the enzymatic, thermal or chemical denaturing or degradation of the target nucleic acid of the first strand DNA and the hybridisation of a ZP to the complementary first strand DNA, followed by an extension of the ZP by deoxyribonucleotides using a RNA- or DNA-dependent DNA polymerase, whereby the primers P1 and ZP contain, in the 3'-region, a sequence which is complementary to a certain sequence of the target nucleic acid and can hybridise at this target sequence in a sequence-specific manner, and whereby at least one of the primers P1 or ZP or both primers contain a sequence in the 5'-region which is not complementary to the target nucleic acid and which cannot hybridise at the target nucleic acid and contains a DNA-dependent RNA polymerase promoter sequence,
5. from which can be carried out an in-vitro transcription of the DNA molecule synthesised in steps (1) to (4) using DNA-dependent RNA polymerase and ribonucleotides, whereby the generated in-vitro transcripts again serve as matrice and again enter DNA first and secondary synthesis under sequence-specific hybridisation of primer P1 and ZP, followed by in-vitro transcription. An exponential amplification of the nucleic acid is achieved in this manner.

Sequence-specifically started nucleic acid synthesis reactions are further components of linaer, isothermal nucleic acid amplification methods based on in-vitro transcription. These methods are carried out using sequence-specifically binding primers, RNA- and DNA-dependent DNA polymerases and RNA polymerases with suitable reaction conditions, whereby the isothermal, linear nucleic acid amplification methods comprise the following steps:
1. production of a single reaction medium, which contains a target nucleic acid, a first primer P1, a second ZP, a RNA-dependent DNA polymerase, a DNA-dependent DNA polymerase, a DNA-dependent RNA polymerase, ribonucleotides and deoxyribonucleotides.
2. carrying out the first strand synthesis complementary to the target nucleic acid by the hybridisation of a primer P1 to a complementary target sequence, followed by an extension of the primer P1 by deoxyribonucleotides using a RNA- or DNA-dependent DNA polymerase, whereby the target nucleic acid can be either a DNA or a RNA;
3. carrying out the synthesis of the secondary strand DNA complementary to the first strand DNA, by the enzymatic, thermal or chemical removal of the target nucleic acid from the first strand DNA and the hybridisation of a ZP to the complementary DNA of the first strand. The nucleic acid secondary synthesis begins by the sequence-specific hybridisation of a second ZP, a degradation product of the target nucleic acid or by the backfolding of the nucleic acid first strand to the sequence of the nucleic acid first strand of the target nucleic acid complementary to this. An extension of the ZP by deoxyribonucleotides follows with the use of a RNA- or DNA-dependent DNA-polymerase, whereby the primers P1 and ZP contain, in the 3'-region, a sequence which is complementary to a certain sequence of the target nucleic acid and can hybridise to this target sequence in a sequence-specific manner, and whereby at least one of the primers P1 or ZP or both primers contain a sequence in the 5'-region which is not complementary to the target nucleic acid and which cannot hybridise to the target nucleic acid and contains a DNA-dependent RNA polymerase promoter sequence, from which can be carried out an in-vitro transcription of the DNA molecule synthesised in steps (1) to (3) by the use of DNA-dependent RNA polymerase and ribonucleotides. A linear amplification of the nucleic acid is achieved in this manner.

Strand Displacement Amplification (SDA): SDA is a generic term for a number of methods which lead to the amplification of nucleic acid. The reactions contain at least the nucleic acid to be amplified, a suitable buffer, primer, dNTPs and a polymerase. The reaction leads to a nucleic acid synthesis, whereby a double-strand is freed to be able to use a single strand generated in that manner as matrice. The freeing can be carried out by the polymerase itself (original SDA). The freeing of the double strand can alternatively be carried out by means of a helicase (helicase-dependent amplification) If primers are used which comprise chance sequence, the reaction is called multiple displacement amplification (MDA). A method was developed by VanNess, in which the primers originate from first strand breaks of the target nucleic acid to be amplified (US patent application 2003/138800, "Exponential amplification of nucleic acids using nicking agents"). A method was developed by the company NUGen (USA), where RND/DNA fusion primers are used. Another SDA reaction uses circular DNA for the amplification (rolling circle amplification). DNA is synthesised hereby. A similar method amplifies RNA (rolling transcription amplification).

Primer-independent synthesis reactions: Primer-independent synthesis reactions are reactions which do not need a primer. An example of a primer-independent synthesis reaction is the transcription reaction. With a transcription reaction is synthesised a transcript, starting from a gene which contains a suitable promoter for a RNA polymerase, in the presence of nucleotides, a suitable reaction environment and RNA polymerase. This takes place without the use of a primer. A number of transcripts are read from a gene and synthesised.

A further example for a primer-independent synthesis reaction is the translation reaction. Here, a RNA transcript is brought into contact with a translation apparatus. This consists of ribosomes and all further components which are necessary to produce proteins or polypeptides. Amongst these are e.g. tRNAs, aminoacyl-tRNA-synthetases etc. If a transcript is brought into contact with this reaction solution, proteins can be produced by means of this primer-independent reaction.

In the following, further reaction systems are described, as they can be used in line with the analysis method according to the invention.

Enzymatic tests are reaction systems, in which catalytically effective biomolecules can be measured with the help of their catalytic activity. Amongst these are e.g. tests of enzymes such as dehydrogenases, hydrolases, polymerases, phosphorylases, phosphatases, kinases, etc.

Use of surfaces of biomolecules: This is understood to be a quantification, detection, enrichment or depletion of biomolecules using the specific characteristics of their surface. Amongst these are e.g. detections of biomolecules with the help of antibodies, aptameres or binding partners, cofactors, proteins of multienzyme complexes or also protein or nucleic acid for detections of nucleic acid protein interactions.

Degradation of biomolecules. This is understood to be the destruction of at least one property of a biomolecule. Enzymes can e.g. only reduce the size of biomolecules when the enzymes recognise the structure of the target molecule. The nitrogenous compounds according to the invention can also contribute to this.

In general, the present invention relates to a method for the sample preparation for a successive preparation, processing or analysis method of a sample containing at least one species of nucleic acid and/or a species of protein, whereby the method comprises the following steps:

A) providing a sample which comprises at least one species of a nucleic acid and/or of a protein, B) contacting the sample with a fluid or solid composition to generate a fluid sample preparation, whereby the composition contains at least a nitrogenous compound, which is chosen from the group consisting of a) polyamines, b) amino acids, and oligo- and polypeptides, c) nitrogenous heterocyclic compounds including homo or hetero polymers, which comprise these nitrogenous compounds, d) amines of the type $R^1R^2NR^3$, whereby $R^1$, $R^2$ and $R^3$ are chosen independently from one another from the group consisting of H, $C_1$-$C_5$-alkyl groups and aryl groups, whereby $R^1$, $R^2$ and $R^3$ are not H simultaneously, e) carboxylic acid amides, f) inorganic ammonium salts, g) ammonium groups containing inner salt compounds, h) antibiotica binding nucleic acid, i) compounds, which bind in the small cavity of the DNA, j) nitrogenous compounds chosen from the groups described under a-I with an additional derivation, and mixtures of two or more of these compounds.

The sample can thereby be an organism or a mixture of materials containing nucleic acid and/or protein. The fluid sample preparation produced in step B) comprises a pH between 7.1 and 14, preferably a pH between 7.1 and 12, and particularly preferred a pH between 7.4 and 10 in all embodiments of the method according to the invention.

As a processing method is to be understood every enzymatic, chemical or physical conversion of the biomolecules present in the sample. Special aspects of this method will be explained in the following with reference to special embodiments as further aspects of this invention. These special embodiments relate to, as explained in the following, a method for the lysis of a biological sample, a method for the stabilisation of nucleic acids and/or proteins, a method for the reduction of inhibiting effects in a sample containing nucleic acids and/or proteins, a method for the selective masking of nucleic acids in a sample and analysis methods which respectively build on these methods.

Accordingly, one aspect of the present invention relates to a method for the lysis of a biological sample which contains at least one species of a nucleic acid and/or at least one species of a protein in a casing. In particular, biolgcal casings as e.g. membranes, capsides or cell walls can be used as casings, but the casings are not limited to these. The sample is brought into contact with a fluid or solid composition for the production of a lysate, which contains at least one nitrogenous compound, which is selected from the group consisting of:

a) polyamines, b) amino acids and oligo and polypeptides, c) nitrogenous heterocyclic compounds, including homo or heteropolymeres, which comprise these nitrogenous compounds, d) amines of the type $R^1R^2NR^3$, whereby $R^1$, $R^2$ and $R^3$ are chosen different from one another from the group consisting of H, $C_1$-$C_5$-alkyl groups and aryl groups, whereby $R^1$, $R^2$ and $R^3$ are not H simultaneously, e) carboxylic acid amides, f) inorganic ammonium salts, g) ammonium groups containing inner salt compounds, h) antibiotica binding nucleic acid, i) compounds which bind in the small cavity of the DNA, j) nitrogenous compounds chosen from the groups described under a-i with an additional derivation and mixtures of two or more of these compounds. Amongst "sample which contains at least one species of a nucleic acid and/or at least one species of a protein in a casing" are organisms as understood in line with the present invention. Whether the sample is contacted with a fluid or solid composition, depends if the sample contains sufficient fluid, so that a sufficiently fluid lysate is obtained by the lysis for the further use. The composition will preferably be fluid. The nitrogenous compound can thereby be dissolved in a solvent or be present in a suspended manner.

It is possible with the lysis method according to the invention, to transfer higher amounts of nucleic acids and/or proteins into the lysate compared to standard lysis methods. It is assumed that the nitrogenous compound leads to a more effective dissolving of the casings of the organisms contained in the sample, whereby higher amounts of the cell contents can reach enter the lysate.

In a preferred embodiment of this method, the lysis is carried out in such a manner that the at least one species of the nucleic acid and/or protein is dissolved or suspended in the produced lysate. So as to achieve that at least one species of the nucleic acid and/or protein is dissolved or suspended in the produced lysate, the lysis conditions have to be chosen in such a manner that a precipitation of the at least one nucleic acid and/or of the protein does not occur. The terms "dissolved" and "suspended" in line with the present invention mean that the at least one species of nucleic acid or protein remain in the fluid phase of the sample preparation, for example the lysate, and are thereby accessible for a successive analysis by a corresponding detection or analysis method. This is in contrast to precipitated components of the lysate, which cannot be transferred directly to a detection or analysis method, but which first have to be transferred into the fluid phase by corresponding method steps. The type of sample with which the lysis is carried out has to be considered hereby. Possible further components in the composition which contains the nitrogenous compound also have to be considered here, and possibly the suitable conditions for a certain system of sample and composition have to be determined by means of simple routine examinations. This can for example take place in that it is observed if a precipitation takes place with the lysis. If this is the case, the precipitate can be checked for its composition using analysis methods and procedures used by default, in particular if the precipitate contains the species of nucleic acid and/or protein to be dissolved/suspended. In particular, in this embodiment, the concentration of the nitrogenous compound in the composition has to be chosen in such a manner that the nucleic acid remains dissolved or suspended in the lysate and the nitrogenous compound thereby does not effect a precipitation of the species of nucleic acid and/or protein in the lysate. It is for example possible that the lysate can be subjected to a successive analysis of the species nucleic acid and/or the protein in a reaction system in that at least one species of nucleic acid and/or protein remains dissolved and/or suspended in the lysate. Other cell contents, which are not to be analysed, can be precipitated during the lysis and thus be removed from the fluid sample volume. The at least one species of nucleic acid and/or protein is thereby a species which is provided for a successive preparation, processing or analysis method.

In a further embodiment, the lysis is carried out in the presence of a carrier material for the immobilisation of the at least one species of nucleic acid. Thereby, usual carrier materials can be used, which are usually used in the nucleic acid or protein analysis, e.g. microarrays or so-called "beads". "Beads" are microparticles which have a surface to which molecules can bind. Such a surface can e.g. be achieved by a corresponding surface treatment. Examples of such materials are Oligotex® and Liquichip®, obtained from the company QIAGEN, Hilden, Germany.

In a further embodiment of the method according to the invention, the sample contains at least two species of the group consisting of nucleic acids and proteins. The lysis is carried out in such a manner that the two or more certain species of nucleic acid and/or proteins are contained in the produced lysate, in particular, that these are dissolved or suspended in the lysate. For example, nucleic acids such as DNA and RNA, in particular gDNA and RNA can be contained in the lysate in the method. Alternatively, proteins can selectively be kept in solution/suspension. As described above, the type of the sample and the different lysis reagents have to be considered, in particular the amount of the used nitrogenous compound.

In a further embodiment of the invention, the sample contains at least two species from the group consisting of nucleic acids and/or proteins and the generation of the sample preparation or the lysis is carried out in such a manner that several determined species of nucleic acid and/or protein are dissolved and/or suspended in the produced lysate. Thereby, either the species of nucleic acids contained in the sample or all species of proteins contained in the solution can be dissolved and/or suspended. This means that essentially no precipitation takes place during the lysis, as is used e.g. for the removal of nucleic acids or proteins from lysates. If the sample contains several species of nucleic acid and/or proteins, and two, several or all of these species shall remain dissolved and/or suspended in the lysate after the lysis, it is particularly preferred that the relative concentration of these different species of nucleic acids and/or proteins do not change with regard to one another by the lysis and thereby the relative concentration of these species in the lysate remains essentially unchanged with regard to the relative concentration of this species in the sample. It again applies, as already disclosed above, to consider the type of the sample and the different possibly used ysis reagents and the type of the used nitrogenous compound during the execution of the lysis and that suitable routine tests have possibly to be carried out, to determine suitable conditions for a given sample type.

By the above-described lysis methods, where at least two species of nucleic acid and/or proteins are dissolved and/or suspended in the lysate, it is possible to use the lysate containing these species for the analysis or the detection of every one of these species in a successive analysis or detection method.

The nitrogenous compound can thereby, in addition to a more effective lysis, which leads to an increased concentration of the desired species of nucleic acid and/or protein in the lysate, also have a stabilising effect on the species of nucleic acid and/or protein dissolved and/or suspended in the lysate. Furthermore, the inhibiting interactions and effects in the lysate can be decreased or suppressed by the use of the nitrogenous compound in the composition used for the lysis. Furthermore, it is possible by the use of the nitrogenous compound, to mask a certain species of nucleic acid in the lysate, so that this species of nucleic acid does not have any disadvantageous effects on the analysis or detection method of a further species contained in the lysate. These special additional aspects are discussed in more detail in the following.

In a further preferred embodiment of the method, DNA and/or RNA are dissolved and/or suspended in the lysate as nucleic acid species. In another embodiment, one or more species of protein are dissolved and/or suspended in the lysate.

In a further preferred embodiment of the lysis method according to the invention, the composition used for the lysis comprises, in addition to the nitrogenous compound, further lysis reagents, at least one reagant from the group of the complexing agents, detergents, substances for the volume restriction and/or solvents. In particular EGTA (ethylene glycol-bis(2-amino ethylether)-N,N,N',N'-tetra acetic acid) and EDTA (ethylene dinitrilotetra acetic acid) are considered as complexing agents. Possible detergents are in particular tritonx100 (polyethylene glycol-tert.-octylphenylether), Nonidet-P40 (Nonylphenyl-polyethylene glycol), n-Ocytlglucosid and N-Cetyl-N,N,N-trimethyl-ammonium bromide. As substances for the volume restriction are in particular considered polyethylene glycoles of different chain lengths. $H_2O$ or phenol or mixtures thereof are preferably used as solvents. The complexing agents are preferably used in an amount, so that they are respectively present in the sample preparation, e.g. the lysate in a concentration of 0.1 to 10 mM. If fluid compositions are used as compositions used for the lysis, that is, a lysis buffer, the complexing agents are respectively preferably present in a concentration of 0.1 to 10 mM. The detergents are preferably used in an amount, so that they are respectively present in the sample preparation, e.g. the lysate in a concentration of 0.01-10 vol %. If a lysis buffer is used, the detergents are preferably 0.01 to 10 vol % of the lysis buffer. The reagants for the volume restriction are preferably used in an amount, so that they are respectively present in the sample preparation, e.g. the lysate in a concentration of 0.01-5 vol %. If a lysis buffer is used, it preferably contains between 0.01 and 5 vol % reagants for the volume restriction. The lysis reagants are preferred as a solution, but they can also be added differently, e.g. in the form of a solid substance. For the present invention, lysis buffers are particularly used as compositions, consisting of $H_2O$ as solvent, at least one of the above-mentioned nitrogenous compounds as additive and optional complexing agents, detergents, and/or substances for the volume restriction. In particular, lysis buffer can be used, which comprise all of these components. A further aspect of the present invention accordingly relates to compositions for the lysis of a biological sample, whereby the sample comprises at least one nitrogenous compound used in line with the different methods according to the invention and at least a further lysis reagant, as described above in connection with the lysis method according to the invention.

The lysis can further be carried out under mechanical effect or with enzymatic support. As a means for the mechanical support are considered mortars, the application of high pressure, narrow capillaries and the use of filter units. An enzymatic support of the lysis can for example be supported by the use of proteases, lysozymes, cellulases, pectinases, whereby the degradation of the structure of the organisms in the sample is supported further.

The lysis can be designed more efficiently by this support, that is, the yield of nucleic acid and/or protein in the lysate can be increased or accelerated. It is further possible that the sample is washed with a washing buffer, in particular a hypotonic washing buffer, prior to the lysis.

In a preferred embodiment of the lysis method according to the invention, the amount of the used nitrogenous compound is chosen in such a manner that the concentration of the nitrogenous compound in the generated lysate is between 0.001 mM to 1 M, preferably between 0.001 to 100 mM, particularly preferably between 0.001 to 30 mM, 0.001 to 20 mM, and specially 0.001 to 19 mM or 0.001 to 15 mM.

During the use of heterocyclic compounds as the nitrogenous compound, in particular of imidazole, the amount of the compound can be chosen so that a concentration of 0.01 to 20 mM of imidazole is adjusted in the lysate, particularly preferred from 0.01 to 15 mM. For compounds comprising amino functionalities, it usually applies that the concentration of the nitrogenous compound can be lower, the more amino functionalities are contained in the nitrogenous compound, which can interact with the nucleic acid or the protein.

In a further preferred embodiment of the lysis method according to the invention, the at least one nucleic acid species is a DNA species. In a further preferred embodiment of the lysis method according to the invention, the at least one nucleic acid species is a RNA species. In a further preferred embodiment of the lysis method according to the invention, the at least one species of biomolecule is a protein species.

In a further preferred embodiment of the lysis method according to the invention, the nitrogenous compound is chosen from the group consisting of:

a) polyamines, which are preferably selected from the group consisting of open-chained and cyclic polyamines with 2, 3, 4, 5 or 6 amino groups. The term "polyamine" is to be understood in line with the invention in particular compounds which comprise a saturated carbon chain with amino group ends. The amino group ends can be primary ($H_2N-$), secondary ($R_1NH-$) oder tertiary amino groups ($R_1R_2N-$) and can be part of a cyclic group. The remainders $R_1$ and $R_2$ here can be $C_1$-$C_5$-alkyl groups independent from one another. The amino group ends are preferably primary or secondary amino groups. The saturated carbon chain can be interrupted with a changing number of secondary ($-NH-$) or tertiary ($-NR_1-$), preferably secondary amino groups. $R_1$ can again be a $C_1$-$C_5$-alkyl group. The saturated carbon chain can for example be open-chained, unbranched or cyclic. The carbon chain or the single carbon chains connecting the different amino groups are preferably alkylene groups $-(CH_2)_n-$, whereby n is a whole number from 1 to 6, preferably from 2 or 3. The cyclic carbon chains can be pure carbon rings and saturated nitrogenous ring groups as e.g. piperidine or piperazine. The rings thereby preferably contain 4 to 6 ring atoms. The nitrogenous ring groups can be substituted at least one of the nitrogen atoms contained in the ring with a saturated carbon chain with amino group ends. This carbon chain can again be interrupted by secondary or tertiary, preferably secondary amino groups. The carbon chains are also preferably alkylene groups $-(CH_2)_n-$ here, whereby n can be a whole number from 2 to 6 and is preferably 2 or 3. Even though polyamines with 2 to 6 amino groups are preferred, the polyamines can also contain more amino groups. In particular, the term polyamines are also meant to be polymeric straight chained or branched polyamines as e.g. polyethylene imines or vinyl amines.

As polyamines can in particular be used ethylene diamine, trimethylene diamine or putrescine, spermidine, cadaverine, diethylentriamine, spermine, triethylene tetramine, tetraethylene pentamine, pentaethylene hexamine, 1,4-Bis(3-aminopropyl)-piperazine, 1-(2-aminoethyl)piperazine, 1-(2-aminoethyl)piperidine, 1,4,10,13-Tetraoxa-7,16-diazacyclooctadecane, Poly(1-vinylpyrrolidon-co-2-dimethylaminoethylmethacrylate) and Tris(2-aminoethyl) amine) and similar. The use of unbranched polyamines with 2 to 6 amino groups is particularly preferred, in particular ethylene diamine, trimethylene diamene or putrescine, spermidine, diethylene triamine, spermine, triethylene tetramine, tetraethylene pentamine, pentaethylene hexamine, whereby the use of spermidine is particularly preferred.

b) amino acids, in particular α-amino acids. The amino acids can thereby be present in the D or L form or as racemate. Proteinogene and non-proteinogene, but in particular proteinogene amino acids can be used. Polar and also apolar amino acids can be used. The apolar amino acids thereby comprise the aliphatic (e.g. glycine, alanine, valine, leucine, and isoleucine) and aromatic amino acids (e.g. phenylalanine, tyrosine, tryptophane). Polar amino acids can comprise neutral, base and also acidic amino acids, or the amides of the acidic amino acids. The neutral amino acids can e.g. be selected from the imino acids such as proline or the amino acids with hydroxy groups as e.g. serine and threonine or the sulfur-containing amino acids as e.g. cysteine and methionine. Furthermore, the amino acids can be selected from the alkaline amino acids as e.g. lysine, arginine and histidine. The amino acids can also be selected from the acidic amino acids as e.g. asparagic acid, glutamic acid or their amides as e.g. asparagine or glutamine.

Amino acids such as arginine, proline, tryptophane and glutamic acid are preferably used as a nitrogenous compound. In a further embodiment, amino acids are used as nitrogenous compounds, which do not comprise a reducing thio group.

c) Heterocyclic compounds, which are selected from the group of the five or six member rings or the six member rings with anellated five member ring, whereby the five member ring, the six member ring and/or the anellated five member ring comprises 1 to 3 nitrogen atoms. The five or six member rings and the anellated rings can be unsaturated, partially unsaturated or aromatic. The respective ring members can comprise substituents in the ring compounds, which are selected from the group consisting of H, $C_1$-$C_6$-alkyl groups, $=O$, $-OH$, $=S$, $-SH$, $=NH$, $-NH_2$, alkyl-O—, alkyl-S—, alkylamino- and dialkylamino groups, whereby these alkyl groups (that is, the alkyl groups in the alkyl-O—, alkyl-S—, alkylamino- and dialkylamino groups) are $C_1$-$C_5$-alkyl groups, preferably $C_1$-$C_3$-alkyl groups. The ring members can furthermore be substituted with F—, Cl—, Br— or J. The heterocyclic compounds can, respectively in the five or six member ring groups, comprise ine or more O- or S-atoms as further hetero atom. Prefer red heterocyclic compounds are aromatic nitrogenous 5 member ring compounds of the general formula I:

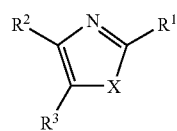

formula I whereby X is selected from NH or S, $R^1$, $R^2$, and $R^3$ are selected independently from one another from the group consisting of —H, —F, —Cl, —Br, -J, —OH, —SH, —$NH_2$, —C(=O)OH, —C(=O)$NH_2$, alkyl-O—, alkyl-S—, alkylamino- and dialkylamino groups, whereby these alkyl groups are $C_1$-$C_5$-alkyl groups, preferably $C_1$-$C_3$-alkyl groups. Particularly preferred are the compounds imidazole, thiazole and aminothiazole, in particular 2-amino thiazole.

Further preferred heterocyclic compounds are aromatic six member ring compounds of the general formula II:

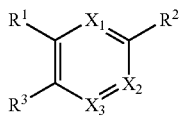

formula II whereby $X_1$ is selected from the group consisting of N, O, S and $CR^4$, $X_2$ is selected from the group consisting of N, O, S and $CR^5$, and $X_3$ is selected from the group consisting of N, O, S and $CR^6$, whereby at least one of the groups $X_1$, $X_2$ oder $X_3$ represents N, and $R^1$, $R^2$, $R^3$, $R^4$, $R^5$ and $R^6$ are selected independently from one another from the group consisting of H, $C_1$-$C_6$-Alkylgruppen, —OH, —SH, —$NH_2$, —F, —Cl, —Br, —I, alkyl-O—, alkyl-S—, alkylamino- and dialkylamino groups, whereby these alkyl groups (that is, the alkyl groups in the alkyl-O—, alkyl-S—, alkylamino- and dialkylamino groups) are $C_1$-$C_5$-alkyl groups, preferably $C_1$-$C_3$-alkyl groups. $X_1$, $X_2$ and/or $X_3$ preferably represent N. It is further preferred that either only $X_1$ is N, or $X_1$ and $X_2$ or $X_1$ and $X_3$ are N. $R^1$ to $R^5$ are preferably selected from the group consisting of H and $C_1$-$C_3$-alkyl, and is preferably H or methyl. The compounds 2,3-dimethylpyrazine, pyridine, and pyrimidine are particularly preferred.

Compounds according to the general formula III are further preferred:

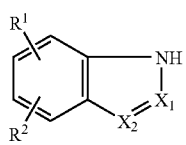

formula III whereby $X_1$ is selected from the group consisting of N, O, S and $CR^3$, $X_2$ is selected from the group consisting of N, O, S and $CR^4$, and $R^1$, $R^2$, $R^3$ and $R^4$ are selected independently from one another from the group consisting of H, $C_1$-$C_6$-alkyl groups, —OH, —SH, —$NH_2$, —F, —Cl, —Br, —I, alkyl-O—, alkyl-S—, alkylamino- and dialkylamino-, whereby these alkyl groups (that is, the alkyl groups in the alkyl-O—, alkyl-S—, alkylamino- and dialkylamino groups) are $C_1$-$C_5$-alkylgruppen, preferably $C_1$-$C_3$-alkyl groups.

Either $X_1$ or $X_2$ preferably represent N. Further, when $X_1$ is $CR^4$, $X_2$ can be $CR^5$. $R^1$, $R^2$, $R^3$ and $R^4$ preferably represent H.

Particularly preferred compounds are indazole and benzimidazole.

The heterocyclic compounds selected from the group of the nucleobases are further preferred as nitrogenous compounds. These comprise in particular the compounds adenine, cytosine, guanine, inosine, hypoxanthine, thymine, uracile and xanthine or the compounds which can be built into nucleic acid as analogons or derivatives, whereby the structure of these compounds can also comprise differences in the ring. The compounds adenine, cytosine, guanine and thymine are particularly preferred here.

The compounds imidazole and 2,3-dimethylpyrazine, pyrimidine, guanine and guanosine show a particularly good effectiveness in the present invention.

Furthermore, nitrogenous heterocyclic compounds are homo or hetero polymers which comprise these nitrogenous compounds.

d) amines of the type $R^1R^2NR^3$, whereby the remainders $R^1$, $R^2$ and $R^3$ are chosen independently from one another from the group consisting of H and $C_1$-$C_3$-alkyl groups, whereby applies that $R^1$, $R^2$ and $R^3$ are not H simultaneously. The use of methylamine, ethylamine, n-propylamine, dimethylamine, diethylamine, di(n-propyl)amine, di(isopropyl)amine, trimethylamine, triethylamine, tri(n-propyl)amine, and tri(isopropyl)amine is particularly preferred.

e) carboxylic acid amides comprising the structure X—C(=O)$NH_2$. X is thereby selected from the group consisting of: —$NH_2$, $C_1$-$C_5$-alkyl, $C_2$-$C_5$-alkenyl, $C_2$-$C_5$-alkinyl or aryl, preferably phenyl or an amino-substituted aryl, $H_2$NC(=O)—Y—, whereby Y can be an alkylene group of the type —$(CH_2)_n$— and whereby n is a whole number from the region 0 to 10, preferably 0 to 5, or Y is a $C_1$-$C_{10}$-alkenylene group, preferably a $C_1$-$C_6$-alkenylene group, or an aryl group. When Y is a $C_1$-$C_{10}$-alkenylene group, this group can comprise one or more olefin bonds, whereby the olefin bonds can be present in the carbon chain in an isolated manner or in a conjugated manner. When Y is an aryl rest, phenyl or bophenyl groups are particularly considered. X—$NH_2$ preferably represents —$NH_2$ or 2 amino phenyl.

f) inorganic ammonium salts, which are selected from the group consisting of ammonium sulfate, ammonium carbonate and ammonium hydrogen phoshate, g) ammonium groups containing inner salt compounds, which are selected from betaine, ectoine and trimethyl amine oxide;

h) antibiotics binding the nucleic acid, which are selected from the group consisting of distamycines, in particular distamycine D, mitomycines, norfloxacins, streptozocine, duocarmycines, actinomycines, and aminoglycisides; and i) compounds which bind in the small cavity of DNA, and which are selected from the grouop consisting of thiazotropsine, tri-imidazole and chromomycines.

j) nitrogenous compound selected from the groups described under a-i, with an additional derivating. The derivating can for example be carried out by a combination of the nitrogenous compounds with inorganic or organic remainders such as sugars, phosphates, alcohols, sulfates, glutathione, lipides etc. The compounds guanosine, adenosine, cytosine, and thymindine or also antibiotica are particularly preferred here.

The preferred nitrogenous compounds described above can be used in all of the further aspects according to the invention still to be explained in the following. The nitrogenous compounds, which find use in the present invention, can generally be present in a free form or in the form of suitable salts. Whether a compound is used as a free compound or as a salt can depend if the composition shall be present in a fluid or solid form.

$C_1$-$C_6$-alkyl groups are particularly the following groups in line with the present invention: methyl, ethyl, propyl, isopropyl, butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and/or 1-ethyl-2-methyl-propyl.

The $C_2$-$C_5$-alkenyl groups in line with the present invention are particular the groups ethenyl (vinyl), 2-propenyl (allyl), 2-butenyl, 3-butenyl, 1-methyl-2-propenyl, 2-methyl-2-propenyl, 2-pentyl, 3-pentyl, 4-pentyl, 1-methyl-2-butenyl, 2-methyl-3-butenyl, 3-methyl-3-butenyl, 1,1-dimethyl-2-propenyl, 1,2-dimethyl-2-propenyl, and 1-ethyl-2-propenyl. The $C_2$-$C_5$-alkinyl in line with the invention are in particular ethinyl, 2-propinyl (propargyl), 2-butinyl, 3-butinyl, 2-pentinyl, 3-pentinyl, 4-pentinyl, 3- and methyl-2-butinyl.

The choice of the nitrogenous compound which is used for the lysis, is preferably adjusted to the solvent used in the lysis buffer. It is thereby preferred that the nitrogenous compound is soluble in the solvent in such a measure that concentrations of the compound are possible in the solvent in the respective desired region.

In a further aspect, the present invention relates to an analysis method for the detection of at least one species of nucleic acid and/or at least one species of protein in a sample, comprising the steps:
A) generation of a lysate according to the lysis method according to the invention, and
B) use of the lysate in a reaction or reaction sequence suitable for the detection of the at least one species of protein.

The detection accuracy of the analysis method is improved by the improved lysis, as higher concentrations of the respective nucleic acid and/or protein are achieved in the sample compared to usual analysis methods.

The lysate is preferably used directly without carrying out further method steps for the reduction of the number of species of nucleic acid and/or proteins contained in the sample preparation or that further steps for the removal of materials which effect the degradation of nucleic acids and/or proteins have to be carried out from the sample preparation or that such materials have to be inactivated. The lysate is thereby preferably used directly for the analysis or for the production of a reaction solution suitable for the analysis, without any further recoditioning step.

In other cases, the lysis can be supported by the above-mentioned methods for the physical, chemical or enzymatic lysis. Lysis methods with physical support by heating or homogenisation of the lysate, with chemical support by use of detergents or enzymatic support by use of proteases as e.g. protease K (if protein is not to be detected), lysozyme or also nucleases (e.g. DNase; in this case DNA cannot be detected) as suitable.

The reaction or reaction sequence suitable for the detection of the at least one nucleic acid can thereby be selected from the group of the nucleic acid binding reactions, in particular the nucleic acid hybridisations, in particular Northern, Southern blotting or also hybridisation of oligo nucleotides and probes, in particular DNA probes, the group of the enzymatic modifications or polymerisations of nucleic acids, in particular sequencing reactions, in-vitro transcription, restriction endonuclease splittings, the group of the amplification reactions, in particular PCR (polymerase chain reaction), real-time-PCR RT-PCR (reverse transcription polymerase chain reaction), real-time-RT-PCR (method based as probes and as a method that is dependent on a sequence-unspecifically binding detector molecule as e.g. SybrGreen), RT-PCR (reverse transcription polymerase chain reaction), real-time-RT-PCR (method based as probes and as a method that is dependent on a sequence-unspecifically binding detector molecule as e.g. SybrGreen), Multiplex PCR, Multiplex RT-PCR, die sondenbasierenden Verfahren der Real-Time Multiplex PCR und Real-Time Multiplex RT-PCR, NASBA (Nucleic Acid Sequence Based Amplification), 3SR (Sequence Sustained Self Replication), 2SR, TMA (Transcription Mediated Amplification), MDA (Multiple Displacement Amplification) Rolling Circle Amplification, Whole-Transcriptome-Amplification, Whole-Genome-Amplification und Rolling Transcription Amplification oder Loop-mediated isothermal amplification (LAMP).

The reaction or reaction sequence suitable for the detection of the at least one protein can be selected from the group of the protein-binding reactions, in particular protein recognition, in particular by other proteins, reactions based on the enzymatic activity of the protein, antibodies, aptameres, ligands, nucleic acids, in particular Western blotting, or other substances such as gluathione and NAD, or is selected from the group of the protein modification or processing, in particular (de)phosphorylation, (de)glycolysation and splitting through proteases.

All methods mentioned above can be carried out either in solution, suspension or solid phase.

In a further aspect, the present invention relates to a method for the stabilisation of nucleic acids and/or proteins, whereby this method comprises the following steps:
A) providing a sample which comprises at least one species of a nucleic acid and/or of a protein,
B) contacting the sample with a fluid or solid composition to produce a fluid sample preparation, whereby the composition contains at least a nitrogenous compound, which is selected from the group consisting of
a) polyamines, b) amino acids and oligo and und polypeptide, c) nitrogenous heterocyclic compounds, including homo or heteropolymeres, which comprise these nitrogenous compounds, d) amines of the type $R^1R^2NR^3$, whereby $R^1$, $R^2$ and $R^3$ are chosen different from one another from the group consisting of H, $C_1$-$C_5$-alkyl groups and aryl groups, whereby $R^1$, $R^2$ and $R^3$ are not H simultaneously, e) carboxylic acid amides, f) inorganic ammonium salts, g) ammonium groups containing inner salt compounds, h) antibiotica binding nucleic acid, i) compounds which bind in the small cavity of the DNA, j) nitrogenous compounds chosen from the groups described under a-I with an additional derivation and mixtures of two or more of these compounds.

In a further embodiment of this method, the stabilisation of nucleic acids is carried out by one or more of the claimed substances before, during or after an enzymatic, physical or chemical lysis, preferably using detergents and protease as e.g. proteinase K. Thus, detergents with a concentration of 0.005 to 10% are used. Proteases as e.g. the proteinase K can be contained in the stabilised sample in a concentration of $0.5 \times 10^{-4}$ mAU/µl to $50 \times 10^{-4}$ mAU/µl.

In a further embodiment of this method, the stabilisation of RNA is carried out by one or more of the claimed substances following after an enzymatic degradation by an endonuclease as e.g. DNase. The DNase I can thus be contained in the stabilised sample in a concentration of 0.003 U/µl×0.5 U/µl.

In a further embodiment of this method, the stabilisation of protein by one or more of the claimed substances is carried out following after an enzymatic degradation by nucleic acids by nucleases as e.g. RNase, DNases, benzonases etc.

In a further embodiment of this method, the stabilisation of biomolecules is carried out in the sample e.g. of nucleic acid or protein by one or several of the claimed substances chosen from e.g. treatment of the at least two species of biomolecule is carried out in the sample through a substance chosen from e.g. arginine, imidazole, proline, lysine, spermine, spermidine, glutamic acid, indazole, thymine, thymidine, guanine, guanosine, adenine, histidine, tryptophane, ammonium sulfate or by a mixture of these.

In a further embodiment of this method, the at least one species of nucleic acid or protein is immobilised on a carrier material before, during or after the addition of the nitrogenous compound. The materials already mentioned above in connection with the lysis according to the invention can be used as carrier materials.

In an alternative embodiment of the stabilisation method according to the invention, the sample preparation takes place in such a manner that the at least one species of the nucleic acid and/or of the protein is dissolved and/or suspended in the fluid sample preparation. This can particularly be effected by the addition of suitable amounts of the nitrogenous compound to the sample. If a lysis of a biological sample is effected by the addition of the composition, the lysis can correspondingly be carried out in such a manner that at least one species of the nucleic acid/and or of the protein is dissolved and/or suspended in the fluid sample preparation.

A sample is, in addition to organisms, which are subjected to a lysis for the purpose of the disintegration, every mixture of materials which comprises at least one species of a nucleic acid and/or of a protein. This can be a mixture of materials or only the pure nucleic acid or the protein. These mixtures of material can be obtained e.g. through nucleic acid or protein acid preparations. Carrier materials, on which at least one species of nucleic acid and/or protein was immobilised, can also be used as samples. The sample can thereby be present as a solid or as a solution, or it can be pure organisms or suspensions of organisms in a fluid medium as e.g. cell cultures. The composition of the sample can be added as a fluid, e.g. as a buffer solution or as a solid in dependence of the type of the sample. Sample preparations which contain at least one fluid phase are a fluid sample preparation. The sample preparation can e.g. be completely dissolved or can also comprise suspended components and solid components. Cell components can for example be suspended or be present in the sample preparation in an undissolved manner. The sample preparation can also comprise a carrier material for the immobilisation of nucleic acid and/or proteins.

The at least one species of nucleic acid or protein can be stabilised by addition of the nitrogenous compound or protein in the sample preparation, so that a direct separation of this species of components in the sample preparation, which would disintegrate or decompose this species without the stabilisation by the nitrogenous compound, is not necessary or can take place at a later time than usual. It is particularly preferred if a successive purification of the sample preparation can be entirely foregone, and the sample preparation can be used directly in an analysis or in a detection method. On the one hand, the detection of the species of nucleic acid or protein is thereby improved, as this species is present in a stabilised manner in the analysis solution and its concentration does not decrease in this analysis solution or only to a small measure, than with a comparing system without nitrogenous compound, and thereby more substance is available over the period of the analysis. On the other hand, time-consuming and expensive and contamination-prone purification steps can be foregone more easily. It was further determined that in the samples, in which the species of nucleic acid and/or of protein are present in addition to cellular substances, as they are particularly present in a cell lysate, they can possibly be stabilised additionally.

In a preferred embodiment of the stabilisation method according to the invention, the sample is a biological sample, which is subjected to a lysis and possibly further purification steps prior to the contacting with the composition for the generation of the fluid sample preparation. The lysis can take place with usual lysis methods, and the further purification steps can for example be a preparation method or immobilisation method of a nucleic acid or protein preparation.

In a further preferred embodiment of the method according to the invention, the sample is a biological sample in which the at least one species of a nucleic acid and/or at least one protein are contained in a casing, preferably a biological casing, and whereby the sample is contacted with the fluid or solid composition to produce a lysate. The sample can also contain organisms. The lysate is preferably generated for the lysis of a biological sample according to the method of the invention described above.

In a further embodiment of the method according to the invention, the sample contains at least two species of the group consisting of nucleic acids and proteins. The sample preparation is generated in such a manner, or the lysis is carried out in such a manner that the two or more certain species of nucleic acid and/or proteins in the produced sample preparation or the produced lysate, are dissolved or suspended or immobilised on a carrier material. For example, nucleic acids such as DNA and RNA, in particular gDNA and RNA can be dissolved or suspended in the sample preparation or in the lysate. Alternatively, proteins can selectively be kept in solution. As described above, during the choice of the conditions which have to be used with the generation of the sample preparation or the lysis, the type of the sample and the different components, which are contained in the composition used for the generation of the sample preparation have to be considered, and in particular the amount of the used nitrogenous compound.

In a further preferred embodiment of the stabilisation method according to the invention, the sample contains at least two species from the group consisting of nucleic acids and proteins and the sample preparation or the lysis is carried out in such a manner that the species of nucleic acid and/or proteins contained in the sample are essentially dissolved and/or suspended or immobilised in the sample generated preparation or the lysate by the majority. Preferably, all species are essentially dissolved and/or suspended or immobilised. Thereby, either all of the species of nucleic acids contained in the sample or all of species of proteins contained in the sample can be dissolved and/or suspended. This means, that during the sample preparation or during the lysis, essentially no precipitation takes place, as is e.g. used for the removal of nucleic acids or proteins from lysates. If the sample contains several species of nucleic acids and/or proteins, and two, several or all of these species shall remain dissolved and/or suspended in the lysate after the contacting with the nitrogenous compound, it is particularly preferred that the relative concentration of these different species of nucleic acids and/or proteins do not change with regard to one another by the addition of the composition containing the nitrogenous compound or through the lysis. That is, the relative concentration of this species in the sample preparation or the lysate compared to the relative concentration of this species in the untreated sample remains essentially unchanged. It again applies, as already disclosed above, to consider the type of the sample and the different possibly used ysis reagants and the type of the used nitrogenous compound during the execution of the lysis and that suitable routine tests have possibly to be carried out, to determine suitable conditions for a given sample type.

In a further preferred embodiment of the stabilisation method according to the invention, DNA and/or RNA are dissolved and/or suspended or immobilised in the sample preparation or lysate. Additionally or alternatively, at least one species of protein can be dissolved and/or suspended or immobilised in the sample preparation or in the lysate.

As has already been described above in connection with the method according to the invention for the lysis of a biological sample, the composition used for the lysis can contain at least a reagant of the group of the complexing agents, detergents, substances for volume restriction and/or solvents as further lysis reagants. The lysis can also take place under mechanical action and/or in an enzymatic manner, or the sample can be washed with a hypotonic washing buffer before the lysis. The lysis can thereby be supported by the above-mentioned methods for the physical, chemical or enzymatic lysis. Lysis methods with physical support by heating or homogenisation of the lysate, with chemical support by use of detergents or enzymatic support by use of proteases as e.g. protease K (if protein is not to be detected), lysozyme or also nucleases (e.g. DNase; in this case DNA cannot be detected) have proved to be particularly suitable. The implementations made above in connection with the lysis method according to the invention apply here in the same manner.

In the stabilisation method according to the invention, the amount of the nitrogenous compound which is added to the sample, is preferably chosen in such a manner that the concentration of the nitrogenous compound in the produced sample preparation or the lysate is between 0.001 mM to 1 M, preferably between 0.001 to 100 mM, particularly preferably between 0.001 to 30 mM and specially between 0.001 to 19 mM or 0.001 to 15 mM. If polyamines (a) are used, the concentration is preferably between 0.001 mM and 15 mM, preferably between 0.001 to 1 mM. An essential stabilisation of e.g. RNA is surprisingly determined, even with these very small concentrations of polyamines, in particular spermidine. During the use of amino acids (b), the concentration can preferably be in the region of 0.001 mM to 20 mM, in particular in the region of 1 to 15 mM. During the use of nitrogenous heterocycles (c), the concentration can preferably be between 0.001 to 20 mM, preferably 0.001 to 15 mM. During the use of carboxylic acid amines (e), the concentration can preferably be between 0.001 to 15 mM. If inorganic ammonium compounds are used, the concentration can preferably be between 0.001 mM to 100 mM, in particular preferably 0.001 to 15 mM. During the use of ammonium groups containing inner salt compounds, the concentration is preferably 0.001 mM to 300 mM, in particular preferably 0.001 to 200 mM.

Regarding the type of the nitrogenous compounds, which can preferably be used in the stabilisation method according to the invention, the implementations made above with regard to the lysis method according to the invention apply in the same manner.

In a further aspect, the present invention relates to an analysis method for the detection of at least one species of nucleic acid and/or proteins in a sample, whereby the method comprises the following steps:
a) providing a sample preparation or a lysate which contains at least one species of a nucleic acid and/or at least of a protein, whereby the at least one species of nucleic acid and/or protein was stabilised with the stabilising method according to the invention, and
b) use of the sample preparation in a reaction or reaction sequence suitable for the detection of the at least one nucleic acid or the at least one protein. The sample preparation is preferably used directly, without carrying out further method steps for the reduction of the number of the species of nucleic acids and/or proteins contained in the sample preparation and/or for the removal or inactivation of the substances from the sample preparation effecting the degradation of nucleic acids and/or proteins.

An improved detection can be achieved by this method, due to the stabilisation of the species of nucleic acid and/or the species of protein to be detected, whereby a sample reconditioning preceding the detection reaction can preferably be foregone. As the species of nucleic acid or protein to be detected is stablised, the detection can be conducted with small sample amounts.

Regarding the type of the reaction or reaction sequence used for the detection of the corresponding species of nucleic acid and/or protein, the implementations made above in connection with the lysis according to the invention apply.

In addition to the stabilisation, the use of the nitrogenous compound during the generation of the sample preparation or of the lysate can also lead to a masking of certain further species of nucleic acid contained in the sample. If the sample is subjected to a lysis, an improvement of the lysis can also be achieved, in particular an increased concentration of the desired species of nucleic acid and/or protein in the lysate. In addition to the stabilisation, a masking of certain species of nucleic acid can possibly be achieved in the sample. The inhibiting effects in the generated sample preparation or the lysate can also possibly be decreased by the use of the nitrogenous compound.

In a further aspect, the present invention relates to a method for decreasing inhibiting effects in a sample, which contains at least a species of nucleic acid and/or a species of protein and at least an inhibiting substance. This method comprises the following steps:
A) providing a sample which comprises at least one species of a nucleic acid and/or of a protein, and at least one inhibiting substance,
B) contacting the sample with a fluid or solid composition to generate a fluid sample preparation, whereby the composition contains at least a nitrogenous compound, which is chosen from the group consisting of a) polyamines, b) amino acids, and oligo- and polypeptides, c) nitrogenous heterocyclic compounds including homo or hetero polymers, which comprise these nitrogenous compounds, d) amines of the type $R^1R^2NR^3$, whereby $R^1$, $R^2$ and $R^3$ are chosen independently from one another from the group consisting of H, $C_1$-$C_5$-alkyl groups and aryl groups, whereby $R^1$, $R^2$ and $R^3$ are not H simultaneously, e) carboxylic acid amides, f) inorganic ammonium salts, g) ammonium groups containing inner salt compounds, h) antibiotica binding nucleic acid, i) compounds, which bind in the small cavity of the DNA, j) nitrogenous compounds chosen from the groups described under a-i with an additional derivation, and mixtures of two or more of these compounds, whereby the amount of the nitrogenous compound, which is added to the sample, is chosen in such a manner that the inhibiting effect of the inhibiting substance is reduced in the fluid sample preparation.

The term inhibiting substance is to be understood as every substance which, in a subsequent analysis or detection method, which is carried out with the sample preparation or a sample obtained by further reconditioning steps, acts in an inhibiting manner, that is, is disadvantageous for the detection reaction. If nucleic acids are present in the sample, which are to be detected, e.g. proteins can represent such inhibiting substances. If proteins are to be detected in the sample, nucleic acids can e.g. represent such inhibiting substances. The mutual inhibiting effect of proteins and nucleic acids can for example be based on the formation of nucleoprotein complexes. In preferred embodiments of the present invention, the inhibiting substance is a protein, in particular a nucleic acid-binding protein, or a protein-binding nucleic acid.

An interaction between the species of nucleic acid and/or the species of protein and the inhibiting substance takes place which affects an analysis or detection reaction carried out with the sample preparation in a disadvantageous manner is understood to be an inhibiting effect here. By the presence of the inhibiting substance, the result of this reaction with regard to an identical sample which does not contain the inhibiting substance, is thereby influenced in a disadvantageous manner. A reduction of the inhibiting effect can be determined in that e.g. a following analysis or detection reaction of a certain species of nucleic acid or protein, which is carried out with a sample, to which was added one of the nitrogenous compounds which are used according to the invention, is improved compared to the same analysis or detection reaction which was carried out with the same sample, to which no nitrogenous compound was added.

A sample is, in addition to organisms, which are subjected to a lysis for the purpose of the disintegration, every mixture of materials which comprises at least one species of a nucleic acid and/or of a protein. This can be a mixture of materials or only the pure nucleic acid or the protein. These mixtures of material can be obtained e.g. through nucleic acid or protein acid preparations. The sample can thereby be present as a solid or as a solution, or it can be pure organisms or suspensions of organisms in a fluid medium as e.g. cell cultures. The composition of the sample can be added as a fluid, e.g. as a buffer solution or as a solid in dependence of the type of the sample.

In a preferred embodiment of the present invention, the sample is a biological sample, which is subjected to a lysis and possibly further purification steps prior to the contacting with the composition for the generation of the fluid sample preparation. The lysis can take place with usual lysis methods, and the further purification steps can for example be a preparation method of a nucleic acid or protein preparation. The lysis can thereby be supported by the above-mentioned methods for the physical, chemical or enzymatic lysis. Lysis methods with physical support by heating or homogenisation of the lysate, with chemical support by use of detergents or enzymatic support by use of proteases as e.g. protease K (if protein is not to be detected), lysozyme or also nucleases (e.g. DNase; in this case DNA not detected) have proved to be suitable.

In an embodiment of this method, the stabilisation of nucleic acids is carried out by one of the chosen substances following an enzymatic, physical or chemical lysis, in particularly preferred using detergents and protease as e.g. proteinase K. Thus, detergents with a concentration of 0.005 to 10% are used for example. Proteases as e.g. the proteinase K can be contained in the stabilised sample in a concentration of $0.5 \times 10^{-4}$ mAU/µl to $50 \times 10^{-4}$ mAU/µl.

In a further embodiment of this method, the stabilisation of RNA by one or more of the claimed substances is carried out following an enzymatic degradation by an endonuclease as e.g. DNase. The DNase I can thus be contained in a concentration of 0.003 U/µl to 0.5 U/µl in the stabilised sample.

In a further embodiment of this method, the stabilisation of protein by one or more of the claimed substances is carried out following an enzymatic degradation by nucleic acids by nucleases as e.g. RNase, DNases, benzonases etc.

In a further embodiment of this method, the stabilisation of biomolecules is carried out in the sample e.g. of nucleic acid or protein by one or several of the claimed substances chosen from e.g. arginine, imidazole, proline, lysine, spermine, spermidine, glutamic acid, indazole, thymine, thymidine, guanine, guanosine, adenine, histidine, tryptophane, ammonium sulfate or by a mixture of these.

In a further preferred embodiment of this aspect of the present invention, the at least one species of nucleic acid or protein is immobilised on a carrier material before or during the addition of the nitrogenous compound. The carrier materials described already in connection with other aspects of the present invention can again be used thereby.

In a further preferred embodiment of this method according to the invention, the sample preparation is carried out in such a manner that the at least one species of the nucleic acid and/or of the protein is dissolved and/or suspended in the fluid sample preparation. This can particularly be effected by the addition of suitable amounts of the nitrogenous compound to the sample. If a lysis of a biological sample is effected by the addition of the composition, the lysis can correspondingly be carried out in such a manner that at least one species of the nucleic acid/and or of the protein is dissolved and/or suspended in the fluid sample preparation.

In a further preferred embodiment of the method according to the invention, the sample is a biological sample in which the at least one species of a nucleic acid and/or at least of a protein is contained in a casing, e.g. a biological casing, and whereby the sample is contacted with the fluid or solid composition to produce a lysate. The sample can also contain organisms. The lysate is preferably generated for the lysis of a biological sample according to the method according to the invention described above.

As already described above in the stabilisation method according to the invention, the sample contains, in a preferred embodiment of the method according to the invention, at least two species from the group consisting of nucleic acids and proteins for the decrease of inhibiting effects, and the generation of the sample preparation or the lysis is carried out in such a manner that a plurality of the species of nucleic acid and/or proteins contained in the sample are dissolved and/or suspended or immobilised in the sample preparation or the lysate. Preferably, essentially all of these species are dissolved and/or suspended or immobilised in a variant of the method. Thereby, either all of the species of nucleic acids contained in the sample or all of the species of proteins contained in the solution can be dissolved and/or suspended or immobilised. The implementations made above in connection with the analog embodiment of the stabilisation method apply here in the same manner.

This means that essentially no precipitation takes place during the generation of the sample preparation or the lysis, as is used e.g. for the removal of nucleic acids or proteins from lysates. If the sample contains several species of nucleic acid and/or proteins, and two, several or all of these species shall remain dissolved and/or suspended in the lysate after the lysis, it is particularly preferred that the relative concentration of these different species of nucleic acids and/or proteins do not change with regard to one another by the lysis and thereby the relative concentration of these species in the lysate remains essentially unchanged with regard to the relative concentration of this species in the sample. It again applies, as already disclosed above, to consider the type of the sample and the different possibly used ysis reagants and the type of the used nitrogenous compound during the execution of the lysis and that suitable routine tests have possibly to be carried out, to determine suitable conditions for a given sample type. Suitable routine tests have to be carried out if necessary, so as to determine suitable conditions for a given sample type.

In the method according to the invention for decreasing inhibiting effects, a preferred embodiment provides that DNA and/or RNA is contained in the lysate, in particular dissolved and/or suspended. Additionally or alternatively, at least one species of protein can be contained in the lysate, in particular be dissolved or suspended.

As has already been described above in connection with the method according to the invention for the lysis of a biological sample, the composition used for the lysis can contain at least a reagant of the group of the complexing agents, detergents, substances for volume restriction and/or solvents as further lysis reagants. The lysis can also take place under mechanical action and/or in an enzymatic manner, or the sample can be washed with a hypotonic washing buffer before the lysis. The implementations made above in connection with the lysis method according to the invention apply here in the same manner.

In the stabilisation method according to the invention, the amount of the nitrogenous compound which is added to the sample, is preferably chosen in such a manner that the concentration of the nitrogenous compound in the produced sample preparation or the lysate is between 0.001 mM to 1 M, preferably between 0.001 to 100 mM, particularly preferably between 0.001 to 50 mM or 0.001 to 30 mM and specially 0.001 to 10 mM. If polyamines (a) are used, the concentration is preferably between 0.001 mM and 15 mM, preferably between 0.001 to 1 mM. During the use of amino acids (b), the concentration can preferably be in the region of 0.001 mM to 20 mM, in particular in the region of 1 to 15 mM. During the use of nitrogenous heterocycles (c), the concentration can preferably be between 0.001 to 50 mM, preferably 0.001 to 30 mM. During the use of carboxylic acid amines, (e), the concentration can preferably be between 0.001 to 20 mM. If inorganic ammonium compounds are used, the concentration can preferably be between 0.001 mM to 100 mM, in particular preferably from 0.001 to 50 mM. During the use of antibiotica binding nucleic acid, the concentration can preferably be 0.001 to 15 mM, in particular preferably 0.001 to 1 mM.

In a particularly preferred embodiment of the method according to the invention for the decrease of inhibiting effects, the at least one nucleic acid species is a DNA species, in particular gDNA and/or a RNA species.

Regarding the type of the nitrogenous compounds, which can preferably be used in the method according to the invention for reducing inhibiting effects, the implementations made above with regard to the lysis method according to the invention or the stabilisation method according to the invention apply in the same manner.

In a further aspect, the present invention relates to an analysis method for the detection of at least one species of nucleic acid and/or proteins in a sample, whereby the method comprises the following steps: a) providing a sample preparation or a lysate, according to the invention, which contains at least one species of a nucleic acid and/or at least of a protein, whereby the sample preparation or the lysate were decreased with at least one inhibiting effect with the method according to the invention for decreasing inhibiting effects;
b) use of the sample preparation in a reaction or reaction sequence suitable for the detection of the at least one nucleic acid or the at least one protein.

By this method, due to the decrease of the inhibiting effects in the sample preparation or the lysate, an improved detection of the species to be analysed can be achieved, whereby a sample reconditioning preceding the detection reaction for the separation of the inhibiting substance can be foregone.

In a preferred embodiment of this analysis method according to the invention, the sample preparation or the lysate in step b) is correspondingly used directly, without carrying out further method steps for the reduction of the number of species of nucleic acid and/or proteins contained in the sample preparation or that further steps for the removal of substances, which effect the degradation of nucleic acids and/or proteins have to be carried out from the sample preparation, or that such substances have to be inactivated. The sample preparation or the lysate is thereby preferably used directly for the analysis or for the production of a reaction solution suitable for the analysis, without any further reconditioning step.

In a further embodiment, the lysis can be supported by the above-mentioned methods for the physical, chemical or enzymatic lysis. In particular, lysis methods with physical support by heating or homogenisation of the lysate, with chemical support by the use of detergents or enzymatic support by the use of proteases as e.g. protease K (if protein is not to be detected), lysozyme or also nucleases (e.g. DNase; in this case DNA cannot be detected) have proved to be suitable.

In an embodiment of this method, the stabilisation of nucleic acid by one of the chosen substances is carried out following an enzymatic, physical or chemical lysis, in particularly preferred using detergents and protease as e.g. proteinase K. Thus, detergents with a concentration of 0.005 to 10% are e.g. used. Proteases as e.g. the proteinase K can be contained in the stabilised sample in a concentration of $0.5 \times 10^{-4}$ mAU/µl to $50 \times 10^{-4}$ mAU/µl.

In a further embodiment of this method, the decrease of the inhibiting effect is carried out by one or more of the claimed substances. A nucleic acid degradation can in particular be improved by one of the substances. The DNase I can thus degrade DNA in a concentration of 0.003 to 0.5 U/µl in the sample.

In a further embodiment of this method, the stabilisation of biomolecules is carried out in the sample e.g. of nucleic acid or protein by one or several of the claimed substances chosen from e.g. treatment of the at least two species of biomolecule is carried out in the sample through a substance chosen from e.g. arginine, imidazole, proline, lysine, spermine, spermidine, glutamic acid, indazole, thymine, thymidine, guanine, guanosine, adenine, histidine, tryptophane, ammonium sulfate or by a mixture of these.

Regarding the type of the reaction or reaction sequence used for the detection of the corresponding species of nucleic acid and/or protein, the implementations made above with regard in connection with the lysis according to the invention apply here.

In a particularly preferred embodiment of this analysis method according to the invention, the sample preparation or the lysate contains RNA in addition to gDNA and the reaction sequence in step b) optionally comprises the reaction of nucleic acids with enzymes. These reactions can be in particular: b1) optional degradation of gDNA and successively b2) RT-PCR, preferably real-time RT-PCR for the detection of RNA. The lysate can alternatively contain RNA in addition to gDNA and the reaction or the reaction sequence in step b) comprises the following steps: b1) PCR, preferably real-time RT-PCR for the detection of gDNA or b2) RT-PCR, preferably real-time RT-PCR for the detection of RNA. The PCR or RT-PCR can thereby optionally proceed as end point, as multiplex and/or as real-time reaction.

In one embodiment of the method according to the invention, a first conversion product of a chosen nucleic acid is provided with the analysis method, e.g. first strand cDNA from RNA.

Regarding the above explained method for decreasing of inhibiting effects in a sample, the nitrogenous compound contained in the sample preparation or the lysate can also lead to an additionally improved lysis, a stabilisation of certain species of nucleic acid and/or proteins and to a masking of certain nucleic acids.

In a further aspect, the present invention relates to a method for the selective masking of at least one species of a nucleic acid in a sample, which contains at least one first species of a nucleic acid and a second species different to the first species. This method comprises the following steps:

A) providing a sample which contains at least two different species of nucleic acid, B) contacting the sample with a fluid or solid composition to produce a fluid sample preparation, whereby the composition contains at least a nitrogenous compound, which is selected from the group consisting of:

a) polyamines, b) amino acids and oligo and polypeptide, c) nitrogenous heterocylischic compounds, including homo or heteropolymeres, which comprise these nitrogenous compounds, d) amines of the type $R^1R^2NR^3$, whereby $R^1$, $R^2$ and $R^3$ are chosen different from one another from the group consisting of H, $C_1$-$C_5$-alkyl groups and aryl groups, whereby $R^1$, $R^2$ and $R^3$ are not H simultaneously, e) carboxylic acid amides, f) inorganic ammonium salts, g) ammonium groups containing inner salt compounds, h) antibiotica binding nucleic acid, i) compounds, which bind in the small cavity of the DNA, j) nitrogenous compounds chosen from the groups described under a-i with an additional derivation, and mixtures of two or more of these compounds, whereby the generation of the sample preparation is carried out in such a manner that a first and a second species of nucleic acid is dissolved and/or suspended in the fluid sample preparation and whereby the amount of the nitrogenous compound is chosen in such a manner, that the second species of nucleic acid is masked in such a manner that the first species of nucleic acid can be detected in an improved manner in a detection method for nucleic acids, compared to the same detection method, where the nitrogenous compound was not added to the sample.

A simple differential analysis of the second species of nucleic acid in the sample is enabled by this method. In this method, the first species of nucleic acid, which cannot be analysed in the differential analysis, but which potentially could disturb or falsify the detection reaction of the second species, can be systematically masked in the sample. A separation of the first or second species of nucleic acid from the sample can thereby be foregone.

In other words, the differential analysis of DNA and RNA results e.g. in a differential masking of DNA or RNA, so that the masked nucleic acid cannot be detected within the analysis or with low efficiency, or does not influence the result of the analysis of the second species in a negative manner.

In preferred embodiments of the masking method according to the invention, the sample is a biological sample, which is subjected to a lysis and possibly further purification steps prior to the contacting with the composition for the generation of the fluid sample preparation of a lysis. In a further preferred embodiment, the sample is a biological sample in which the species of nucleic acids are contained in a casing, preferably a biological casing, and whereby the sample is contacted with the fluid or solid composition to produce a lysate. In a further preferred embodiment, the sample contains at least two species of nucleic acid and the generation of the sample preparation or the lysis is carried out in such a manner that several certain species of nucleic acid and/or proteins are dissolved or suspended in the generated lysate. It is further preferred that the sample contains at least two species of nucleic acid and the generation of the sample preparation or the lysis is carried out in such a manner that essentially all or a plurality of the species of nucleic acid contained in the sample are dissolved and/or suspended in the sample preparation or in the lysate. It is further preferred that the composition which contains the nitrogenous compound, contains at least a reagant of the group of the complexing agents, detergents, substances for volume restriction and/or solvents as further lysis reagents. The lysis can also take place under mechanical action and/or in an enzymatic manner, or the sample can be washed with a hypotonic washing buffer before the lysis. Regarding all these preferred embodiments, the embodiments made above in connection with the lysis method according to the invention and the stabilisation method according to the invention or the method according to the invention for the reduction of inhibiting effects apply.

In further preferred embodiments of the method according to the invention for the selective masking is:

a) the first species of nucleic acid and the second species of nucleic acid a species of RNA or PNA; or b) the first species of nucleic acid is a species of RNA and the second species of nucleic acid is a species of DNA; or c) the first species of nucleic acid is a species of PNA and the second species is a species of DNA or RNA, c) the first species of nucleic acid and the second species of nucleic acid are a species of DNA, or c) the first species of nucleic acid and the second species of nucleic acid are a species of RNA, or e) the first species of nucleic acid and the second species of nucleic acid are nucleic acid PNA.

In preferred embodiments of the method according to the invention for the selective masking, the amount of the nitrogenous compound in the generation of the sample preparation or the lysate in such a manner that the concentration of the nitrogenous compound in the generated sample preparation or the lysate is between 0.001 mM to 1 M, preferably 0.001 mM to 100 mM, in particular preferably 0.001 to 30 mM, especially 0.001 to 19 mM or 0.001 to 15 mM. During the use of polyamines (a), in particular spermidine for the selective masking of DNA, e.g. gDNA, preferably compared to RNA, the concentration is preferably 0.001 to 10 mM, preferably 0.001 to 1 mM. During the use of amino acids (b) for the selective masking of DNA, e.g. gDNA, preferably compared to RNA, the concentration can preferably be 0.001 to 50 mM, in particular preferably 0.001 to 30 mM. During the use of nitrogenous heterocyclic compounds for the masking of DNA, e.g. gDNA, preferably compared to RNA, the concentration can preferably be 0.001 to 30 mM, preferably 0.001 to 20 mM. During the use of anporganic ammonium compounds for the masking of DNA, e.g. gDNA, preferably compared to RNA, the concentration can preferably be 0.001 to 50 mM, preferably 0.001 to 30 mM. During the use of carboxylic acid amides for the masking of DNA, e.g. gDNA, preferably compared to RNA, the concentration can preferably be 0.001 to 20 mM, preferably 0.001 to 10 mM. The concentration to be chosen can be influenced by the type of the sample and has possibly to be considered as well.

Regarding the type of the nitrogenous compounds, which can preferably be used in the method according to the invention for reducing inhibiting effects, the implementations made above with regard to the lysis method apply in the same manner.

In a further aspect, the present invention relates to an analysis method for the detection of at least one species of nucleic acid and/or proteins in a sample, whereby the method comprises the following steps:

a) providing a sample preparation which contains at least a first species of nucleic acid and a second species of nucleic acid, and whereby the first species of nucleic acid is different from the second species of nucleic acid, whereby the first species of nucleic acid was masked with the method for the selective masking according to the invention and b) use of the sample preparation or the lysate in a reaction or reaction sequence suitable for the detection of the second nucleic acid.

The analysis method according to the invention can be carried out by the selective masking without a previous separation of the possibly the analysis of a second species of nucleic acid influencing the first species of nucleic acid in a disadvantageous manner. The analysis method is improved and simplified thereby, elaborate separation steps to be carried out before the analysis can be omitted.

In a preferred embodiment of the analysis method according to the invention, step b) is carried out without carrying out further method steps for the reduction of the number of species of nucleic acid contained in the sample preparation and/or without further steps for the removal of materials from the sample preparation which effect the degradation of nucleic acids or without further method steps for the inactivation of those substances in the sample preparation. The sample preparation or the lysate is preferably used directly without a further reconditioning step in the reaction or the reaction sequence for the detection of the second nucleic acid species or for the production of a reaction solution suitable for the analysis. The sample preparation for the detection of a certain species of nucleic acid is thereby considerably simplified, whereby the expenditure of time and the costs and error susceptibility of the analysis method can be reduced.

Regarding the type of the reaction or reaction sequence used for the detection of the corresponding species of nucleic acid, the implementations made above in connection with the previously described aspects of the present invention, e.g. the lysis according to the invention, apply.

In a particularly preferred embodiment of the differential analysis method, the reaction or reaction sequence used in step b) for the detection of the second species of nucleic acid is a PCR or RT-PCR, preferably a real-time PCR or real-time RT-PCR. Preferably, the first species of nucleic acid is gDNA and the second species of nucleic acid is RNA in the sample preparation or in the lysate, and in step b) the reaction or the reaction sequence is a RT-PCR, preferably a real-time RT-PCR. There, the nitrogenous compound selected from the group of the polyamines, heterocycles, amino acids, carboxylic acid amides and ammonium compounds described above with regard to the lysis method according to the invention, preferably compounds selected from the group consisting of spermidine, ammonium sulfate, ammonium hydrogen phosphate, glycine, 2,3-dimethylpyrazine, benzimidazole, imidazole, arginine, histidine, urea and distamycine, in particular distamycine D.

In a further preferred embodiment of the differential analysis method according to the invention, the first species of nucleic acid RNA and the second species of nucleic acid is DANN, preferably gDNA in the sample preparation or in the lysate. In step b), the reaction or the reaction sequence is a RT-PCR, preferably a real-time RT-PCR. Preferably, the compound described here in connection with the lysis method according to the invention selected from the group of the heterocycles, amino acids and ammonium compounds are used here, which a particularly selected from the group consisting of proline, indazole and ammonium sulfate.

The present invention will be explained in more detail in the following with chosen examples and the corresponding figures. The examples serve the purpose of the clarification of the present invention and are not to be seen as restricting.

In a further aspect, the present invention relates to an analysis method for the detection of at least one species of DNA in a sample, whereby the method comprises the steps:

a) providing a sample preparation or a lysate, which contains at least one species of a RNA, whereby the at least one species of RNA was treated with at least one of the substances in a sample preparation according to the invention, and b) use of the sample preparation in a reaction or reaction sequence suitable for the detection of the at least one species of RNA. The sample preparation is preferably used directly, without carrying out further method steps for the reduction of the number of the species of nucleic acids and/or proteins contained in the sample preparation and/or for the removal or inactivation of the substances from the sample preparation effecting the degradation of nucleic acids and/or proteins.

In one embodiment of this method, the treatment of the at least one species of RNA is carried out by one of the chosen substances, when the RNA is contained in organisms, in particular in single cells, cell assemblies, tissues or whole animals or plants, cultivated cells, or excretion products or secretions as e.g. stabilised and non-stabilised blood, plasma, serum, tissue fluids, sperm, swabs, sputum, saliva, tear fluid, urine, excrements, hair, danders, bacteria, viruses etc.

In one embodiment of the method according to the invention, the above-mentioned organisms can be pretreated with a washing solution before the treatment with the substances according to the invention. Particularly preferred, a washing solution is used which removes contaminations and/or prepares the sample for the treatment with the substances according to the invention in another manner.

By this method, an improved detection and/or a reaction can be achieved due to the treatment of the species of RNA to be detected.

Regarding the type of the reaction or reaction sequence used for the detection of the corresponding species of RNA, the implementations made above in connection with the lysis according to the invention apply.

In a further embodiment of the method according to the invention, the organisms are incubated with the lysis buffer, preferably between 1 to 120 minutes. In a further embodiment of the method according to the invention, the organisms are incubated with the lysis buffer at a temperature which is increased compared to room temperature, preferably at 30 to 90° C., particularly preferably at 50 to 85° C.

In a further embodiment of this method, the treatment of the at least one species RNA is carried out by one of the chosen substances, during or after an enzymatic, physical or chemical lysis, in particular preferred using detergents and protease as e.g. proteinase K. Thus, detergents with a concentration of 0.005 to 10% are used for example. Proteases as e.g. the proteinase K can be contained in the stabilised sample in a concentration of $0.5 \times 10^{-4}$ mAU/µl to $50 \times 10^{-4}$ mAU/µl.

In a further embodiment of this method, the treatment of the at least one species RNA is carried out by one of the chosen substances during or after an enzymatic degradation of DNA by an endonuclease as e.g. DNase. The DNase I can thus be contained in the stabilised sample in a concentration of 0.003 U/µl to 0.5 u/µl.

In a further embodiment of the method according to the invention, the enzymes are deactivated after an enzymatic treatment, for example by increasing the temperature, for example to 60 to 95° C.

In a further embodiment of this method, the treatment of the at least one species of RNA is carried out by one of the chosen substances and a physocal treatment step, in particular preferred by shear forces, pressure differences or temperature influence.

In a further embodiment of this method, the treatment of the at least one species of RNA is carried out in the sample by one or more of the claimed substances chosen from e.g.

arginine, imidazole, proline, lysine, spermine, spermidine, glutamic acid, indazole, thymine, thymidine, guanine, guanosine, adenine, histidine, tryptophane, ammonium sulfate or by a mixture of these.

In a further embodiment of this method, the treatment of the at least one species of RNA is carried out in a solution which contains at least one of the described substances, whereby the solution comprises a pH between 7.1 and 14, preferably a pH between 7.1 and 12, and especially preferably a pH between 7.4 and 10.

The reaction or reaction sequence suitable for the detection of the at least one species of RNA can thereby e.g. be selected from the group of the nucleic acid binding reactions, in particular the nucleic acid hybridisations, in particular polymerisations of nucleic acids and in particular the group of the amplification reactions. In a particular embodiment of this method, the detection method of the at least one species of RNA is a PCR (polymerase chain reaction), real-time-PCR (as probe-based method and as a method which depends on a sequence-unspecific binding detector molecule as e.g. SybrGreen), RT-PCR (reverse transcription polymerase chain reaction), Real-time-RT-PCR (as probe-based method and as a method which depends on a sequence-unspecific binding detector molecule as e.g. SybrGreen), multiplex PCR, multiplex RT-PCR, the probe-based methods of the real-time multiplex PCR and real-time multiplex RT-PCR. The term RT-PCR in the described connection is to be understood as follows: The reaction of the RT-PCT consists of a reverse transcription and a PCR, whereby both reactions can take place independently from one another in two separate containers or together in one container. Both reactions can be carried out by one or more enzymes. In addition to the RT-PCR, other reactions can also be carried out with the lat least one species of RNA as e.g. NASBA (nucleic acid sequence based amplification), 3SR (sequence sustained self replication), 2SR, TMA (transcription mediated amplification), MDA (multiple displacement amplification), rolling circle amplification, whole-transcriptome-amplification, whole-genome-amplification and rolling transcription amplification or loop-mediated isothermal amplification (LAMP).

In a further aspect, the present invention relates to an analysis method for the detection of at least one species of DNA in a sample, whereby the method comprises the steps:
a) providing a sample preparation or a lysate which contains at least one species of a DNA, whereby the at least one species of DNA was treated with at least one of the substances according to the invention in a samplre preparation, and
b) use of the sample preparation in a reaction or reaction sequence suitable for the detection of the at least one species of a DNA. The sample preparation is preferably used directly, without carrying out further method steps for the reduction of the number of the species of nucleic acids and/or proteins contained in the sample preparation before the detection reaction and/or for the removal or inactivation of the substances from the sample preparation effecting the degradation of nucleic acid and/or proteins.

In one embodiment of this method, the treatment of the at least one species of DNA is carried out by one of the chosen substances, when the DNA is contained in organisms, in particular in single cells, cell assemblies, tissues or whole animals or plants, cultivated cells, or excretion products or secretions as e.g. stabilised and non-stabilised blood, plasma, serum, tissue fluids, sperm, swabs, sputum, saliva, tear fluid, urine, excrements, hair, danders, bacteria, viruses etc.

In one embodiment of the method according to the invention, the above-mentioned organisms can be pretreated with a washing solution before the treatment with the substances according to the invention. Particularly preferred, a washing solution is used which removes contaminations and/or prepares the sample for the treatment with the substances according to the invention in another manner.

By this method, an improved detection and/or reaction can be achieved due to the treatment of the species of DNA to be detected.

Regarding the type of the reaction or reaction sequence used for the detection of the corresponding species of DNA, the implementations made above in connection with the lysis according to the invention apply.

In a further embodiment of the method according to the invention, the organisms are incubated with the lysis buffer, preferably between 1 to 120 minutes. In a further embodiment of the method according to the invention, the organisms are incubated with the lysis buffer at a temperature which is increased compared to room temperature, preferably at 30 to 100° C., particularly preferably at 50 to 85° C.

In a further embodiment of this method, the treatment of the at least one species DNA is carried out by one of the chosen substances carried out before, during or after an enzymatic, physical or chemical lysis, in particular preferred using detergents and protease as e.g. proteinase K. Thus, detergents with a concentration of 0.005 to 10% are used. Proteases as e.g. the proteinase K can be contained in the stabilised sample in a concentration of $0.5 \times 10^{-4}$ mAU/µl to $50 \times 10^{-4}$ mAU/µl.

In a further embodiment of this method, the treatment of the at least one species DNA is carried out by one of the chosen substances subsequent to an enzymatic degradation of RNA by an endonuclease as e.g. RNase.

In a further embodiment of the method according to the invention, the enzymes are deactivated after an enzymatic treatment, for example by increasing the temperature, for example to 60 to 100° C.

In a further embodiment of this method, the treatment of the at least one species of DNA in the sample is carried out by a substance chosen of e.g. tryptophane, proline, histidine or guanosine or by a mixture of these.

In a further embodiment of this method, the treatment of the at least one species of DNA is carried out in a solution which contains at least one of the described substances, whereby the solution comprises a pH between 7.1 and 14, preferably a pH between 7.1 and 12, and especially preferably a pH between 7.4 and 10.

In a further embodiment of this method, the treatment of the at least one species of DNA is carried out through one of the chosen substances and a physical treatment step, particularly preferred by temperature influence.

The reaction or reaction sequence suitable for the detection of the at least one species of DNA can thereby be selected from e.g. the group of the nucleic acid binding reactions, in particular the nucleic acid hybridisations, in particular polymerisations of nucleic acids and in particular of the group of the amplification reactions. In a particular embodiment of this method, the detection method of the at least one species of RNA is a PCR (polymerase chain reaction), real-time-PCR (as probe-based method and as a method which depends on a sequence-unspecific binding detector molecule as e.g. SybrGreen), multiplex PCR, multiplex RT-PCR, the probe-based methods of the real-time multiplex PCR and real-time multiplex RT-PCR. In addition to the PCR, other reactions can also be carried out with the at least one species of DNA as e.g. MDA (multiple displacement amplification), rolling circle amplification, whole-genome-amplification and rolling transcription amplification or loop-mediated isothermal amplification (LAMP).

In a further aspect, the present invention relates to an analysis method for the detection of at least two species of biomolecules, for example at least one species of a nucleic acid and at least one species of a protein in a sample, whereby the method comprises the following steps:

a) providing a sample preparation or a lysate which contains at least two species of biomolecules, for example at least one species of a nucleic acid and at least one species of a protein, whereby the at least one species of nucleic acid and/or protein was treated with at least one of the substances according to the invention, and b) use of the sample preparation in a reaction or reaction sequence suitable for the detection of at least two species of biomolecules, for example at least one species of a nucleic acid and one species of protein. The sample preparation is preferably used directly, without carrying out further method steps for the reduction of the number of the species of nucleic acids and/or proteins contained in the sample preparation and/or for the removal or inactivation of the substances from the sample preparation effecting the degradation of nucleic acids and/or proteins.

In one embodiment of this method, the treatment of nucleic acids and/or proteins is carried out by one of the chosen substances, when the nucleic acid and/or protein is contained in organisms, in particular in single cells, cell assemblies, tissues or whole animals or plants, cultivated cells, or excretion products or secretions as e.g. stabilised and non-stabilised blood, plasma, serum, tissue fluids, sperm, swabs, sputum, saliva, tear fluid, urine, excrements, hair, danders, bacteria, viruses etc.

In one embodiment of the method according to the invention, the above-mentioned organisms can be pretreated with a washing solution before the treatment with the substances according to the invention. Particularly preferred, a washing solution is used which removes contaminations and/or prepares the sample in another manner for the treatment with the substances according to the invention.

By this method, nucleic acids and/or proteins can be detected likewise in a reaction due to the treatment in a treated sample.

By this method, RNA and DNA or RNA and proteins or DNA and proteins can be detected due to the treatment in a treated sample.

Regarding the type of the reaction or reaction sequence used for the detection of the corresponding species of nucleic acid and/or protein, the implementations made above in connection with the lysis according to the invention apply.

In one embodiment of this method for the detection of RNA and DNA in a treated sample, the treatment of the nucleic acids with one of the chosen substances is carried out before, during or after an enzymatic, physical or chemical lysis, in particular preferred using detergents and protease as e.g. proteinase K. Thus, detergents with a concentration of 0.005 to 10% are e.g. used. Proteases such as e.g. the proteinase K can be contained in the stabilised sample in a concentration of $0.5 \times 10^{-4}$ mAU/µl to $50 \times 10^{-4}$ mAU/µll.

In one embodiment of this method for the detection of RNA and protein in a treated sample, the treatment of the nucleic acids with one of the chosen substances is carried out before, during or after an enzymatic, physical or chemical lysis, in particular preferred using detergents and/or DNA-specific nuclease. Thus the DNase I can be contained in the stabilised sample in a concentration of 0.003 U/µl to 0.5 U/µl.

In one embodiment of this method for the detection of DNA and protein in a treated sample, the treatment of the nucleic acids with one of the chosen substances is carried out before, during or after an enzymatic, physical or chemical lysis, in particular preferred using detergents and/or RNA-specific nuclease.

In a further embodiment of the method according to the invention, the organisms are incubated with the lysis buffer, preferably between 1 to 120 minutes. In a further embodiment of the method according to the invention, the organisms are incubated with the lysis buffer at a temperature which is increased compared to room temperature, preferably at 30 to 85° C., particularly preferably at 50 to 80° C.

In a further embodiment of this method, the treatment of the at least two species of biomolecule is carried out in the sample through a substance chosen from e.g. arginine, proline, or imidazole or a mixture of these.

In a further embodiment of this method, the treatment of the sample is carried out in a solution which contains at least one of the described substances, whereby the solution comprises a pH between 7.1 and 14, preferably a pH between 7.1 and 12, and especially preferably a pH between 7.4 and 10.

Thereby, the reaction or reaction sequence suitable for the detection of the at least one species of nucleic acid can be selected from the group of the nucleic acid binding reactions, in particular the nucleic acid hybridisations, in particular polymerisations of nucleic acids and in particular of the group amplification reactions. In a particular embodiment of this method, the detection method of the at least one species of RNA is a PCR (polymerase chain reaction), real-time PCR (as probe-based method and as a method which depends on a sequence-unspecific binding detector molecule as e.g. SybrGreen), RT-PCR (reverse transcription polymerase chain reaction), Real-time-RT-PCR (as probe-based method and as a method which depends on a sequence-unspecific binding detector molecule as e.g. SybrGreen), multiplex PCR, multiplex RT-PCR, the probe-based methods of the real-time multiplex PCR and real-time multiplex RT-PCR. The term RT-PCR is to be understood as follows in the described connection: The reaction of the RT-PCR consists of a reverse transcription and a PCR, whereby both reactions can take place independently from each other in two separate containers or together in one container. Both reactions can be carried out by one or more enzymes. In addition to the RT-PCR, other reactions can also be carried out with the at least one species of RNA as e.g. NASBA (nucleic acid sequence based amplification), 3SR (sequence sustained self replication), 2SR, TMA (transcription mediated amplification), MDA (multiple displacement amplification) rolling circle amplification, whole-transcriptome-amplification, whole-genome-amplification and rolling transcription amplification or loop-mediated isothermal amplification (LAMP).

The reaction or reaction sequence suitable for the detection of the at least one protein is selected from the group of the protein binding reactions, in particular protein recognition, in particular by other proteins, reactions based on the enzymatic activity of the protein, antibodies, aptameres, ligands, nucleic acids, in particular Western blotting, or other substances such as gluathione and NAD, or is selected from the group of the protein modification or processing, in particular (de)phosphorylation, (de)glycolysation and splitting through proteases.

All methods mentioned above can be carried out either in solution, suspension or solid phase.

BRIEF DESCRIPTION OF DRAWINGS

FIG. 10.a.1: and

FIG. 10.a.2: the connection between the Ct value and the factor by means of idealised hypothetic values.

FIG. 11: a diagram showing the concentration dependence of the measured Delta Ct value.

DETAILED DESCRIPTION OF A PREFERRED EMBODIMENT

Examples

Figure 1:
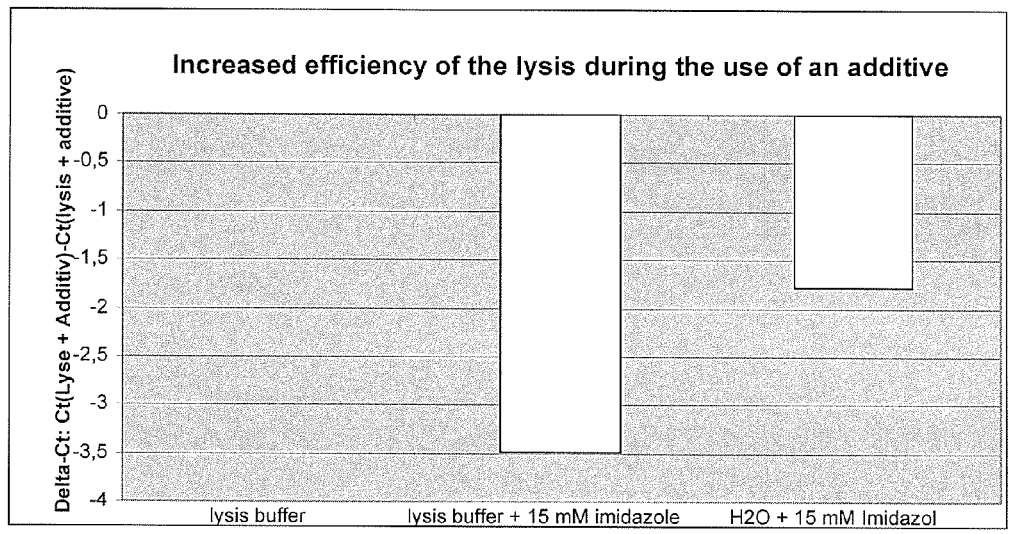
FIG. 1: a diagram in which the Delta CT values of different samples which were lysated with and without a nitrogenous compound (additives) are compared.

In the following examples, the nitrogenous compounds as defined in the present invention in the claims are called additive.

Insofar it is not described otherwise in the following, the following materials were used in the examples:
Parent Solutions:
(1) 500 mM EGTA, pH 8
(2) 500 mM EGTA, pH 8
(3) TE-Buffer, 10 mM Tris-HCl, 1 mM EDTA, pH 7.5
(4) EPE: 0.06 vol-% Nonidet P40, 1 mM EDTA, 1 mM EGTA, 0.1 vol-% polyethylene glycol MG 6000 (PEG)
Devices:
(1) ABI Prism 7700 (ABI, Foster City, Calif., USA) (Real-time-RT-PCR)
(2) PCR-ThermoCycler (Biometra GmbH, Gottingen, Germany)
(3) Spectrophotometer for determining the concentration of DNA or RNA (Beckman DU 7400, Beckman Coulter Inc., Fullerton, Calif., USA)
(4) Agilent Bioanalyzer (Agilent, USA) (denatured gel analysis)
Cell Cultures:
(1) HeLa cells
(2) 293 cells
(3) HUH 7 cells
(4) NIN3T3 cells
(5) HepG2 cells
(6) MCF7 cells
Media:
(1) D-MEM (BRL; USA) partially with the additives 10% FCS, 1% Pen/Strept and/or 1% non-essential amino acids for the cells Hela, HUH7, 293, NIH3T3
(2) RPMI 1640 (BRL; USA) partially with the additives 10% FCS, 1% glutamine and/or 1% PEN/Strept for HepG2 cells
(3) RPMI 1640 (BRL; USA) partially with the additives 10% FCS, 1% sodium pyruvate, 1% glutamine, 1% Pen/Strept, 1% non-essential AS and/or 0.25% bovine insulin for MCF7 cells
Kits and Enzymes:
(1) RNeasy®: RNA preparation method of QIAGEN GmbH, Hilden, Germany
(2) RNeasy 96®: RNA preparation method of QIAGEN GmbH, Hilden, Germany
(3) Omniscript® RT-Kit: Kit for the reverse transcriptase reaction of RNA (QIAGEN GmbH, Hilden, Germany)
(4) Sensicript® RT-Kit: Kit for the reverse transcriptase reaction of RNA (QIAGEN GmbH, Hilden, Germany)
(5) QuantiTect® SybrGreen PCR Kit: Kit for the real-time PCR with SybrGreen (QIAGEN GmbH, Hilden, Germany)
(6) QuantiTect® sample PCR Kit: Kit for the real-time PCR with marked probes (QIAGEN GmbH, Hilden, Germany)
(7) DNase I: (QIAGEN GmbH, Hilden, Germany)
Transcripts and Genome-Loci which were Tested in Real-Time RT-PCR or PCR:
(1) β-Actine: as transcript and genome locus
(2) GAPDH as transcript and genome locus
(3) β-Tubuline as transcript
DNase I Verdau (Example 10 and 11):
In the examples 10 and 11, the DNase I Verdau was carried out as follows: The DNase I Verdau was the lysate was carried out prior to the real-time PCR. For this, 2 µl of the lysates was digested in a 20 µl volume in a suitable buffer which contained 150 µM $CaCl_2$, 4 mM $MgCl_2$ and 50 mM Tris pH 8.4, with 2 units (units) DNase I. The reaction was stopped by adding an EDTA/EGTA solution. Then, 2 µl of the reaction solution was entered into the real-time PCR to measure the amount of the remaining gDNA.

I. Lysis

Example 1

Lysis of Cells in the Presence of Different Additives

It is demonstrated with this experiment that the lysis of cells can be made more efficient by the addition of an additive. For this, cells were lysed in a lysis buffer which contained imidazole in a concentration of 15 mM in $H_2O$ as additive in a first experiment. In a second experiment, cells were lysed in a lysis buffer B, which contained Nonidet-P40, Polyethylenglycol, EGTA and EDTA in addition to the additive imidazole (15 mM). As a comparative example, cells were lysed in a lysis buffer C, which contained Nonidet-P40, polyethylene glycol, EGTA and EDTA. For the determination of the lysis efficiency, the CT value of the respective cellular transcripts was determined in a comparing real-time RT-PCR. The Ct value is the PCR cycle where the PRC signal is detected for the first time, that is, becomes visible. The Delta Ct value is calculated in this experiment from the difference of the Ct value after the lysis without additive and the Ct value at the lysis while using the additive imidazole. A negative Delta Ct value points to an improved lysis compared to the comparing system without additive. A positive Delta Ct value points to a lower efficiency with the lysis compared to the comparing system without additive.

Execution:

40000 293 cells were incubated in a suitable medium for 3 days. In a first experiment, the cells were lysed in a lysis buffer, which contains Nonidet-P40, polyethylene glycol, EGTA and EDTA, but no additive. In a second experiment, the cells were lysed in a lysis buffer, which contains Nonidet-P40, polyethylene glycol, EGTA, EDTA and 15 mM imidazole as additive. In a third experiment, the cells were lysed in a lysis buffer which contained imidazole dissolved in $H_2O$.

2 µl of the RNA obtained in this manner was converted with Omniscript®, obtained from the company QIAGEN, Hilden, Germany, into a standard reverse transcriptase reaction. After the completion of this reaction, 2 µl of the RT reaction solution was transferred to real-time PCRs for the detection of a certain transcript.

Result:

FIG. 1 shows a diagram in which the respectively determined Delta Ct values of the individual experiments are compared. These results show that cellular RNA showed Delta Ct values in the presence of the respective lysis buffers which contained imidazole as additive, which were about 1.5 to 3.5 Cts lower (that is higher negative values) than with the lysis using the usual lysis buffer without imidazole. This shows a distinct improvement degree during the lysis.

Example 2

Lysis of Cells in $H_2O$ using Different Nitrogenous Compounds as Additives In this example, the RNA yield with the lysis in $H_2O$ in the presence and absence of different additives is compared [lysine (1 mM), 2,3-dimethylpyrazine (15 mM), imidazole (15 mM), urea (5 mM), spermidine (1 mM)]. An increased yield of RNA points to a more efficient lysis. So as to exclude possible secondary effects, the RNAs of the respective lysates were cleaned after the lysis via RNeasy96®, obtained from the company QIAGEN, Hilden, Germany, and quantified by densitometric measurement of the concentration at 260 nm.

Execution:

20000 MCF7 cells were incubated in a suitable medium in a 96 well multititer culture pod. The cells are lysated in $H_2O$ or alternatively in $H_2O$ which contains different additives. The lysate is cleaned via RNeasy 96 (available from QIAGEN GmbH, Hilden, Germany) and measured densitometrically at a wavelength of 260 nm. The yield of RNA with the lysis with $H_2O$ without additive was normalised to a value of 100%.

Figure 2:
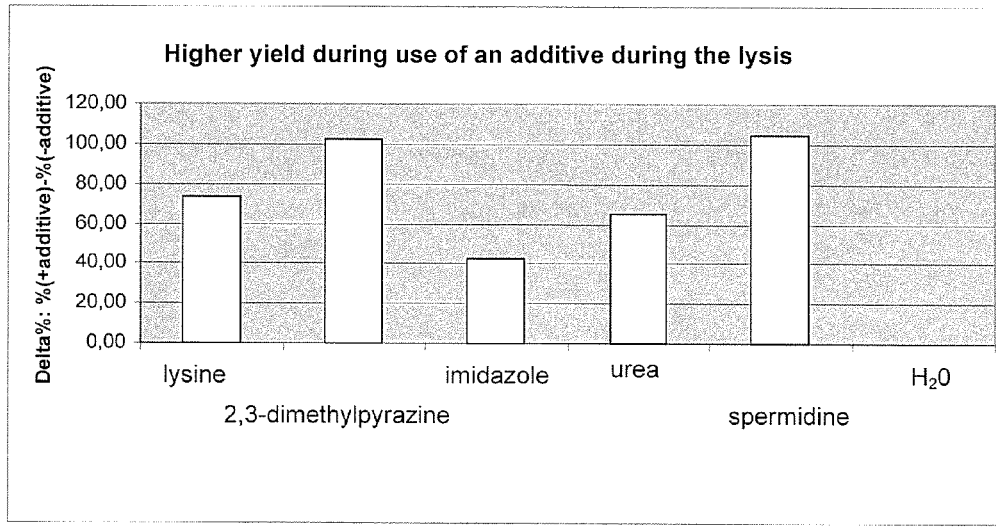
FIG. 2: a diagram for the clarification of the increase of the RNA yield which is facilitated with one embodiment of the lysis menthod according to the invention.

Result:

FIG. 2 shows a diagram in which the RNA yields are compared using different additives. It results from these results that better RNA yields are achieved by using the respective additive, which points to a more efficient lysis with the use of the additives.

Example 3

Lysis of Cells Using Lysis Buffers and Different Additives

In this example, the RNA yield in the lysis using lysis buffers in the presence and absence of different additives is compared. An increased yield of RNA points to a more efficient lysis. So as to exclude possible secondary effects, the RNAs of the respective lysates were cleaned after the lysis via Rneasy96, available from the company QIAGEN, Hilden, Germany, and quantified at 260 nm by the densitometric measurement of the concentration.

Execution:

20000 MCF7 cells are incubated in a suitable medium in a 96 well multititer culture pod. The cells are cleaned either in a lysis buffer containing Nonidet-P40, polyethylene glycol, EGTA and EDTA, or are alternatively lysed in a lysis buffer which contains, in addition to the mentioned reagents, an additive [arginine (5 mM), lysine (1 mM), 2,3-dimethylpyrazine (15 mM), imidazole (15 mM), spermidine (1 mM), pyrimidine (15 mM), guanine (15 mM)]. The lysate is cleaned via RNeasy 96 (QIAGEN GmbH, Hilden, Germany) and subsequently measured densitometrically at a wavelength of 260 nm. The RNA yield during the lysis with the lysis buffer without additive was normalised to a value of 100%.

Figure 3:
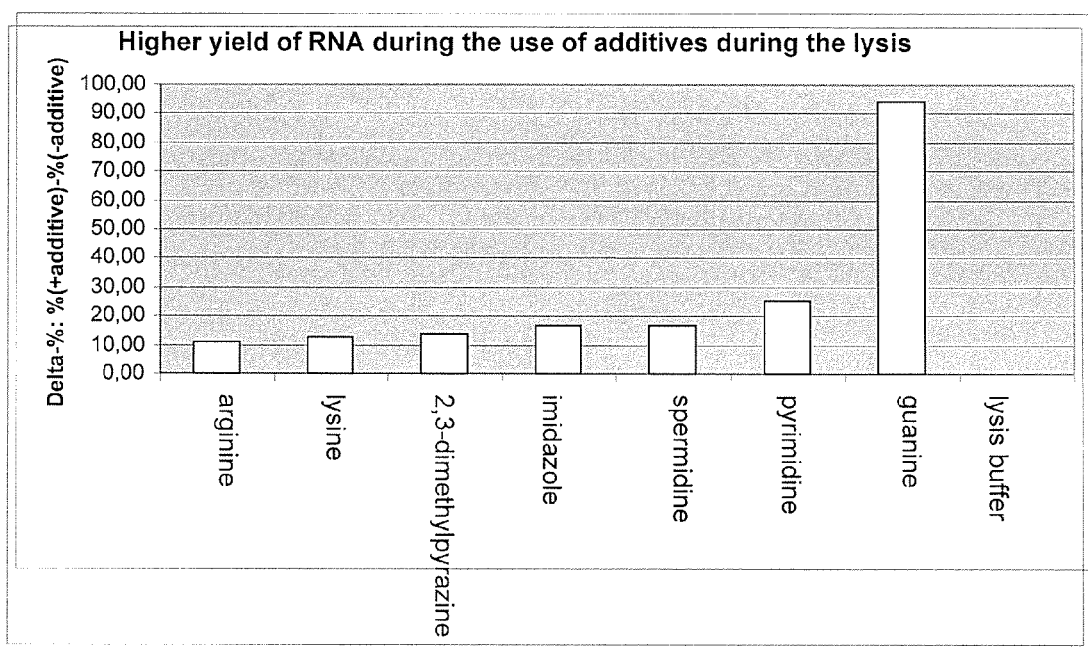
FIG. 3: also a diagram for the clarification of the increase of the RNA yield which is facilitated with one embodiment of the lysis menthod according to the invention.

Result:

FIG. 3 shows a diagram in which the RNA yields of the different experiments are compared. It can be seen from this diagram that an increased yield could be achieved with all used additives. A particularly high yield increase (about 94%) could be used here during the use of guanine as additive.

II. Stabilisation

Example 4

Stabilisation of Cellular RNA in Cell Lysates by Different Additives

Cells were lysed in a lysis buffer with or without additives. So as to determine the degree of the RNA stabilisation, the CT value of a cellular transcript was determined in a comparing real-time RT-PCR. The Ct value is the PCR cycle where the PCR signal is detected for the first time, that is, becomes visible. The Delta Ct value is calculated in this experiment from the difference of the Ct value of the samples of the lysis with additive and the Ct value of the sample of the lysis without additive. The lower, that is, the higher the amount of the negative Delta Ct value, the higher is the stabilisation effect which is effected by the addition of the additive to the lysate.

Execution:

40000 HepG2 cells were incubated in a suitable medium for 3 days. In a first experiment, the cells were lysed in a lysis buffer, which contains Nonidet-P40, polyethylene glycol, EGTA and EDTA, but no additive. In further experiments, the cells were lysed in a lysis buffer which contains, in addition to the above-mentioned lysis reagents, as an additive imidazole (15 mM), proline (15 mM), glutamic acid (15 mM), histidines (15 mM), arginines (5 mM), tyrptophane (15 mM), glycine (15 mM), pyrimidine (15 mM), guanine (15 mM), cytosine (30 mM), betaine (100 mM), ectoine (200 mM) 2,3-dimethylpyrazine (30 mM), 2-aminothiazole (15 mM), indazole (15 mM), benzimidazole (15 mM), urea (5 mM) or ammonium sulfate (30 mM). 2 µl of the RNA obtained in this manner was converted with Omniscript® (QIAGEN, Hilden, Germany) into a standard reverse transcriptase reaction. After the completion of the reverse transcriptase reaction, 2 µl of the RT reaction solution was transferred to a real-time PCRs.

Figure 4:
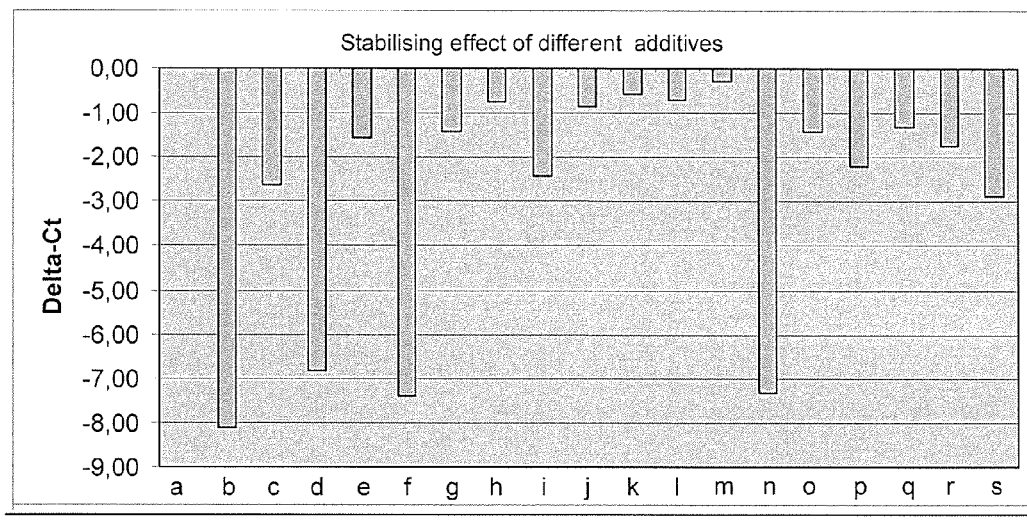
FIG. 4: a diagram showing the stabilising effect of different additives of one embodiment of the stabilisation method according to the invention.

Result:

FIG. 4 shows a diagram in which the stabilisation of cellular RNA is clarified by the different additives by means of the delta Ct value. It can be seen from the diagram that Delta Ct values in the region of 0.5-8 Cts are achieved in the presence of different concentrations of the additive. This clarifies that the stability of the RNA in a lysis buffer with additive is considerably larger compared to the use of lysis buffers which had no additive added to them.

Example 5

Stabilisation of Cellular RNA in Cell Lysates in the Presence of Additives

Cells were lysed in a lysis buffer with or without additives. So as to determine the degree of the RNA stabilisation, the CT value of a cellular transcript was determined in a comparing real-time RT-PCR. The Ct value is the PCR cycle where the PRC signal is detected for the first time, that is, becomes visible. The Delta Ct value is calculated in this experiment from the difference of the Ct value after the lysis without additive and the Ct value at the lysis while using the additive imidazole. The lower, that is, the higher the amount of the negative Delta Ct value, the higher is the stabilisation effect which is effected by the addition of the additive to the lysate.

Execution:

40000 HeLa-, HUH7 and 29293-Zellen cells were incubated in a suitable medium for 3 days. In a first experiment, the cells were lysed in a lysis buffer, which contains Nonidet-P40, polyethylene glycol, EGTA and EDTA. In further experiments, the cells were . . . in a lysis buffer which also contained the additives imidazole, lysine or spermine in addition to the above-mentioned lysis reaction. 2 µl of the RNA obtained in this manner was converted with Omniscript®, obtained from the company QIAGEN, Hilden, Germany, into a standard reverse transcriptase reaction. After the completion of this reaction, 2 µl of the RT reaction solution was in real-time PCRs for the detection of a certain transcript.

Figure 5:
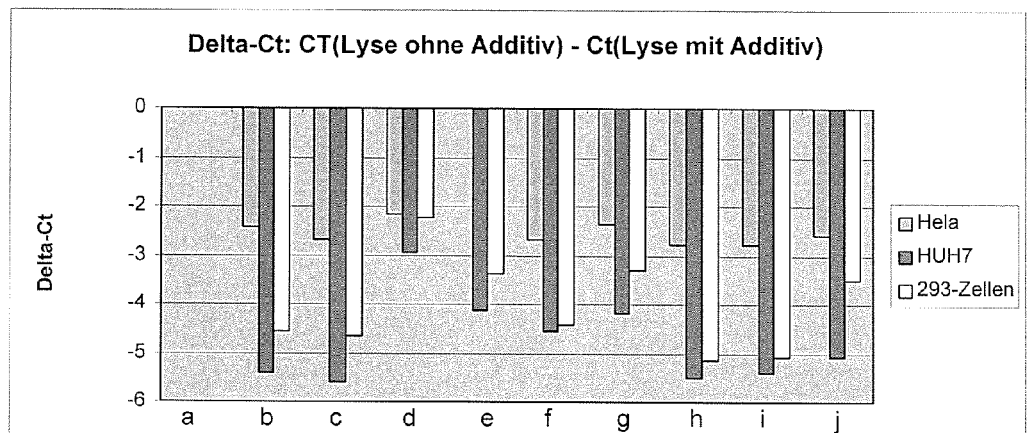
FIG. 5: a diagram showing the stabilising effect of different additives during the use of different concentrations in different cell cultures in one embodiment of the stabilisation method according to the invention.

Result:

FIG. 5 shows a diagram in which the Delta Ct values of the different samples were compared. It shows that the samples of the cellular RNA of the different cell cultures showed negative Ct values in the region of about −2 to −5.5 in the presence of different concentrations of the additives in contrast to the samples which were obtained using the −standard standard lysis buffer without additives. This indicates a considerably improved stability of the RNA in the samples containing additives.

Example 6

Stabilisation of Cellular RNA in Cell Lysates in the Presence of Additives

Cells were lysed in a lysis buffer with or without potentially stabilising additive. RNA was analysed on a denatured gel for the determination of the RAN stabilisation. But, as the RNA is complexed with cellular substance, this first has to be cleaned via Rneasy® (QIAGEN GmbH, Hilden, Germany), so that an analysis on a denaturing gel becomes possible. The integrity of the RNA can be determined by means of the 18S and 28S rRNA bands.

Execution:

40000 HepG2 cells were incubated in a suitable medium for a period of 3 days. The cells were respectively lysed in the following lysis buffers:
1: column 1: a lysis buffer containing Nonidet-P40, polyethylene glycol (PEG), EGTA and EDTA
2: column 2: as 1, additionally containing further 2 mM EGTA
3: column 3: as 1, additionally containing further 2 mM EDTA
4: column 4: a lysis buffer containing Nonidet-P40, EGTA and EDTA
5: column 5: as 1, additionally 1 mM lysine,
6: column 6: as 1, additionally 0.2 mM spermine and
7. column 7: as 1, additionally 10 mM imidazole.

After the lysis in the mentioned lysis buffers, the RNA obtained in the lysate was cleaned via Rneasy and the degradation was checked on a denaturing gel (Agilent BioAnalyzer).

Figure 6:
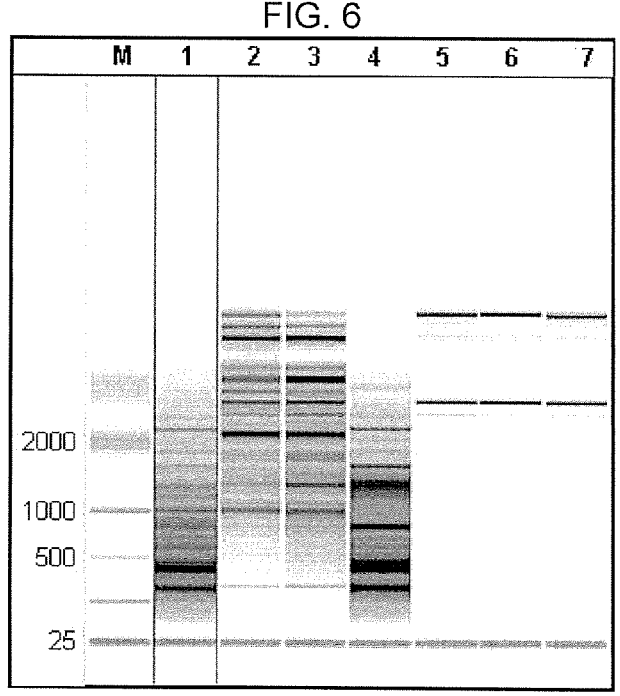
FIG. 6: the result of a gel analysis of different cell lysates.

Result:

FIG. 6 shows the result of the gel analysis. The degradation of cellular RNA in the simple lysis buffer with or without PEG (columns 1 and 4) can be clearly seen. The RNA in the presence of the additives lysine, spermine, or imidazole (columns 5, 6 and 7) did not show any degradation signs in contrast. An improved, but not sufficient stabilisation was found in the presence of increased concentrations of the nuclease inhibitors EGTA or EDTA (columns 2 and 3).

Example 7

Stabilisation of Cellular RNA of Cell Lysates by Additives at Room Temperature

Cells were lysed in a lysis buffer which contained imidazole. For the purpose of comparison, cellular RNA was cleaned via Rneasy. The lysates were not subjected to an additional purification step and therefore still contained all RNases. By the stabilisation of the RNA effected by means of the additive imidazole and possibly further cellular substances contained in the sample, the degradation of the RNA in the lysates should diminish or eliminate, even during incubation at room temperature.

So as to determine the RNA stabilisation, the Ct value of a cellular transcript was determined in a comparing real-time RT-PCR. The Ct value is the PCR cycle where the PRC signal is detected for the first time, that is, becomes visible. The Delta Ct value is calculated from the difference Ct-Wert (t=0) in the present example, whereby "t" means time, and the Ct value (t=x). If the measured Delta Ct value stays at a value around 0 during the measured time, this indicates a high degree of the stabilisation, as this indicates that no significant degradation of the RNA occurs over the measured period.

Execution:

16000 293 cells were incubated in a suitable medium for a period of 3 days. On the one hand, the cells were lysed in a lysis buffer containing Nonidet-P40, polyethylene glycol, EGTA and EDTA, and imidazole on the other hand, the RNA was prepared via RNeasy® (QIAGEN, Hilden, Germany). The lysates or eluates were incubated at room temperature for 2 h maximum. 2 µl of the incubated RNA was converted with Omniscript®, (QIAGEN, Hilden, Germany), into a standard reverse transcriptase reaction at different times. After the completion of the RT reaction, 2 µl of the reaction solution was transferred to a real-time PCRs.

Figure 7:
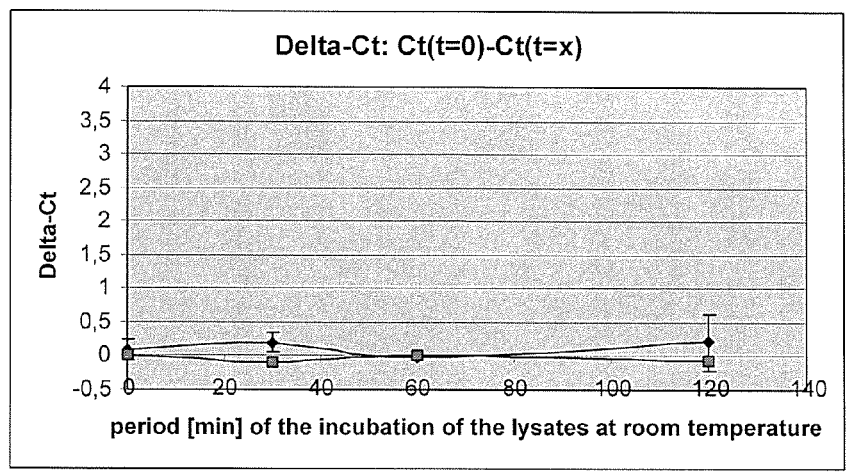
FIG. 7: a diagram in which is shown the dependence of the Delta Ct values on the incubation time.

Result:

FIG. 7 shows a diagram in which is shown the dependence of the Delta Ct values on the incubation time. The Delta Ct value of the samples, which were measured directly from the lysates, and the Delta CT value of the RNAs cleaned by means of RNeasy® (QIAGEN GmbH, Hilden, Germany) stayed approximately on the value 0. This shows that the RNAs of the lysates comprise a comparable stability to the RNA preparation cleaned by RNeasy® (QIAGEN GmbH, Hilden, Germany).

Example 8

Stabilisation of Cellular RNA with Different Cell Numbers

While the nucleic acids which were obtained from samples with small cell numbers can be stabilised by the cellular substances alone, samples which were obtained from large cell numbers still need additional agents which support a stabilisation of nucleic acids by cellular substances possibly taking place. In experiments, in which samples are used from cultures with different cell numbers, the stability of RNA after the lysis is to be determined with or without stabilising additive.

Execution:

1024-100000 cells were disseminated in 24 well dishes in a suitable medium and incubated for 3 days. In an experiment, the cells obtained in such a manner were lysed in a lysis buffer, which contains Nonidet-P40, polyethylene eglycol, EGTA and EDTA and imidazole as stabilising additive. By the addition of imidazole, a stabilisation which is possibly already present, is to be improved by cellular substances. In a further experiment, the cells were lysed in a lysis buffer, which contained Nonidet-P40, polyethylene eglycol, EGTA and EDTA, but no imidazole. The cellular RNA was cleaned via RNeasy® (QIAGEN GmbH, Hilden, Germany) in each one of the experiments described above as comparison. Respectively 2 µl of the lysates or eluates were converted with Omniscript®, (QIAGEN, Hilden, Germany), into a standard reverse transcriptase reaction. After the completion of the RT reaction, 2 µl of the reaction solution was transferred to a real-time PCRs.

So as to determine the degree of the RNA stabilisation, the CT value of a cellular transcript was determined in a comparing real-time RT-PCR. The Ct value is the PCR cycle where the PRC signal is detected for the first time, that is, becomes visible. The Delta Ct value is calculated in the present example from the difference of the CT value with a cell number X and the Ct value with the cell number 100000. If a large measure of stabilisation is reached, the Delta Ct value increases with decreasing cell number.

Figure 8:
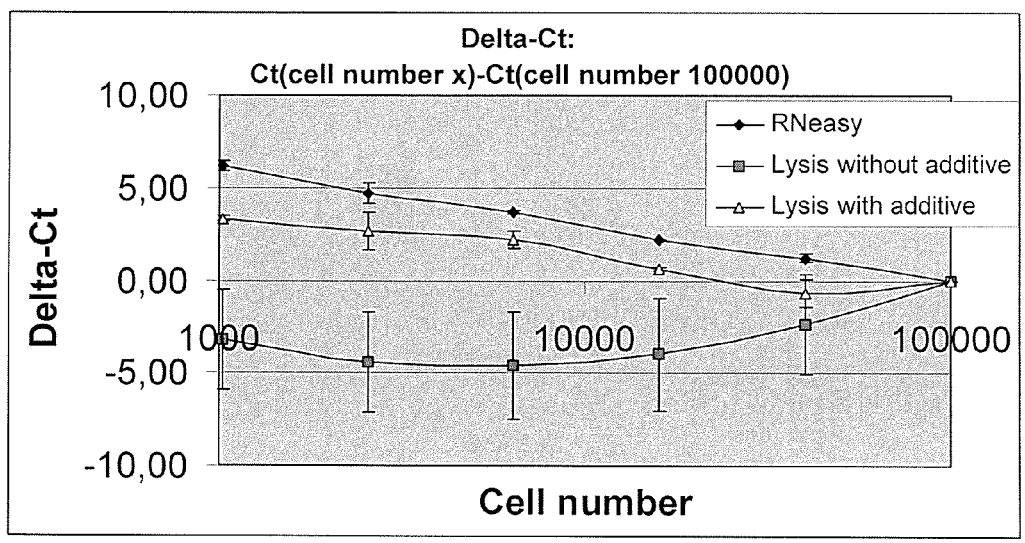
FIG. 8: a diagram in which is shown the dependence of the Delta Ct values on the cell number.

Result:

FIG. 8 shows a diagram in which the dependence of the Delta Ct value on the cell number for the samples which were cleaned via RNeasy® (QIAGEN GmbH, Hilden, Germany) of samples from lysates with imidazole as additive, and samples without additive. It is clearly shown for the samples cleaned via RNeasy® (QIAGEN GmbH, Hilden, Germany), that the Delta Ct value behaves corresponding to the cell number over the entire cell number region, that is, that a higher Delta Ct value is observed with decreasing cell number. If the cells were lysed with the lysis buffer which also contained imidazole, such a progress of the Delta Ct values corresponding to the cell numbers could only be observed from a cell number smaller or equal to 40000. But if the cells were lysed with a lysis buffer without imidazole, Delta Ct values corresponding to the cell number could only be observed under 6400 cells. Above 6400 cells, higher Delta Ct values were measured, which indicates a clear degradation of the RNA, when more than 6400 were introduced. This shows that a sufficient stabilisation without additive is possible alone by cellular substances such as proteins under a certain cell number (6400 cells here). Additives have to support the stabilisation additionally above this cell number.

III. Decrease of Inhibiting Effects

Example 9

Detectability of gDNA from Nucleoprotein Complexes

Cells were lysed in a lysis buffer with or without additives. A lysing of cells can lead to the formation of a nucleoprotein complex under the lysis conditions chosen here, so that gDNA can only be detected insufficiently in a sample obtained from a lysate. For the determination of the gDNA, the CT value was determined in a comparing real-time RT-PCR. The Ct value is the PCR cycle where the PRC signal is detected for the first time, that is, becomes visible. The Delta Ct value is calculated in this experiment from the difference of the Ct value after the lysis with addtive and the Ct value at the lysis without separation additive. The lower the Delta Ct value, the better the detectability of gDNA, and the better gDNA could be separated from the nucleoprotein complex by the additive.

Execution.

HepG2 cells were incubated in a suitable medium for a period of 3 days. As a comparative example, cells were lysed in a lysis buffer C, which contained Nonidet-P40, polyethylene glycol, EGTA and EDTA. Additionally, cells were lysed in further experiments, which also contained, in addition to the above-mentioned reagents, the additives arginine (1 mM), 2,3-dimethylpyrazine (30 mM), tyrptophane (15 mM), histidine (15 mM), indazole (10 mM) or imidazole (15 mM) in the given concentrations.

2 µl of the nucleoprotein complexes containing lysates were respectively transferred into a real-time PCRs, to detect gDNA.

Figure 9:
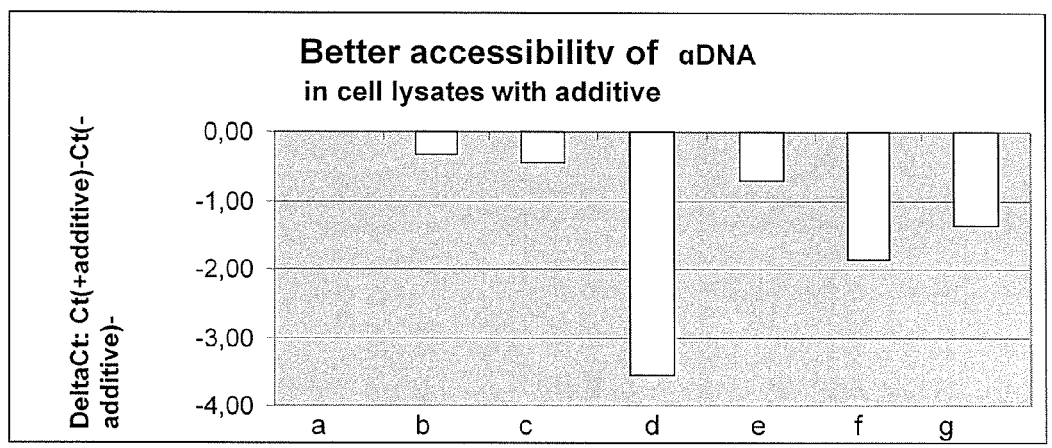
FIG. 9: a diagram showing the improved accessibility of gDNA by use of different additives in lysates which are obtained according to an embodiment of the method according to the invention for the reduction of inhibiting effects.

Result:

FIG. 9 shows a diagram in which the respectively determined Delta Ct values of the individual experiments are compared. With all additives, increased negative Delta Ct values were found compared to the sample without additive. It can be concluded therefrom that cellular gDNA can be detected better than the gDNA complexed by nucleoproteins after separation from cellular nucleoprotein complexes by the above-mentioned amines. About 0.3 to 3.5 better Delta Ct values could be achieved. This corresponds to an improvement of the detectability of gDNA by the separation caused by additive by about the factor 1.2 to 10, depending which additive was used for the decomplexing of the cellular nucleoprotein complexes.

Example 10

Improvement of the Enzymatic Degradation (DNase I) of gDNA from Cellular Nucleoprotein Complexes Cells were lysed in a lysis buffer with or without additives. A lysing of cells can lead to the formation of a nucleoprotein complex under the lysis conditions chosen here for the formation of a nucleoprotein complex, so that gDNA is only accessible insufficiently for the DNase I. The DNase I Verdau of the gDNA serves as measure of how far the gDNA is separate from the nucleoprotein complexes. If an additive leads to a decomplexing of the gDNA from the nucleoprotein complexes, the gDNA should be easier to digest by DNase I. The detection of the gDNA by means of a real-time assay served for the determination of the enzymatic degradation by DNase I. The Ct value is the PCR cycle where the PRC signal is detected for the first time, that is, becomes visible. The Delta Ct value is calculated in this experiment from the difference of the Ct value in a sample with addition of additive, but without addition of DNase I and the Ct value of a sample, to which was added additive and DNase I. The Delta $Ct_2$ value is calculated in this experiment from the difference of the Ct value in a sample without addition of additive and DNase I, and the Ct value of a sample, to which was added DNase I, but no additive. The ΔDelta-Ct value is calculated in this experiment from the difference: $DeltaCt_1$-$DeltaCt_2$. The lower (high amount of the negative value) the ΔDelta-Ct value, the better the gDNA can be degraded through the DNase I, which is a sign for a better accessibility of the gDNA for the DNase I.

Execution:
HepG2-Zellen HepG2 cells were incubated in a suitable medium for a period of 3 days. As a comparative example, cells were lysed in a lysis buffer C, which contained Nonidet-P40, polyethylene glycol, EGTA and EDTA. On the other hand, the cells were lysed in a lysis buffer which contained, in addition to the substances mentioned above, also respectively one of the following additives in the respectively given concentrations: arginine (1 mM), 2,3-dimethyl pyrazine (30 mM), aminothazole (15 mM), indazole (30 mM), benzimidazole (15 mM), imidazole (15 mM), tryptophane (15 mM), histidine (15 mM), proline (5 mM) or ammonium sulfate (30 mM). Subsequently, a DNase I Verdau was carried out as described above and respectively 2 μl of the reaction solution obtained thus was transferred to real-time PCRs to detect gDNA.

Figure 10:
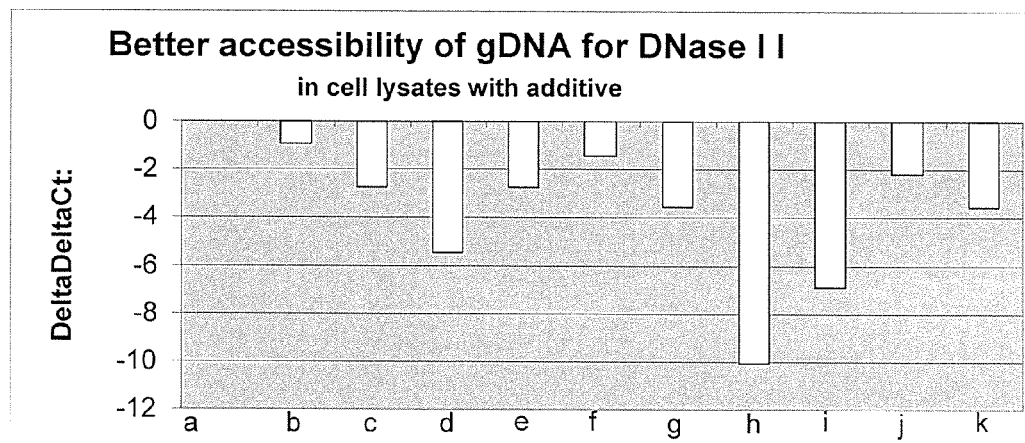
FIG. 10: a diagram showing the improved accessibility of gDNA for DNase I by use of different additives in lysates which are obtained according to an embodiment of the method according to the invention for the reduction of inhibiting effects.
Figure 10:
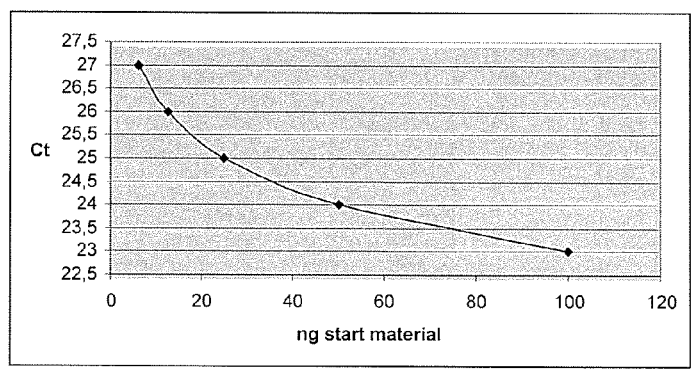

Result:
FIG. 10 shows a diagram in which the different Delta Ct values were compared for different samples.

All used additives led to ΔDelta-Ct values which were more negative which indicated that the cellular gDNA of cellular nucleoprotein complexes can be degraded by decomplexing by means of the above-mentioned additives reinforced by the DNase I. Depending on the additive, 0.3 to 10 cycles of better ΔDelta-Ct values were obtained. This corresponds to an improvement of the enzymatic degradability of the gDNA by DNase I, which is achieved by the addition of the additives with the factor ~1.2 to ~100.

A Ct differences of 2 cycles corresponds for example to a change of the amount of starting material available for the PCR, gDNA in the sample, by the factor 4. In this manner, the factor can be correlated with the improvement with which the accessibility of the gDNA is improved. This context is explained by means of idealised hypothetic values which do not emanate from any experiments, in FIGS. 10.a.1 and 10.a.2.

Example 11

Concentration Dependence of the Improvement of the Enzymatic Degradation (DNase I) of gDNA from Cellular Nucleoprotein Complexes The series of experiments carried out above under example 10 was carried out in an analogous manner using different concentrations of imidazole as additive.

Execution:
HepG2-Zellen 29 cells were incubated in a suitable medium for 3 days. As a comparative example, cells were lysed in a lysis buffer C, which contained Nonidet-P40, polyethylene glycol, EGTA and EDTA. Subsequently, a DNase I Verdau was carried out as described above and respectively 2 μl of the reaction solution obtained thus was transferred to real-time PCRs to detect gDNA.

Result:
FIG. 11 shows the concentration dependency of the ΔDelta-Ct from the concentration of the indazole added to the lysate. The enzymatic degradation of the gDNA by DNase I could be improved by a factor 40 when adding 20 mM indazole.

Example 12

Better DNase I Verdau of gDNA in gDNA/RNA Mixtures in the Presence of Additives

It is tested, if, in nucleic acid mixtures of RNA and DNA, which were cleaned by silica membranes (Rneasy® (QIAGEN GmbH, Hilden, Germany), a use of additives for the decrease of the inhibition by biomolecules will lead to an improved enzymatic degradation by DNase I. For this, cleaned gDNA and cleaned RNA was received in a lysis buffer with or without additive. The accessibility of the gDNA for the DNase I is determined by an enzymatic degradation by means of DNase I with a subsequent determination of the gDNA-content by real-time PCR. IN the real-time PCR, the Ct value is the PCR cycle, where the PRC signal is detected for the first time, that is, becomes visible. The delta Ct value is calculated in this experiment from the difference of the Ct value after the lysis with additive and the Ct value at the lysis without additive. The lower, that is, the more negative, the delta Ct value, the more effective is the enzymatic degradation, which again indicates an improved accessibility of the gDNA for the DNase I.

Execution:
RNA was cleaned via Rneasy® (QIAGEN GmbH, Hilden, Germany). gDNA was cleaned via QIAamp® (QIAGEN GmbH, Hilden, Germany). 20 ng of the gDNA and 20 ng of the RNA were combined to a sample. An enzymatic degradation by DNase I The DNase Verdau of the lysates was carried out in the QuantiTect® Real-time buffer (QIAGEN GmbH, Hilden, Germany), whereby 150 μM (as end concentration) of $CaCl_2$ was added. The reactions respectively contained 20 ng RNA and 20 ng gDNA, 0.5 U DNase (from the company Ambion, USA), primers, nucleotides, HotstarTaq polymerase and die listed additives. The reaction was stopped by heat activation at the PCR. For the determination of the remaining gDNA, a real-time PCR is carried out.

Figure 12:
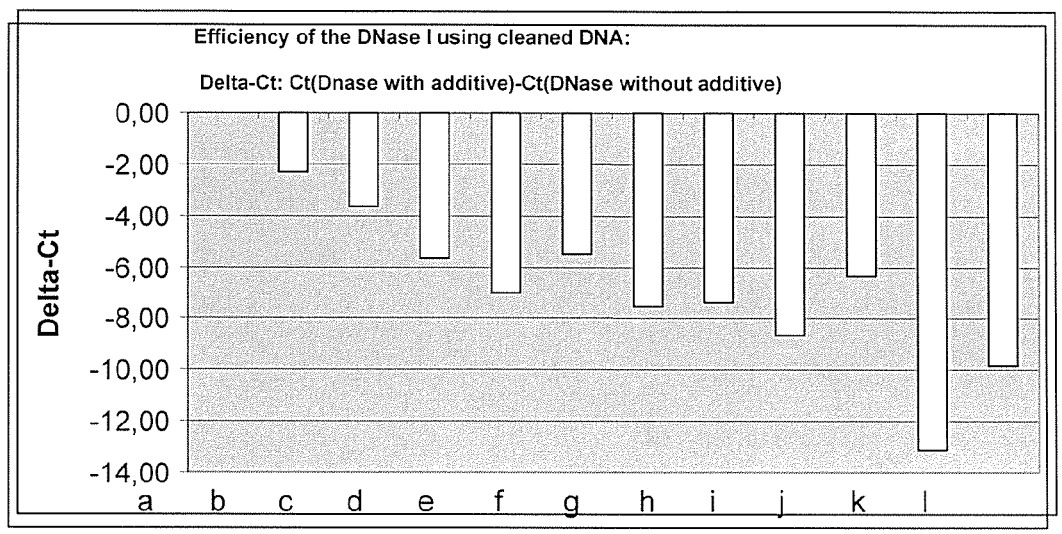
FIG. 12: a diagram showing the measured Delta Ct values during the use of cleaned DNA in an embodiment of the method according to the invention for the reduction of inhibiting effexts.

Result:

FIG. 12 shows a comparison of the Delta Ct values obtained respectively. The diagram shows that gDNA in gDNA/RNA mixtures cleaned in the presence of the used additives is degraded by DNase I in a clearly better manner. 2 to 13 cycles improved Delta Ct values could be shown. This corresponds to an improvement of the degradation of gDNA by the DNase I by the factor ~4 to >1000, depending which additive was used.

Example 13

Decrease of the Inhibiting Effect During the Detection of gDNA and RNA from Cell Lysates Cells were lysed in a lysis buffer with or without distamycine D. A lysis of cells leads to the formation of nucleoprotein complexes, so that RNA can only be detected insufficiently. For the decomplexing of the gDNA or RNA, distamycine D was used, which primarily binds double-strand DNA in the small cavity. For the determination of the gDNA, the CT value was determined in a comparing real-time RT-PCR. The RNA was determined in a comparing real-time RT-PCR. The Ct value is the PCR cycle where the PRC signal is detected for the first time, that is, becomes visible. The delta Ct value is calculated in this experiment from the difference of the Ct value after the lysis with additive and the Ct value at the lysis without additive. The lower, that is, the more negative, the delta Ct value, the better is the detectability of gDNA or RNA, and the better could the gDNA or RNA be decomplexed from the nucleoprotein complex by the additive.

Execution:

HeLa cells which grow in suspension were incubated in a suitable medium. On the one hand, the cells were lysed in a lysis buffer, which contained Nonidet-P40, polyethylene glycol, EGTA and EDTA. On the other hand, the cells were lysed in a lysis buffer which also contained distamine D in different concentrations as additive in addition to the above-mentioned substances.

Respectively 2 µl of the lysates obtained respectively thus were transferred to real-time PCRs or real-time RT-PCRs to detect gDNA or RNA.

Figure 13:
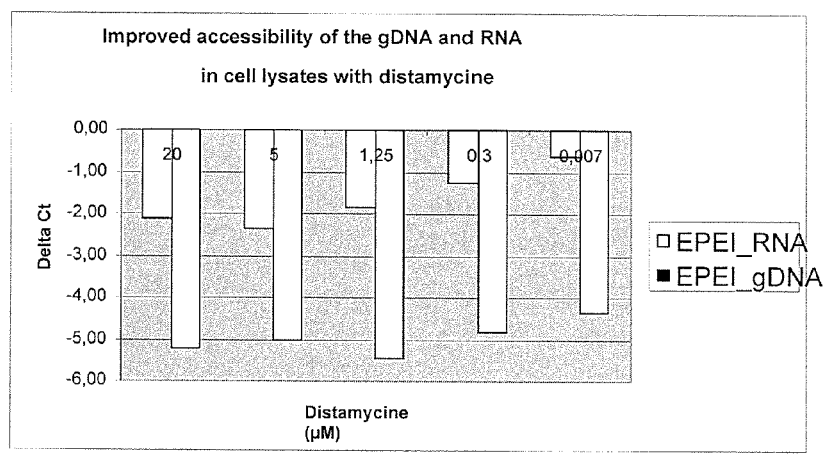
FIG. 13: a diagram showing the improved accessibility of gDNA and RNA in lysates in the presence of distamycine D according to the invention.

Result:

FIG. 13 shows a diagram in which the respectively determined delta Ct values of the individual experiments are compared. It can be seen in the diagram that cellular gDNA and RNA can be detected easier after the decomplexing of cellular nucleoprotein complexes by distamine D that in the samples without distamine D. The degree of the improvement depends on the concentration of distamycine. For the gDNA, improvements of the Ct value of >4 cycles could be achieved even with small concentrations of 70 µM. This corresponds to an improvement of the factor >10.

The Ct value improvements during the detection of the RNA during the use od distamycine as additive are smaller here. This can be attributed that distamycine primarily binds DNA. The achieved effect is thereby based essentially on the decomplexing of protein DNA complexes, into which the RNA is woven and also released. The effect on the detectability of RNA is thereby essentially of the indirect type.

Example 14

Decrease of the Inhibiting Effect on RNA, Normed to the Detectability of DNA

Cells were lysed in a lysis buffer with or without additives. The lysis of cells leads to the formation of nucleoprotein complexes, so that RNA can only be detected insufficiently. For the detection of the RNA, the CT value was determined in a comparing two-tube real-time RT-PCR. The Ct value is the PCR cycle where the PRC signal is detected for the first time, that is, becomes visible. The delta Ct value is calculated in this experiment from the difference of the Ct value after the lysis with additive and the Ct value at the lysis without additive. The Ct values of the RNA were normalised on the Ct values of the gDNA. A Ct difference of e.g. 2 cycles corresponds to a change of the accessibility of the RNA by the reverse transcriptase by the factor 4. The factor can be determined in this manner, with which the accessibility of the RNA from nucleoprotein complexes, compared to the accessibility of the gDNA from nucleoprotein complexes by the respective additive.

Execution:

HepG2 cells were incubated in a suitable medium for 3 days. On the one hand, the cells were lysed in a lysis buffer, which contained Nonidet-P40, polyethylene glycol, EGTA and EDTA. On the other hand, the cells were lysed in a lysis buffer which contained, in addition to the substances mentioned above, also respectively one of the following additives in the respectively given concentrations: arginine (1 mM), 2,3-dimethylpyrazine (30 mM), aminothazole (15 mM), indazole (30 mM), benzimidazole (15 mM), histidine (10 mM), proline (5 mM), tryptophane 10 mM, indazole 30 mM), ammonium sulfate 30 mM or imidazole (15 mM). 2 µl of the lysates obtained in this manner was used in a reverse transcriptase reaction with Omniscript RT® (QIAGEN, Hilden, Germany). After the completion of the RT reaction, 1 µl of the reaction solution was respectively transferred to a real-time PCRs, so as to detect the corresponding cDNA.

Figure 14:
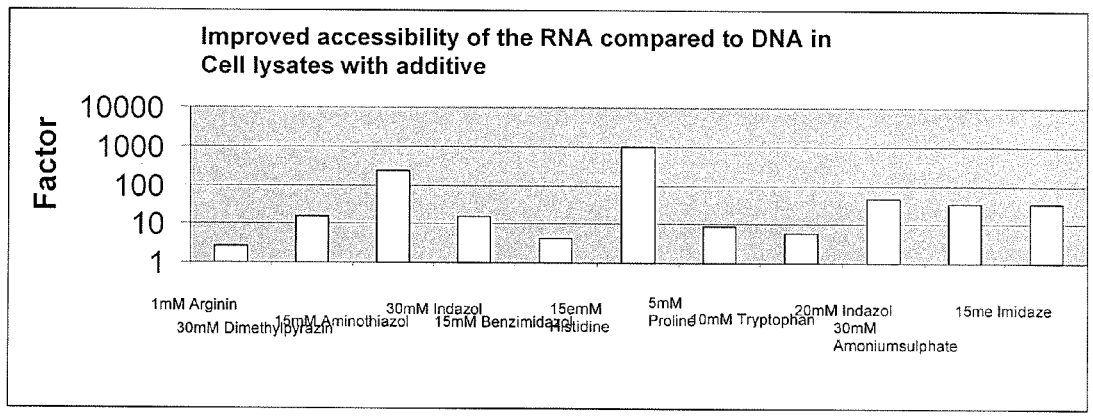
FIG. 14: a diagram showing the improved accessibility of RNA in comparison to DNA in cell lysates with different additives according to the invention.

Result:

FIG. 14 shows a diagram in which the respectively achieved improvements with the detectability of cellular RNA are compared. The diagram shows that cellular RNA can be detected easier after decomplexing of the cellular nucleoprotein complexes by the above-mentioned additives than RNA from lysate samples, to which no additive was added. Improvements with the factor 2-1000 could be measured. This shows that a clear decomplexing of the RNA from nucleoprotein complexes results due to the use of the respective additive.

IV. Masking

Example 15

Differential Masking of DNA in Mixtures of Cleaned Genomic DNA and Cleaned RNA

Masked DNA should be more difficult to amplify than RNA. Real-time PCR or RT-PCR of DNA and RNA can show the measure of the differential masking of the DNA compared to the RNA, when additives are used for the masking of the gDNA.

The Delta Ct value is defined as the difference of the Ct value of samples to which were added additive and the Ct value of samples to which was not added any additive. A high value showed the masking of the DNA compared to the RNA.

Execution:

Human gDNA and RNA was respectively cleaned by means of QIAamp® (QIAGEN GmbH, Hilden, Germany) or Rneasy® (QIAGEN GmbH, Hilden, Germany) 20 ng of the gDNA and 20 ng of the RNA were combined to a sample. Spermine up to an end concentration of 5 or 20 µM was added to some some samples. 2 µl of the rest after centrifugation was transferred into a real-time PCR or a two tube real-time RT-PCR.

Figure 15:
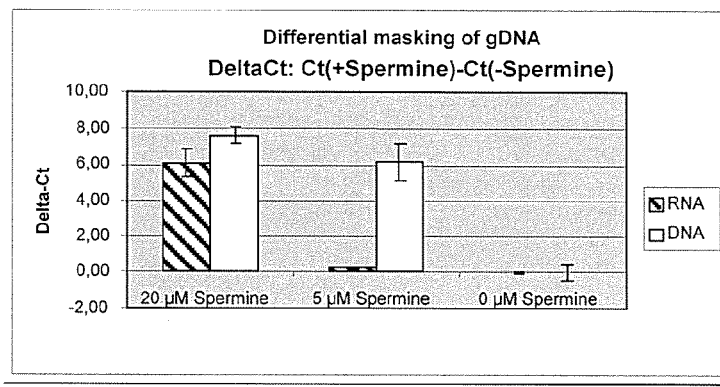
FIG. 15: a diagram showing the effect of the differential masking of gDNA compared to RNA in cell lysates according to the invention with different concentrations of spermine by means of the measured Delta Ct values.

Result:

FIG. 15 shows a diagram in which the respectively determined delta Ct values of the individual experiments are compared. It can be seen in the diagram that both nucleic acids, gDNA and RNA are masked during the 20µµ spermine, when using 5 µM spermine, gDNA can be selectively masked. With 5 µM spermine, a Delta Ct displacement of 6 cycles could be measured, which gives a masking of the gDNA with the factor of ~500. In contrast, for the RNA was not found a Delta Ct displacement.

Example 16

Masking of RNA in Cell Lysates by Different Additives

Masked RNA should be worse to amplify than gDNA from the same preparation or the same lysate. Real-time RT-PCR of the masked RNA adjusted to the real-time PCR of gDNA should show the extent of the differential masking of the DNA compared to the RNA. The Delta Ct value is defined as the difference of Ct values of samples which were obtained by lysis with additive and the Ct value of samples which were obtained by lysis without additive in the present experiment. The Delta Ct value was normalised on the Ct values which were achieved by the RNA in the real-time RT-PCR.

A high value showed the masking of the DNA compared to the RNA.

Execution:

On the one hand, human gDNA and RNA with a detergent-containing lysis buffer (Nonidet-P40, plyethylene gylcol, EGTA and EDTA) was obtained from HepG2 cells. On the other hand, the additives ammonium sulfate, glycine or ammonium hydrogen phosphate in a concentration of 30 mM or urea in a concentration of 5 mM for the differential masking of gDNA.

The differential masking of the DNA compared to RNA was subsequently determined via real-time PCR and real-time RT-PCR.

Figure 16:
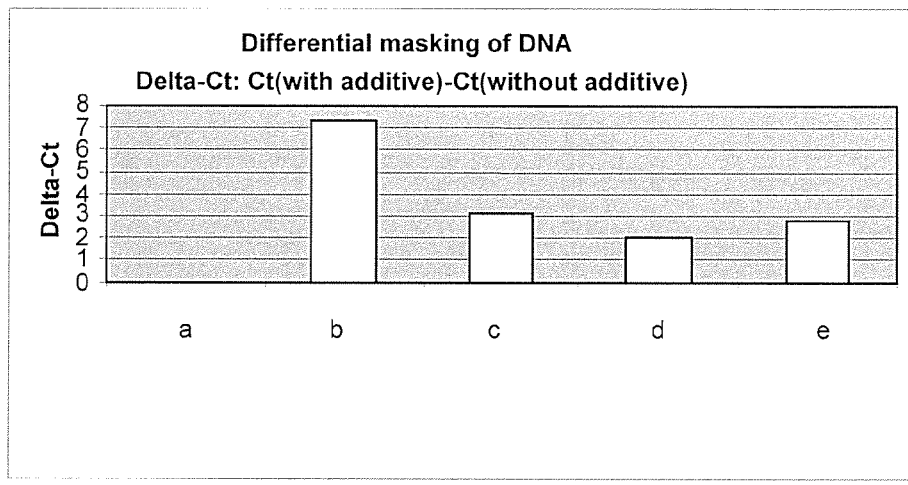
FIG. 16: a diagram showing the effect of the differential masking in gDNA in cell lysates according to the invention with the use of different additives.

Result:

FIG. 16 shows a diagram in which the respectively determined delta Ct values of the individual experiments are compared. It can be seen in the diagram that genome DNA in lysis buffer with the mentioned additives leads to higher Delta Ct values normalised on the Ct values of the RNA. This shows a masking of the DNA compared to the RNA. In the case of the indazole, a masking of nearly 7 Cts was achieved, which indicates that about 100× less RNA was detected in this solution due to the masking.

Example 17

Masking of Genomic DNA in Cell Lysates by Different Additives

Masked DNA should be worse to amplify than RNA from the same preparation. Real-time RT-PCR of the masked RNA adjusted to the real-time PCR of gDNA should show the extent of the differential masking of the DNA compared to the RNA.

In this experiment, the delta Ct value is defined as the difference of the Ct value (DNA) and Ct-Wert (RNA). A negative delta CT value showed the masking of the RNA compared to the DNA.

Execution:

On the one hand, human gDNA and RNA with a detergent-containing lysis buffer (Nonidet-P40, plyethylene gylcol, EGTA and EDTA) was obtained from 40.000 cells. On the other hand, one of the following additives were respectively added in the given concentrations, so as to mask RNA differentially: glutamic acid (15 mM), arginine (5 mM), 2,3-dimethylpyrazine (15 mM), benzimidazole (15 mM), imidazole (15 mM) or histidine (15 mM). The concentrations are respectively end concentrations. The differential masking of the DNA compared to RNA was subsequently determined via real-time PCR and real-time RT-PCR.

Figure 17:
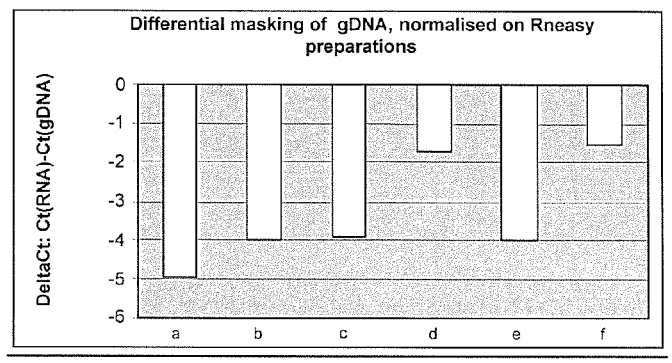
FIG. 17: a diagram showing the effect of the differential masking of gDNA according to the invention, normalised to RNeasy preparations.

Result:

FIG. 17 shows the Delta Ct values obtained respectively. It can be seen from the diagram that RNA in the lysis buffers containing additive resulted in negative delta Ct values. This shows a masking of the DNA compared to the RNA. In the case of the glutamic acid and arginine, 2,3-dimethylpyrazine and imidazole, a masking of 4 Cts was achieved, which indicated that about 10× less DNA was detected in this solution due to the masking.

Example 18

Concentration Dependence of the Masking of Genomic DNA in Cell Lysates

Masked DNA should be worse to amplify than RNA from the same preparation. Real-time RT-PCR of the masked RNA adjusted to the real-time PCR of gDNA should show the extent of the differential masking of the DNA compared to the RNA.

In this experiment, the Delta Ct value is defined as the difference of the Ct value (RNA) and the Ct value (gDNA). A negative Delta CT value showed the masking of the RNA compared to the DNA.

Execution:

On the one hand, human gDNA and RNA with a detergent-containing lysis buffer (Nonidet-P40, plyethylene gylcol, EGTA and EDTA) was obtained from HepG2 cells. On the other hand, the additive arginine was respectively added to the lysis buffer in different concentrations to achieve a differential masking. The shown concentrations are respectively end concentrations of the arginine in the lysate. The differential masking of the DNA compared to RNA was subsequently determined via real-time PCR and real-time RT-PCR.

Figure 18:
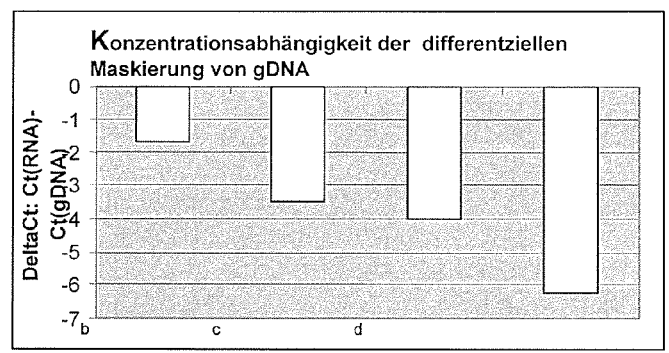
FIG. 18: a diagram showing the concentration dependence of the effect of the masking of gDNA in cell lysates according to the invention.

Result:

FIG. 18 shows a diagram in which the respectively determined Delta Ct values of the individual experiments are compared. It can be seen from the diagram The Delta Ct values are more negative, the higher the end concentration of arginine in the buffer. This shows a masking of the DNA compared to the RNA. In this experiment series at 6 mM arginie, a maximum masking was obtained. A Delta Ct value of "−6" corresponds to an approximately 500 times worse detection of the gDNA.

Example 19

Masking of RNA in Cell Lysates by Different Additives

Masked RNA should be worse to amplify than gDNA from the same preparation or the same lysate. Two-tube real-time RT-PCR of the masked RNA adjusted to the real-time PCR of gDNA should show the extent of the differential masking of the RNA compared to the DNA. In this experiment, the Delta Ct value is defined as the difference of the Ct value (DNA) and Ct-Wert (RNA). A negative Delta CT value showed the masking of the RNA compared to the DNA.

Execution:

On the one hand, human gDNA and RNA with a detergent-containing lysis buffer (Nonidet-P40, plyethylene gylcol, EGTA and EDTA) was obtained from HepG2 cells. On the other hand, one of the following additives were respectively added in the given concentrations, so as to mask RNA differentially: proline (20 mM), indazole (20 mM) or ammonium sulfate (30 mM). The concentrations are respectively end concentrations. The RNA was subsequently employed in a 20 µl reverse transcriptase using the lysate. 2 µl of the reaction solution obtained thus was then transferred into the real-time PCR. As a comparison, a real-time PCR was carried out without a prior transcriptase reaction.

Figure 19:
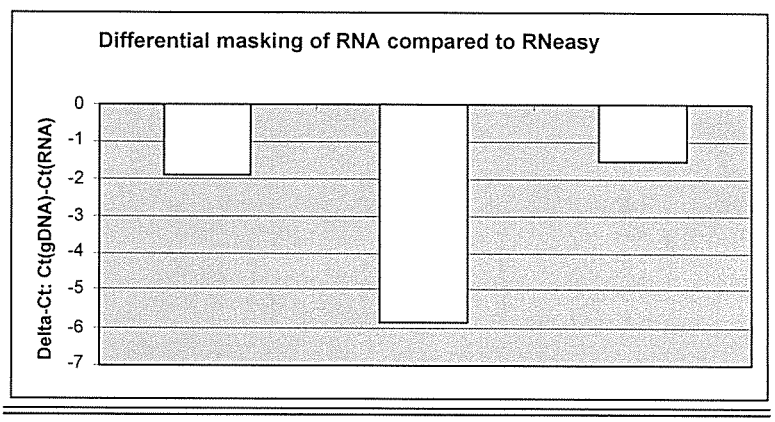
FIG. 19: a diagram showing the effect of the masking of RNA according to the invention.

Result:

FIG. 19 shows a diagram in which the respectively determined Delta Ct values of the individual experiments are compared. It can be seen from the diagram that RNA in the lysis buffers containing additive resulted in negative Delta Ct values. This shows a masking of the RNA compared to the gDNA. In the case of the indazole, a masking of nearly 6 Cts was achieved, which indicates that about 400× less RNA was detected in this solution due to the masking.

Example 20

Use of the Substances According to the Invention for Treating Biological Samples or Organisms and Measurement of the pH Values Execution:

On the one hand, human gDNA and RNA with a detergent-containing lysis buffer was obtained from HepG2 cells. Alternatively, a) arginine (5 mM) b) arginine and proline (concentration each 5 mM) c) imidazole (15 mM) or d) guanosine (20 mM) was added to this lysis buffer. After the addition of the solution to the cells, the pH value of the lysate obtained in this manner was determined.

Result:

The pH values were determined as follows:
a) sample traeted with arginine-containing solution: pH 7.5 to 8
b) sample treated with arginine-proline-containing solution: pH 7.4 to 8
c) sample treated with imidazole-containing solution: pH 7.5 to 8
d) sample treated with guanosine-containing solution: pH>9

The invention claimed is:

1. A method for stabilizing at least one species of nucleic acid and species of protein comprised in a sample, said method comprising mixing the sample with a fluid preparation to form a sample preparation comprising the at least one species of nucleic acid and the at least one species of the protein, and wherein the fluid preparation comprises at least one nitrogenous compound which is at least one selected from the group consisting of:
a) polyamines;
b) amino acids, and oligo and polypeptides;
c) nitrogenous heterocyclic compounds including homo or hetero polymers which comprise at least one nitrogenous compound;
d) amines of the type $R^1R^2NR^3$, whereby $R^1$, $R^2$ and $R^3$ are chosen independently from one another and are selected from the group consisting of H, $C_1$-$C_5$ alkyl groups and aryl groups, whereby $R^1$, $R^2$ and $R^3$ are not H simultaneously;
e) carboxylic acid amides;
f) inorganic ammonium salts;
g) inner salt compounds containing ammonium groups;
h) antibiotics binding nucleic acid; and
i) compounds which bind in the small cavity of DNA;
wherein an amount of the nitrogenous compound is chosen so as to minimize precipitation of the nucleic acid and protein present during and after said mixing, wherein the ratio of concentration of the at least one species of nucleic acid and protein in the sample preparation is the same as the ratio of concentration of the at least one species of nucleic acid and protein in the sample, and wherein the species of nucleic acid and species of protein in the sample are not encapsulated by a cell membrane.

2. A method of claim 1, wherein at least one of said species of nucleic acid or protein is immobilized on a solid carrier before, during and/or after said mixing of said sample with said fluid preparation.

3. A method of claim 1, wherein at least one of said species of nucleic acid and/or protein in said sample is dissolved and/or suspended after said mixing with said fluid preparation.

4. A method for stabilizing at least one species of nucleic acid and species of protein comprised in a sample, said method comprising mixing the sample with a fluid preparation to form a sample preparation comprising the at least one species of nucleic acid and the at least one species of the protein, and wherein the fluid preparation comprises at least one nitrogenous compound which is at least one selected from the group consisting of:
a) polyamines;
b) amino acids, and oligo and polypeptides;
c) nitrogenous heterocyclic compounds including homo or hetero polymers which comprise at least one nitrogenous compound;
d) amines of the type R1R2NR3, whereby R1, R2 and R3 are chosen independently from one another and are selected from the group consisting of H, C1-C5 alkyl groups and aryl groups, whereby R1, R2 and R3 are not H simultaneously;
e) carboxylic acid amides;
f) inorganic ammonium salts;
g) inner salt compounds containing ammonium groups;
h) antibiotics binding nucleic acid; and
i) compounds which bind in the small cavity of DNA;
wherein an amount of the nitrogenous compound is chosen so as to minimize precipitation of the nucleic acid and protein present during and after said mixing,
wherein the ratio of concentration of the at least one species of nucleic acid and protein in the sample preparation is the same as the ratio of concentration of the at least one species of nucleic acid and protein in the sample,
wherein the species of nucleic acid and species of protein in the sample are not encapsulated by a cell membrane, and
wherein said sample comprises a biological sample which was subjected to lysis and optionally subjected to at least one further purification step, before said mixing with said fluid preparation.

5. A method of claim 1, wherein said sample comprises a biological sample which comprises at least one species of nucleic acid and at least one species of protein and said biological sample is contacted with said fluid preparation to obtain a lysate.

6. A method of claim 1, wherein DNA and/or RNA is dissolved, suspended, or immobilized on a carrier in said sample preparation.

7. A method of claim 1, wherein the nitrogenous compound is selected from the group of
   a) polyamines,
   b) polar, alkaline and acidic amino acids,
   c) heterocyclic compounds, and
   d) antibiotics binding nucleic acid selected from the group consisting of distamycines, mitomycines, norfloxacins, streptozocine, duocarmycines, actinomycines, and aminoglycisides.

8. A method of claim 7, wherein said polyamines are selected from the group consisting of unbranched polyamines with 2 to 6 amino groups, said amino acids are selected from the group consisting of lysine, arginine, histidine, and glutamic acid, the heterocyclic compounds are selected from the group consisting of imidazole, 2,3-dimethylpyrazine, pyrimidine and guanine.

9. A method of claim 1, wherein said nitrogenous compound comprises spermidine.

10. A method of claim 4, wherein said lysis is conducted using a detergent and/or protease.

11. A method of claim 10, wherein said lysis is conducted using proteinase K.

12. A method of claim 4, wherein said mixing is conducted after an enzymatic degradation by a nuclease.

13. A method for stabilization of at least one biomolecule contained in a sample comprising at least one species of nucleic acid and at least one species of protein, the method comprising mixing the sample with a fluid preparation to form a sample preparation, and wherein the fluid preparation comprises at least one nitrogenous compound selected from the group consisting of arginine, imidazole, proline, lysine, spermine, spermidine, glutamic acid, indazole, thymine, thymidine, guanine, guanosine, adenine, histidine, tryptophane, and ammonium sulphate, wherein the species of nucleic acid and species of protein in the sample are not encapsulated by a cell membrane.

14. A method of claim 1, wherein by employing said at least one nitrogenous compound, direct separation of species comprised in the sample preparation is not necessary and/or can take place at a later time.

15. The method of claim 13, wherein an amount of the nitrogenous compound is chosen so as to minimize precipitation of the biomolecule during and after said mixing, and wherein the ratio of concentration of the at least one biomolecule in the sample preparation is the same as the ratio of concentration of the biomolecule in the sample.

16. The method of claim 13, wherein said sample comprises a biological sample which was subjected to lysis and optionally subjected to at least one purification step before said mixing with said fluid preparation.

17. The method of claim 13, wherein the sample preparation is suitable for use directly for analysis of the biomolecule without any further reconditioning step.

18. The method of claim 1, wherein the concentration of the nitrogenous compound in the sample preparation is from 0.001 mM to 1 M.

19. The method of claim 18, wherein:
   (a) the nitrogenous compound is a polyamine and the concentration of the polyamine in the sample preparation is from 0.001 mM and 15 mM; or
   (b) the nitrogenous compound is an amino acid and the concentration of the amino acid in the sample preparation is from 0.001 mM to 20 mM; or
   (c) the nitrogenous compound is a nitrogenous heterocycle and the concentration of the nitrogenous heterocycle in the sample preparation is from 0.001 to 20 mM; or
   (e) the nitrogenous compound is a carboxylic acid amines and the concentration of the carboxylic acid amines in the sample preparation is from 0.001 to 15 mM; or
   (f) the nitrogenous compound is an inorganic ammonium compound and the concentration of the inorganic ammonium compound in the sample preparation is from 0.001 mM to 100 mM; or
   (g) the nitrogenous compound is an inner salt compound containing ammonium groups and the concentration of the inner salt compound containing ammonium groups in the sample preparation is from 0.001 mM to 300 mM.

20. The method of claim 1, wherein the sample preparation is suitable for analysis of the nucleic acid or protein without any further reconditioning step.

* * * * *